US010870887B2

(12) United States Patent
Rotthier et al.

(10) Patent No.: US 10,870,887 B2
(45) Date of Patent: Dec. 22, 2020

(54) MUTATIONS IN SPTLC2 GENE ASSOCIATED WITH SENSORY NEUROPATHY

(71) Applicants: VIB VZW, Ghent (BE); UNIVERSITEIT ANTWERPEN, Antwerp (BE); UNIVERSITY OF ZURICH, Zurich (CH); MEDICAL UNIVERSITY OF GRAZ, Graz (AT)

(72) Inventors: Annelies Rotthier, Olen (BE); Vincent Timmerman, Broechem-Ranst (BE); Michaela Auer-Grumbach, Graz (AT); Thorsten Hornemann, Zurich (CH)

(73) Assignees: VIB VZW, Ghent (BE); UNIVERSITEIT ANTWERPEN, Antwerp (BE); UNIVERSITY OF ZURICH, Zurich (CH); MEDICAL UNIVERSITY OF GRAZ, Graz (AT)

( * ) Notice: Subject to any disclaimer, the term of this patent is extended or adjusted under 35 U.S.C. 154(b) by 115 days.

(21) Appl. No.: 15/814,766

(22) Filed: Nov. 16, 2017

(65) Prior Publication Data

US 2018/0155790 A1 Jun. 7, 2018

Related U.S. Application Data

(63) Continuation of application No. 13/823,080, filed as application No. PCT/EP2011/066212 on Sep. 19, 2011, now Pat. No. 9,828,638.

(60) Provisional application No. 61/403,619, filed on Sep. 17, 2010.

(30) Foreign Application Priority Data

Sep. 17, 2010 (GB) ..................................... 1015581

(51) Int. Cl.
*C12Q 1/68* (2018.01)
*C12Q 1/6883* (2018.01)
(52) U.S. Cl.
CPC ..... *C12Q 1/6883* (2013.01); *C12Q 2600/156* (2013.01)
(58) Field of Classification Search
None
See application file for complete search history.

(56) References Cited

U.S. PATENT DOCUMENTS 6,582,908 B2 * 6/2003 Fodor .................. B01J 19/0046
435/288.3

FOREIGN PATENT DOCUMENTS

WO WO 2011/089146 A1 7/2011
WO WO 2012/035164 A1 3/2012

OTHER PUBLICATIONS

Rothstein et al; PNAS, vol. 91, pp. 4155-4159; 1994.*
NEB catalog (1998/1999), pp. 121, 284.*
International Search Report PCT/EP2011 /066212, dated Jan. 18, 2012.
Bejaoui I et al., "SPTLCI is mutated in hereditary sensory neuropathy, type I . Nature Publishing Group, http://genetics.nature.com, *Nature Genetics*," vol. 27, pp. 261-262, (Mar. 2001).
Dawkins et al., "Mutations in SPTLCI , encoding serine palmitoyltransferase, long chain base subunit-I , cause hereditary sensory neuropathy type I," Nature Publishing Group, http://genetics.nature.com, *Nature Genetics*, vol. 27, pp. 309-312, (Mar. 2001).
Dawkins et al., "Exclusion of serine palmitoyltransferase long chain base subunit 2 (SPTLC2) as a common cause for hereditary sensory neuropathy," *Neuromuscular Disorders*, www.elsevier.com/locate/nmd, vol. 23, pp. 656-658 (2002).
Gable, et al., Mutations in the Yeast LCBI and LCB2 Genes, Including Those Corresponding to the Hereditary Sensory Neuropathy Type I Mutations, Dominantly Incactivate Serine Palmitoyltransferase, *The Journal of Biological Chemistry*, vol. 277, No. 12, pp. 10194-101200 (Mar. 2002).
Houlden et al., Clinical, pathological and genetic characterization of hereditary sensory and autonomic neuropathy type I (HSAN), *Brain*, vol. 129, pp. 411-425 (2006).
Linn et al., Functional characterization of the promoter for the mouse SPTLC2 gene, which encodes subunit 2 of serine palmitoyltransgerase, *FEBS Letters*, vol. 580, pp. 6217-6223 (2006).
Monaghan et al., Mutations in the Lcb2p subunit of serine palmitoyltransferase eliminate the requirement for the TSC3 gene in *Saccharomyces cerevisiae*, Yeast, Published online in Wiley InterScience, vol. 19, pp. 659-670 (2002).
Rotthier et al., "Genes for hereditary sensory and autonomic neuropathies: a genotype-phenotype correlation," Brain, vol. 132. pp. 2699-2271 (2009).
Rotthier et al., Mutations in the SPTLC2 Subunit of Serine Palmitoyltransferase Cause Hereditary Sensory and Autonomic Neuropathy Type I, The American Journal of Human Genetics, vol. 87, pp. 513-522 (Oct. 8, 2010).
Rotthier et al., "Characterization of Two Mutations in the SPTLC I Subunit of Serine Palmitoyltransferase Associated with Hereditary Sensory and Autonomic Neuropathy Type I," Human Mutation, Mutation in Brief 32: E2211-E2225, dated Jan. 31, 2011.
XP-002665770, http://ibis.internal.epo.org/exam/dbfetch.jsp?id= GENESEQN:ABC43244, dated Feb. 21, 2002.
Ss48420144 (for rs34830263, dbSNP, NCBI, NLM, 2005).

* cited by examiner

*Primary Examiner* — Jehanne S Sitton
(74) *Attorney, Agent, or Firm* — Foley & Lardner LLP

(57) ABSTRACT

Described are methods and kits for identifying a subject at risk of, or having, a sensory neuropathy related disease, such as sensory neuropathies. In particular, the disclosure is based on the determination of mutations in the SPTLC2 gene causing sensory neuropathies.

6 Claims, 8 Drawing Sheets
Specification includes a Sequence Listing.

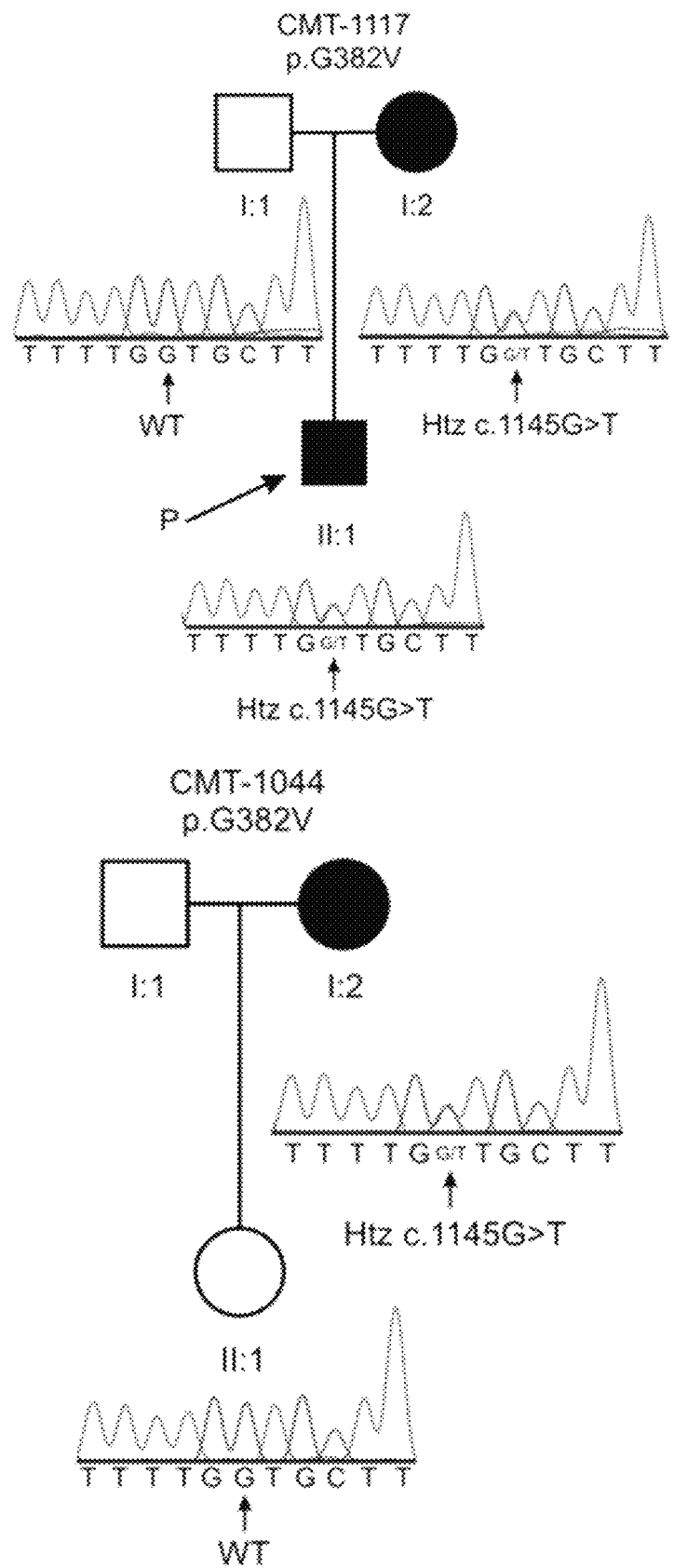

FIGURE 3A

```
Homo sapiens      SIGALGPTGRGVVEYFGLDPEDVDVMMGTFTKSFGASGGYIGGKKELIDY   397
Bos Taurus        SIGALGPTGRGVVDYFGLDPEDVDIMMGTFTKSFGASGGYIGGKKALIDY   397
Rattusnorvegicus  SIGALGPSGRGVVDYFGLDPEDVDVMMGTFTKSFGASGGYIGGKKELIDY   395
Musmusculus       SIGALGPSGRGVVDYFGLDPEDVDVMMGTFTKSFGASGGYIGGKKELIDY   395
Daniorerio        SIGALGPGGRGVVEYFGLDPRDVDIMMGTFTKSFGAAGGYIGGRKDLIDY   369
D. melanogaster   SVGAMGSRGRGVTDYFNVDPKEVDILMGTFTKSFGSAGGYLAGSKKLIDF   443
S. cerevisiae     SIGAMGPTGRGVCEIFGVDPKDVDILMGTFTKSFGAAGGYIAADQWIIDR   384
S. paucimobilis   SMGFFGPNGRGVYEAQGLEG-QIDFVVGTFSKSVGTVGGFVVSNHPKFEA   283

Homo sapiens      GFPATPIIESRARFCLSAAHTKEILDTALKEIDEVGDLLQLK-------Y   539
Bostaurus         GFPATPIIESRARFCLSAAHTRETLDTALKEIDEVGDLLHLK-------Y   539
Rattusnorvegicus  GFPATPIIESRARFCLSAAHTKEILDTALKEIDEVGDLLQLK-------Y   537
Musmusculus       GFPATPIIESRARFCLSAAHTKEILDTALKEIDEVGDLLQLK-------Y   537
Daniorerio        GFPATPIIESRARFCISAAHSKEMLDRALDVISEVGDLLQLK-------Y   511
D. melanogaster   GFPATPIMEGRIRFCLSAAHTREQLDFALEAIDEIADDLGLK-------Y   585
S. cerevisiae     AYPATPLIESRVRFCMSASLTKEDIDYLLRHVSEVGDKLNLKSHSGKSSY   533
S. paucimobilis   RPPATPAGTFLLRCSICAEHTPAQIQTVLGMFQAAGRAVGVIG-------   420
```

FIGURE 3B

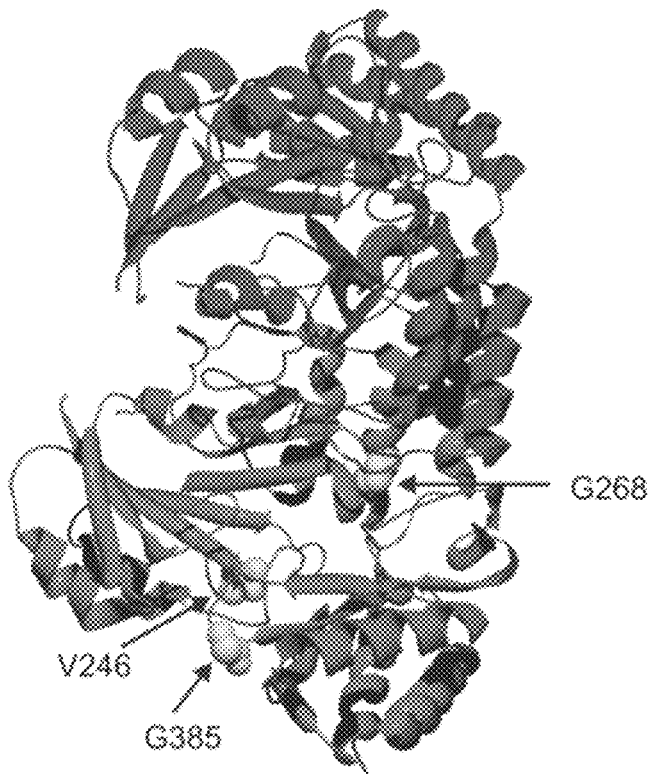

SEQUENCE LISTING

```
<160> NUMBER OF SEQ ID NOS: 88

<210> SEQ ID NO 1
<211> LENGTH: 109841
<212> TYPE: DNA
<213> ORGANISM: Homo sapiens

<400> SEQUENCE: 1
cttggccgag accggtcctc tgcggagagg gccccgccct ctgtgaaggc ccgcccggga      60
attggcggcg gcgctgcagc catttccggt ttcggggagg tgggtggggt gcggagcggg     120
acttggagca gccgccgccg ctgccaccgc ctacagagcc tgccttgcgc ctggtgctgc     180
caggaagatg cggccggagc ccggaggctg ctgctgccgc cgcacggtgc gggcgaatgg     240
ctgcgtggcg aacggggaag tacggaacgg gtacgtgagg agcagcgctg cagccgcagc     300
cgcagccgcc gccggccagg tacgagggc ccgcgcggcg gggccggggt ggcggtgtgg     360
actggcggag gggcggccgg gcggggcgag gtctccgggc catccgctgg gcaatccgcg     420
gggcgggcgc cgttcgcagg tgtgggcggc agtgtccggc cgctggcccg acctccacga     480
gcctggaggc tcaaggacgg ctcggggct ccccacctct ccgcgcctgg aggtcttact      540
cccggagctc tggggttctgc tcagagctcc gggtactttt ctctgcccca ttctgccaga    600
agtgtgtgct gtccccaggg gaagcgatga ggggcccttc ggactccagt gggagccgcc     660
caagggctcc ggagggtccc ttctcaaacc cctgaggtta ttgcttcctt ttaaagtcct     720
gcagtcgtcc aaagaaaacc acccatgggg tccttaagaa gcaaagaaaa ttaggcggtg     780
gtgtcagatg gaaacacacc cagcctctcc caaccacatt ctggactacc acgttcagtc     840
cccaaccagg acattggtcc atagatctgg cagggaatcc aagctggtcc ctcgaaagca     900
tcattctctt aactctgccg gtggtgagac tctaccccag gctccaggtt ggattaggtg     960
gccccttcga ccctttcctg aacacgagtg ctatcacaca aggggattgt ttagcctggt    1020
ggtgacttgc gatgactcta tactaattaa ccatgctgaa tcatcaacca agttcaggca    1080
gttctaaaat attttgaaaa gttctaaatt caagacaatg cttattatca accttacagt    1140
ggtctggact gacagatatt ctgttgaaat gtgttttaa agatgagctg gttaaaaaga     1200
tgcaagatcg gtgttcctgg aagagagtgt tgcgataatt ttgcagttga ctttaatacg    1260
tttaagtctt gtacagatat taaggaacgc ttagaaagta ctctgtttcc ctttagcggg    1320
agtgtgactg ttgcagtttg ataggatggt gatcttaatt tggctttaac ataactactc    1380
```

```
cccagatgag tagttatgat ggataggtct gttactgttt gctgcgaagc agaaaataaa    1440 gcattttttcc aggtcatgtt gagatattga gactgagttg aggggaaaaa taagtaaagc    1500
agacttgacc tccccctgaag ttgtaaggtg tcaaagcgaa gtaatacaca gatcaaaaga   1560
tttgttttca cttttaaaga aataattgtg tgagggagga agtgataaca gtcagctcat    1620
tataagcagt ggaatagttt gtcgttttcc tagcaatgta aacgacttat aagacaaaat    1680
tgttgtggta tagaatgtaa tagggaaatt taacgggtag gagttagaaa atacatttgc    1740
aggtgaattt cattgaggta tgattttttt tttgttttg ttttgtttt ttttttcag       1800 acagttttgc tcttgtcacc caggctggag tgcaatggcg cgatctcggc tcactgcagc    1860 ctccacccc tgggttcaag cgattctcct gccccagcct cccgagtagc tgggattaca    1920
ggcgcccgtc atcacgcccg ctaaatttt gtattttat tagagatggg gtttcaccat      1980
gttggccagg ttggtctcga actcctgacc tcaggtgatt ggcctgcctt ggcctccaaa    2040
agtgctggga ttacaggcgc accaggccga ggtatgattt tttttgtttt tttggttttt    2100
tttgagatgg agtctcgctc tgtcgcccag gctgagtgc agtggcgcga tctcggctca    2160
ctgcaagctc tacctcccag gttcacgcca ttctcctgcc tcagcctccc aagtagctgg    2220
gcctacaggc acccgccacc acgcccggct aattttttgt attttagta gatacggggt    2280 ttcactgtgt tagccaggat ggtcttgatt tcctgacctc gtgatccgcc tgcctcggcc    2340
tcccagagtg ctgggattac gggtgtgagc cactgcacct ggccggtatg atttttaaa    2400 atgaaaaagg aagtcaagag aaaggtgttc acacttcagc gttgctttgt gttcaaatgc    2460
ttctttcaat ccctatgagt tatgttcaga tttagtagga aatcaaggac ctttctccca    2520
taatctctaa caatttagca tttatagaat gatatttctt cagagcttgc caactaataa    2580
ggtgaagaaa tatcaaggta ctaacatgac attttaaaat ctgtatgaat aacatttggt    2640
tgacttttgg ggacatgttt tgtaaaagtt tcactcaagg cacattggtg gcatttggaa    2700
gaacggtctg ttggaatgct gtgagggctg cagtatccct tctagaaaac tacttctcac    2760 cagtatttt aatacagact tcagatctgg agctttctac actctcagat ggaggaatat    2820
tgtctgtgaa tattttttctt tcttatacaa aagagagatc ttggtaacta catgagagca    2880
atacaatatc ttaacatttt ttaaaagttg ttttcatttt taattaaagc gatgtgcttg    2940
tgctccaacc tctacctatc ttcccctct ttctgggggg gaaatgttgc caactgtgcc     3000
atcaaaaata cgcatacagc tgtgtgtcat gcttttacta aaatatgaat ttagagtata    3060
acattgttga gatgtaaatt cttttcctca catctcccac catgtctttt aatgaacagg    3120
agagaagtca gaaacgtcta ggatcacttt acactctcaa gagtatgttt ctgtgcttga    3180
agagatgaat gaatgtgtat agtaaaagaa caactcttgg atttgggttt agaatttgat    3240
gagctagatg ctgtgttaag gagttatgaa acaatcacac attgctgttt agtgatgaca    3300
gtagacacac agttttcaca atagtaacag ttgaacaata gagcagtaat ttttcctctc    3360
tgctattcag atgagtggga ggagcacaaa cctttatttg aggtaaggtg tggcaatttg    3420
cccgagggaa acttttacat tagcattgga aagaaccttt gggagtttat ttaattcagt    3480
cctttatctc tttgtaggag tttattaaaa tcagtcttga tagaaaattc tgtactgttt    3540
ttaaagatct ccaggggatt tgcagcaagt ttttctctat agcaaattgg attattattc    3600
catgatctta attaccaaat ttcttccctgt ggatttaaca tttgatgaaa taaatgccat    3660
gttttggttg cacctgaaat atagtagttt gtttgtgtgt ttgttttaa aacttcacgt    3720 taacagctct ttttaaaaga gcttccattt ctttatagaa gttttgagat ttaggttttc    3780
```

```
cttttacttt cctgagttag ttaataagtg tgaaagaaaa aaagttatct acctttgaga    3840
cagttttgac cctaactttt ttcccttagg gtgtagtttt aatgagatat tagaaggatg    3900
agagctctct ggcttacaga ataaaaaatt ctatctcaag gaattggggc aaaagttgtg    3960
ttcttatgtt aaataataag caaagtagaa agaacaaagt gttagtcttg cttcttagga    4020
ggaggcaaat aaataactaa taaagctggt ttactaaata gctactagct tttgtttcca    4080
ctgagggaga aacagtaact gggggtttat atgtgatagt taaggaaaag gagacgatag    4140
ttatgaggct agaacagtag aaatagttag aatagtcata tatctattta gatttagcag    4200
atcctgataa gatacctcag atacctgaag gcttttcaga ataatgtaa tttacaactt    4260 ggaggacaag atttttcattt cagttttcac tctaagggga agcatatctt gattcttaca    4320
tagctgcatc tgaagaattc cagagttatt tgagatactc aggaattttc tttaacagga    4380
attcttggga aatgtgtaag cagctatgtt cttaagatag tattttagaa ctaggatgtt    4440
cagaaaagtc agacttgccc acttttttagg gtttgcccat gtgccataga aatttgcacc    4500
gctttgagca agacagttaa ttggttgatt taattagatt cagttttttgg aagaaagaag    4560 cagtgtttat tggtagaata ggcaattcag agggatgggg agaggcactg tttgcattct    4620
gagtgggtgt gccatacttg attaaataaa tggttgtgg actcaaagtc agttcccttc    4680
tgggtagttt ctgagaagct tctgtaatat aattcacaat ttgtgaccga taaaaaagta    4740
agtcctttgc tcttgaccca tttactgtta gaaaatttat cttaagtttg tctttaagac    4800
tactttttat tgcaaagctt gaggcagcta ttcttccttt ttttaaaaaaa taatttttac    4860 ttctcattat agaaataata catgtttaat gtgggatcat aaaacattga gataatctct    4920
gcgttaggtt tttttttttt tgagacggag tctcactctg tcgcccaggc tggagtgcag    4980
tggcgccatc tcagttcact gcagcctcca cctcccgggt tcaagcgatt ctccagcctc    5040
agcctcctga gtagctggga ttacaggcat gcgccaccac gcctggctga ttttttgcatt    5100 tgtagtagag acaaggtttc acagtgttgg ccaggctggt ctcgaactcc tgacctcagg    5160
tgatccacct gcctccgcct cccaaagtgc tgggattaca ggcgtgagcc accgcgccta    5220
gccggaggtt tgttttttaa tgtggtctat tgtaaatcca tctgctactt tccgttaatt    5280
tcttttcttt ctttttttttt tttttttttg cgagataggg tctcgctcca gcctggcctg    5340
cagtagcaca gtcatagctt actgcggcct caacttctcg ggctcaagcg atcctcccat    5400
ctcagcctcc caagtagctg ggtccacagg tgtgcaccac tacagtgggc taatttttttt    5460 ttttgagaca gagtcttgct ctgtcaccca ggctggagtg cagtggcgcg atcttggctc    5520
actgcaagct ctacttccca ggttcacacc attctcctgc ctcagcctcc cgagtagctg    5580
ggactacagg tgctcaccaa cacacccggc taatttttttt tttttttttg tattttttagt    5640 agagacaggg tttccccatg ttagccagga tggtctcgct ctcctgacct tgtaatccgc    5700
ctgcctcagt ctcccaaagt gctggaatta caggcttgag ccaccatgcc tggccttttt    5760
tttttttttt ttttgtagag atgggtctta ctatgttccc caggctagtc tctttttttac    5820 ttaaacaaac aaacaaaaat aaataaaaat atatatatat aaagagagag ggagacagag    5880
agagagggag acagagtctc actatgttgc ccaggctgat ctcaaactgt tgggtacaat    5940
cgatcctcct gccttggcct cctgaagtgc tgagattata ggtgtgagcc accgcaccca    6000
gccacccagg ctggtctcag actcctgacc acaagcatcc tcctgcttca gcctaccaaa    6060
gtgctgggat tacagccact gtagcagact attttgtgat aatttctaag tacagtgaaa    6120
```

```
tatgcggttg tactgatact atgggtgtga tccagtctta ctccaaaaaa taggtattaa    6180
gggctgggca cagtggctca tacctgtaat cccagcacta agggaagcca aggtgtaagg    6240
attgcttgag cccaggagtt caagatcagc ctgggcaacg tggcgagacc ccatctctat    6300
ttaattaaaa aataataagg tatatgacca ggtaccgtgg ctcacgcctg taatcccagc    6360
actttgggaa gccgagatgg gcggatcact tgaggtcagg agtttgagac cagcctggcc    6420
aacatggtga aacccgtctc tactaaaaa tgtaaaaatt agccgggtgt ggtggtgtgt    6480
gcctataatc ccagctactc tgggagtctg aggtagtaga atcgcttgaa cccaggaggt    6540
ggaagttgca gtgagccaag atggtgccac tgcacttcag cttgggcgac agtgagactc    6600
tgtctcaaca aacaaaaca aaacaaaacc tcagttagat accatttcac accactagga    6660
ttgctaaaat aataaccag gtattaagtg ttcatgagga tatagagaaa ttagaatcct    6720
gatacattgc tggtgggatt ataaaatgat gcagccactt taggaaacag ttaaacatag    6780
agttagcatg tggcccagta attctactcc caagaaaaat gaaacatatg ttcctgcaga    6840
aacttgtata ttaattataa tagcagcatt gttgattgat tgattgattg attcagggtg    6900
ttactgttac ccaggctggc aggacatggc tcaccgcagc ctccacctcc tgggctcaat    6960
caatcctccc acctcagcct cccaagtatc tgggactgca ggcatatgcc accatgagtg    7020
gcaaaatttt ttttttttg agacagagtc tcactccgtt gcccaggctg gggtgcagtg    7080
tggctcactg caacctccac cccactggtt caagcagttc tcctgcctcc gccttccgag    7140
tagctgggac tacaggcaca tgccaccacg cccagctaat ttttatatt tttagtagag    7200
atggggtttc accatgttgg tcaggctggt ctcagactcc tgacctaagt gatccatccg    7260
cttcggactt ccaaagtgct ggaattacag gcgtgaacca ctgtgtctag ccccacgtta    7320
tttataatag ccaaaaagta gaaacaatcc aaatgtctat caactgatga gtagataaaa    7380
tatggtatat ccatataaaa ggatattatt cagcaatact actgaaggaa tgcagtacta    7440
atacatgcag gagaatacta cattgtttat ggccatgtgt ttatatagtg aaagtattta    7500
aaaatacagg ggaatgataa acaccaaatt cccaattctt ctgaggagga aaggaaatat    7560
agcatttccc caggacagac ttcttaaaag gattggagaa ctacttaaac atgtcagatc    7620
ttgacactgt cctgatggcc tcctgtcact aataacagaa tacaaaatgg ggtttacaag    7680
gcccaccatg aactttccca tccctctctg acttcatatc ctgccaggtc actgctttct    7740
agccaatccg ggctttctga tgttccccaa acacattgcc atcaagcacc cctccctggg    7800
gccttattat tattattatt attattatta ttattattat tattattttg agatggagcc    7860
tcaatctgtc acccaggctg gagtgcagtg atgtgatctc ggctcactgc aacctccgcc    7920
tccaagttca aatgattctc ctgtctcagc ctcccaaagt gctggaatta caggcgtgac    7980
ctaccacgcc tggggtccct ggggctttag cctttacagt tacctcagcc tggaaagctt    8040
tttcacagag ttctcttccc tactccaagt ccatctgctt acaccttacc tccaccctgt    8100
ttaaaatgct cttttccac gatttattc tgattgtagc agtgtgatct gatacagtat    8160
atctatttgc ttatctgttg tctgcctctc tcacaggagt gtatttctag tgctcagatc    8220
atgcctagct catagcaggg actcaataag tattgaatga ataactttaa tgttttattt    8280
aatggaaaaa agatctaaag catataagct aaatcttaag ttttgataaa gctagatgtt    8340
gaatacagtt ttatttctat ttttttgatg ataattactg tgtcatattt catacatact    8400
ctgctggtta acaaaaacta gctccctaaa ataatgttac agacataagt aagaaatgga    8460
ttgtggtgac acataagctg ttaaagaaac ccgtagccta atttatagtg tatcaggttt    8520
```

```
gcaagtggtt taaaacaata gcggtttact gaatgttctt actagcgtga ggggagagct    8580
tgtgagaagt aggaagaggc cagagaaggt cctggggtct ggcacactct gatatgcttc    8640
atcacctctc cctaagctct ccctacaggg cagtggggcc agtggtgact tttgcggcac    8700
cctctccatt gtcttaccaa gggcttcagc tgtgagacgc cggttggtgc tacaaggaag    8760
gggaaacgtg tcagctcttt cctctgctct tttctcacat tgatttcaaa tgccaagaag    8820
ctgggctgag aaaccgggct tgtgatcctg gttgtactgc agtccaccat gtgctggaga    8880
gctctgcagg ttgtgctaaa gggtagtgtc tttattgcct cctgtataag cttgactttt    8940
acataggcaa gcaggttatt tccaggacaa ctaaattagt tggtgcgaaa cctcatttcc    9000
tagaaaccca ttttcttagt agaggaaacc catataacca tttgtctcca tgtaagtgta    9060
gctaataaca tgaataacaa aaatagctaa ttatttaaat agcaaaaata agtatggaag    9120
atgaatttgc agtaaaattc taatattaag ccactgatta ttttaaaaca atcagattaa    9180
gttgtagtac ctctgaaata attaaaggaa aatttgattc ttagaaaatc tcaattcatt    9240
ggaaagccat ggaattaata aaataaaaaa agaaaatctc aggcaatata aactaaggaa    9300
tggcaaatgg aaaatgtatt gattggtgga aaagtaattg cggttttga cattgaaagt    9360 aattactttt gccattactt ttaatggcgg aaaccattta atggcaatta cttttgcacc    9420
aacctataaa taattggact ctagttccaa ctttgatatt tagctttccc atgactgttg    9480
acaaattgct taatctactt tccttgattt tgtcagtcaa atgaggagga agagacagct    9540
tgagaaacat ttgtaagaga aatgcttatt actttgtatg tgtttttcgt cttacatatt    9600
aaatataaat tcctttaggt gatattcttt aaaatgattt ccttacttcc ttttatattt    9660
acatccattt tctcttaaaa aaacaaacaa acaaaatact gcacaattct tgaagacaag    9720
gattacctct tacctcttat ttgtttcatg aaatatagag tacaattttt ttttttttg    9780 agatgggtct tgttctatca cccaggctgg agtgcagtgg cgccatcatg gctcactgca    9840
gcttcaacct tctgggctca ggagatcctc ctatctcagc ctccccagta gctgggacta    9900
cattcatgca ccaccacatc cggctaactt ttgaaaatgt tgtgtagaga tagggtttca    9960
ctatgttgtc caggctggtt ttaaactcct gggtccaagc aatcctcccg ccttggcctc   10020
ccaaagtgtt gggattacag gcgtgagctc ctgtgcccag cctagagtac agttcttgac   10080
atatagatag aaattaagta tttgtagaat gagtggaaaa aaaatgaaa tgattatgtt   10140 gattttgagt ttctcggtgg aatagggctt tggattccta aagagactt taatgttgaa   10200 aaattatttt tgtagttttg aaaatgttaa aaaattgaac atgagaaatc tccacttctc   10260
tgggcatgtg aaattaaagg gagggatgat caagttgtga gagattccct aggccagcag   10320
tgctgatgca agaaggtgaa catgtagact gctgtattct gtacacacac acacacacac   10380
acacacacac acagtcccct ccctcctggg aaagcaaaag ttgttgttgt ttttgagac   10440 agagtctcgc tctgttgccc aggctggagt gcagtggcac gcggttttgg ctcactgcaa   10500
cctttgcctc ctgggttcaa gcggctctcc tgcctcagcc tccccagtag ctgggattat   10560
gggcgtgcgc caccatgcct ggcaaatttt tgtattttca gtagagagag gtttcacca   10620 tgttggtcag gctggtctcg aagtcctgac ctcatgatca gcctgcctcg gcctcccaaa   10680
atgctggaac tacagacgtg agccactgcg ccaggcagca gaagttttg acgatttcta   10740 gacaatgtgt gtaaagacct ttagagtcta aagttaatgt ttgcatttg cagtcttagg   10800 cagatacaat gaggtataaa acacctctat ccaaacaact gagttggact gggctgaaga   10860
```

-continued

```
tttaagtcct tcagttcggt gtagtatccc aagagtggga tccgttgtat gtttgttaca    10920
ggccactccc tctagcttta tctgctaagc actgtgagat tgtgcttaat ttcactttgg    10980
ttttctagtt caggcctcca gcctggaggt gaatgtcctg tgtagaaaac tggccataaa    11040
tttagggctg ttatgaaatt tagtctgtca tgccaaccca tatagctgtc ataagttctg    11100
ctggtttttc tttctcttga tggagttctg cctatggcaa gccccagtta tcatcactca    11160
cgctaaagct ctacaagtac cacaagtaga gagaggaaat ggctggcact ttcagctcac    11220
ctagagaggc ctcttctccc tctggaattt taattctgct agtcctcttt gctatgcata    11280
gaagacagct cttcaatctt taaagccatt tatttatttg aataatctat ttagttttat    11340
ctagttgtta ctgtgaaagc actagcttgc ctctctctat taaagctaac ctggaagtct    11400
cattatttt tgaatttttg ttgccacaaa catgacataa gaataagttt gttctgggcc    11460
aggcatggtg gcttatgcct gcaattccag cactttggaa ggccaaactg ggaggattcc    11520
ttgaggccag gagttcaaga ccagcctggg caacataggg aaacctcatc taaaaaaaaa    11580
aaaaaattaa ccaggtatgg tggcgggcac ttgtatagtc tcagctactc tggaggctga    11640
agtgagagga ttcatgagcc caggagtttt gaggttacag tgagctatgg ttacgccact    11700
ctactccagc ttgggcagca acagagtgag accctgtctc tttaaaataa ataaataggc    11760
caaatgttta aagtagaaag tcaaagtggc cagccattcc actacaagat aaccagtgtt    11820
ttcagtttga tttatagctt tccagattag catgtgtgtg catgactttg tcattttacc    11880
tttttttttt tttttttttt gagaaagagt cttgcttttt tgcccaggcc ggaatgtggt    11940
tgcaggatct tgactcaccg caactccgc ctcccaggtt caagcaattc tcctgcctca    12000
gcctcccgag tagctgggat tacaggcatg caccaccacg cccggctaat tttgtatttt    12060
tagtagaaat gggggtttctc catgttggtc aggctggtct caaactcctg acctcaggtg    12120
atccgcccgc cttggcctcc caaagtgcta gtattacagg tgtgagccac cgcatctggc    12180
cgggaaatat ttttaaaa tttcttgaag cccttaaagt ttacaggctc tgctaacatg    12240
ataaataccc aataaaata tagaaagaa attctaagag atttaatat agaatcatta    12300
tctgttaact gttttagttg agagcaacag aaactgagtc tggttaaact aagcaaagag    12360
tgatttattg gaaggatgat aggtatacaa aaatgggatg ggggatgaaa ttgaacaagt    12420
ctcagaaagg caggaattgg cacagctctt gggacctcag tggcaggagt ttgtgaaccc    12480
tttcttcagg acattggaga cccactgccc ttcagactct ctccccattg acattttaaa    12540
tccccataaa agagggttgt tggatttctt tcggcagagg tgtctgtgct gcatcaatca    12600
gttatggtcc aggaaatata gtcacaacaa agcatacacg tgaccaccag gggcgcatcc    12660
ctgcatatca gggagtattc ccagagaagg gaagttgaca caaaccggat tgcctctcca    12720
gtggtgtgca ccacaaaacc agactggagc acgtggtggg ggcagagtgg agggaatggt    12780
attacaggct cagaacgtgt cagcagtgga ggagaactca gatgaagatg cagaatttgt    12840
ggcagagctg cacttgtact ccagtcttca ggctcttgca tctcttacac cgtgatgctt    12900
atctagagat ggaaaagtgt tacagcggag gcttgggtgg ccagtgtgat aactcctggg    12960
cagacatcag tgcccagtgt gtacaggatg ccactgaact gaaatggaaa tgttccactc    13020
catatatgct tgaagatctc cttttgggg tttcaatag caaaatggta atgtcaaaat    13080
ataaatgtgt ttcacagcta gttttggaaa catttttcat tccattccac atgagatact    13140
tactgacaaa aactaaggaa tttatgctgc ctacacgaaa aactatggac ttctacttt    13200
cagaatttcc ctgctgaaaa aaggagacac ttctggacat acacattcag agcacagtat    13260
```

```
agcctatgtg atttgtgtaa agctccaaac tgttctctct agtatgtgtg atatgcagta   13320
gggagaggcc agtacatttc agtaaaattg caaggacagt ttcagcagaa ctgattttaa   13380
ggagcaacag aaacatagca cttgaaaatg aatagggttc gtttaatgga caaagcatga   13440
taacagttct ttgattgctg aagaataatg ggtggttcac attagacatt aagttttta   13500 aaataaagtt ccaaaccatt caccagctgg gcaggttctg ttatcctgct gtagcatgca   13560 gctgaatgt gcttatttgc ttaaggaaat tatgcttttg tgattttgta ttcatatcag   13620
aaatgtgtgc ttctgtttcc taataattac ttcactgtta ttggattata acatagttac   13680
tccctgtcct ttcatgggat tcttgaaacc tttattcagg atcatttctt ctgagtcagt   13740
ttacagtgca ataaaaactg ttttatttta attatttta aaaaattttc ctgaaactta   13800
agagacagaa ggcaacatat aatccagggt tttcttttgc tatagaggat atcattagga   13860
cgtttgacaa aatctgaata aacttgtaga ctaggctggg cacagtggct catgcctgta   13920
atcccagcag tttgagagac caaggcagga ggatagcttg agcccaggag tttgagacca   13980
gcctgggcaa tgtagtgaaa tcccatctct acaataaatc agtaaatatt tattgtatta   14040
atcttatgtt atcttatgtt aatctcttat tgtgctgtgg tcccagcttc ctgggaggct   14100
gaggccggag gatcacttaa gcctgaaagg tagaggctgc agtaagccat gatcacacca   14160
ctgcactcca tcctgggtgg cagagtgaga tgctgtcaat agaaaaaaaa aaaaaaaga   14220 aacaaacctt ttcaacctcc ttaaaattct ctcgtgcccc acaggaagct cttggactaa   14280
agcacagaaa gtcattacta attctatctg gaagccagaa aataaggtgg agccaaagat   14340
gactccaaac ttgggagact gggtagactg gatggtgatg ctgttgacca aaataggtaa   14400
tagaagagga gtatcaggtt ttaactgaga gggagggtta ggatggtgag aagaagttca   14460
gctttagact tgttgagttt gaggtgccca tgaagtctaa gtggagctat gtagaaggca   14520
ggtggaaatg cgaatgtgga gttctggaaa ggaatttggg attgcagtgt agacttgagc   14580
ttacttgtag catctgaggt ctagctgaga actcctaagt agatgagaat tcactagaga   14640
ggctatagat aggcaagttt aaagagaagg gtagagacac ggagaagggg gttgggagc   14700 agccaaagca ggcgtccccg cagttgactt gccaccaagg gaatgtgggt gaatgaccaa   14760
ggcaggcgtc cccatggaga tcagacacca aaggaacgtg ggtgaataat cagagaggca   14820
tccctgcaat gattaaacac caaggggaagg ctgccttccc gagtccgtga ccggcaccgg   14880
agttttgggt ccacggataa aatgtgtctc ctttgtctct atcagaaaat gaaaggaatt   14940
gaaattaaga gaagggagag attgaagggt ggcgccaaga ttgaaaggag aaagaggttg   15000
agggatagtg agagaggttg gagaaaagag taaaagaggg ccgcttaccc gatttaaaat   15060
cggtgagatg ttccttgggc tggttggtct gaggacctga ggttgtaggt agatctcttc   15120
acgaagtgag gatgaggaca ggggactggt ctcccgaagg agtcccgctg accctggtct   15180
ttggcaccaa atgtttcacg tgtgcatgtg aagagacccc cccaaacagg ctttgtgtga   15240
gcaacaaggc tgtttatttc acctgggtgc tagtgggctg agtccaaaaa aggagtcagc   15300
aaagggcggg aattatcatt agttcttata ggttttggga taggcggtgg agttaggagc   15360
aatgttttgc aggcagcggg tggatctcac aaagtacatt gtcaagggtg gggagaatta   15420
taaagaacct tcttaagggt gggggagatt acaaagtaca ttgatcggtt agggtggggc   15480
agaaacaaat cacaatgatg gaatgtcatc agttaaggct attttcattt cttttgtgga   15540
tcttcagttg cttcaggcca gctagatgta tacgtgcagg tcactgggga tatgatggct   15600
```

```
tagcttgggc tcagaggcct gacaatatat actcgtaaaa aacaagaaaa gaaaaatcaa    15660
agcagtttag aaggttataa acaaaaaata tgccatcttg tcccacccta ctccttacca    15720
cattttcttg tgtctccttc gagacaattt tagtcttatg gaaacatatg tattacacat    15780
atggcttatc ttttattata ctttcccatt attgctttgg ttaggagtgc cttttcagct    15840
gcttaataaa catggttgac agcccacagg catgtggaca aaatggccca ttagattgat    15900
tttttttcct tctcttgttc tgtaatgtgt tttatgatgg tgtgcttata gtcttgtcgg    15960
aaaaaatttt cttcctttgc attttattt tcttttacat tttcttaaac agtaatatta    16020
ctgttcaagc aaacatttct tgatattcct aaatctttcc ttgattaata atgctaatat    16080
agtgtcacat tcttgtttgc ttaatgtgaa cagactgtga acagactgat acgaaatgtt    16140
attaagtgtt aactatttat taagacttca taaatactac cctgggtgct agacgtgcaa    16200
taatgagcaa aacagacctg tgttttttcc tcatggatta ttacctatgt ataagagagt    16260
aataccatta ttgtttgaat catgtgaaag ataagattta gcatcagttc ttaaaggtga    16320
agtgattttg ttctctcaga gtttaaagac ttttcacctt ggagaggctc gcgtgtcagt    16380
tggcgtgccc atctgcctcc ctgtatcatc agtcactctg ttttgacaga agccacattc    16440
caaagtcact tcttttcaca ggttctgaag gtggaaaaaa agaaacccca gccacttcct    16500
agttgaacct aaattcttta aaatacattt aatttttgaat aaggctttgg taaaatcaca    16560
cagttcttca taatggttta gcatcctcct tcctagagag tccagcctac agtatgaatt    16620
gacctgatcc tgcctgtgtg ggtgtgcctg aaatcaaggc ggatatcttt aaaagagacc    16680
cacccatagc attcctgacc tgtaaactcg ctgcatgttg gattgagact gcggtgggg    16740 ggctctgtaa tttccaggct ttttaatgat gtgtacagtt gagagtaaat agtttaaata    16800
atttcatagt tagggagagt tcagcactgg tattaaacag agttcttaag gcaaatatt    16860 ttcagataca gttcttaaag agatgatcag aatgttaatt tttcttgtct tttaaattgc    16920
ttttcatttt gctttgccca gcttaataac ttttttatat tgttatgttg ttaattttta    16980
aacaattttc tgccttaaga tattggctca attttaggta ttctgttcta aacacattac    17040
agtcttactc ccatttaaaa gtttaagtat taaatattga caccaaactt tttctgctgt    17100
gtggaagaga ttgatgaaga cccaaatgag tttgtgaata gttttcagaa gttatttaga    17160
tcatcaagtt gaatcagtac caacagattc catccatctt ccatgcctat ctgaatgcct    17220
gtcctttgtc acatacaact gtgtcttcc gaactattcc agtctgtaac actgaagcag    17280 cttttccaaaa ctaacattac ggggatagga tattctaaaa tatctttacc ccttggatat    17340
gtataacaat tgattgtata gttatgtaaa ttttattaat ttgttttat ttgtttatat    17400 cgtatctctg atcagattgc ctgagagggc aagaaaggat ctttagttc tttgggacct    17460 tttgtaatgc ttaattgacg atatgcccct ggtaaatttt gtttaaccat cctcactgca    17520
gttgttccaa agttaagatt aaagttaaca cacaaacttg tctagcagat atcttctata    17580
aagcaagatt tccattaaaa ttgaccaaga agcaaaaagt tttcatctat gagatcaaaa    17640
gtaaagtagc ttggtttttg tgtattaaaa tccaagtatc ccaaaggtta aaacaaggga    17700
taatcttacg atgtttggga atgaatactt aagatgaagg gggacagaaa aattcatgtc    17760
agttactaac aatttttccc cttgtttgg gtttcacttt ctttttactt ttatataatg    17820
ctgggccaca cttttttttt tttttctgt atcacctagg ctgtagggaa gtggcatgat    17880
catggctcac tgccatctcg accttctggg ctcaggtgat cctcccacct atctcctgag    17940
gacctgggac tacaggcatg tgccaccatg tccagctagt gttttgtttt tttgttttg    18000
```

```
tagaggcaag attttgccat gtgcccaggc tggtctcaaa ctcctgggct caagttatct    18060
gcccaccttg gcctcccaaa gtgctaggat tacaggcatg cgccactgca cccagcctgg    18120
accacactta tataaacatc ttagttttt gcatgattta cttgtgttat cactaccaac    18180
aaaggttaat ttgaactacg tgtttctgca ggggcctact gctgataatt atttggaata    18240
ctatggctgg gtggctttaa gaatgtgtgg tagtaaaaca tttacaaata ttttacattc    18300
taataaagct gaatttactt ttgaactttt gatctcttca tctgtaggcc aatatagtac    18360
ttttttggga caggctttct ctttgttgat ttatatttt tgcttttt attagaacaa    18420 aagaaattat gctagcattt tagaatctat ttaagaaaat caaataatga taaaaatcag    18480
tgttaggtgg tgttcttatg cagtccttct tgctccct ctttactgt tcatctgaag    18540 ggcatataat ttataagtta tttcattga aaacaagtag ccctgcttat ctcttagtgt    18600
tagatttgac tgttgcttac aaaattcttt tttttttt ttttgagatg gggtttcgct    18660
cttatttccc aggctggagt gcaatggctt gatctcggct ccccacaact tccatctcca    18720
aggttcaagc aattctcctg cctcagcctc ctgaatagct gagattatag gcatgcgcca    18780
ccacacccac ctagttttgt attttagta gagatgggt ttctccatgt gatcaggctg    18840
ggcttgaact cccaacctca ggtgattcgt ccgcctcggc ctcccaaagt gctgggatta    18900
taggcgtgag ccaccgtgcc tggcctaaaa ttctttttt tttttttctt gtttccagtg    18960
aggttggaac ttagaaaatt ccttttttt tttgacacgg agtcttgctc tgtcacccag    19020
gcaggagtgc agtggcgtga tcttggctta ctgcagcctc cacttcccag attcaagcaa    19080
ctctcctccc tcagcctccc aagtagctgg gattagaggt gtgcaccacc aatcctggct    19140
aatatttgca ttttagtag agacaggttt caccatgttg accaggctgg tcttgaactc    19200
ctgacctcaa gtgatctgcc cgcctcagcc tcccaaagtg ctgggattac aggtgtgagc    19260
cagtgcgccc ggcggaactt agaaaattct taaggtataa ttcagcaaat ctctaaggac    19320
ctagatttta ggtaggaatg ttttcttgc catgatggaa ataaacattt ttaacctctc    19380
ttttagatcc atcatgttac acaaaatgga ggactatata aaagaccgtt taatgaagct    19440
tttgaagaaa caccaatgct ggttgctgtg ctcacgtatg tggggtatgg cgtactcacc    19500
ctctttggat atcttcgaga tttcttgagg tattggagaa ttgaaaagtg tcaccatgca    19560 acagaaaagag aagaacaaaa ggtaactgtt agagagtttt tgattctgta aatagaagcc    19620
ttttatggaa atcttagtat ttttgcacaa aagcttttc tcagaaattt gggtacacat    19680
taaaattaaa ctattccaga tgcagttaaa tgaaaacatt ctacaaagaa agctgaaaaa    19740
taacaaggtt aaagatatca aagcattcat catgggttta atcaagaaga acctaaggag    19800
gtgggcggca ctatccctgt tttatggatt agaaatcaaa aagtcacaag ttaaacaacg    19860
tttcccaaga tgccaggtgt cagagctgct gtgtggacag aggactgtga agtgaaaaag    19920
ccttgctctt tctgttcata ccagcatgct gaatcccagg ttgtgtttac cattttctga    19980
aaaggttgta ttctttggaa ttaataatgt gttttctcat agatacatta tacatagttg    20040
ggtgattcac acatcagctc ctctccccag acaaacaagc tgtaatacag aatgtggcca    20100
accgattcta tttacggtaa acaacactct tgttttagga atggcaaaca tatgagcatg    20160
gttgtctggg gaagagggct tcttcattca cttcactttt ctctgcatgt tcctttgtac    20220
ctctgaaggg ttttttgttt gtttgttgt ttgtttattt tttgagacag agtctcgctt    20280
tgtcaaccca ggctggagtg cagtggtgcg atctcggctc actgcaagct ctgcctcctg    20340
```

```
ggttcacacc attcttctgc ctcagcctcc caagtagctg ggactacagg cacctgccac   20400
cacgcccggc taattttttt tttttttttg agacaagtct tgctctgtcg cccaggctgg   20460
agtgcagtgg ctcggtctcg gctcactgca agctccgcct cccgggttca ccattctc     20520 tggcctcagc ctccccagta tctgggacta caggtgcctg ccaccgtgcc cggctaattt   20580 ttttgtgtt tttagtagag acggggtttt actgtgttag ccaggatggt ctcaatctcc    20640
tgaccttgtg atccacccac ctcggcctcc caaagtgctg ggattacagg tgtgaaccac   20700
tgtgcctggc cagttttttt gttttttta cttgttattg acttgaagct cacttctgga    20760
gttgtataca ttacatatgt gttacctagt ctccataaat aaataaaatg agggttaaag   20820
atgcctaatt ttactaaaaa taaaacaaac ctgtgtgttc ttggcatgtc ccacatggca   20880
aaaggttgtc ttttagccca ggcaaatgta ccagattaga gaaggactta agacattaga   20940
gtttttttgt ggttcctgtg cgtccgagga aaagaggcag gtgtggggtg agcaaagtca   21000
acgctgagac gagccagtga acattgattg tagaagaaac aattattcag gtaatggata   21060
gtggtcatgt gcaaatggga agagtatatc acgaaaacat tgtcagttac taggaagaca   21120
aaaccagtca gtagatacat ggattcaaaa gtggctcctg ggagaactca agattaggca   21180
tcctttctct ctcatctcaa ccatcttgta ctccatccga gccccagcac aagttggcca   21240
tcctactcat tgccctgcaa gttaatttca caaagaaggt aaataagttt tttgaatgca   21300
aagccctgca ttcagaagtt ggtccagtaa ccctaagtaa tttttatctt ttaaaaccca   21360
aacacatttt taacatttt tatttttatta tcattatttt ttagacaaga gtctcgctca   21420
gtcacccagg ctggagtaca gtggtgtgat ctcggctcac tgcaacctcc gcctcccggg   21480
tccaagcaat tctcatgcct cagcttccca gtagcaggg agtacaggca tgtgctacca    21540
ctcccgagat aatttgtat ttttagtaga acgaggttt caccatgttg gccaggctgt     21600
tctcaaactc cttgacctca aacgatccac ctgcctcggc ctcccaaagt gctgggatta   21660
cagatgcgag ccactgtgcc tggcccacat ttttaatacg ttttgatccc ccttctcccc   21720
ctgagcatgt ccactcagag tgcatctaca gtacgttgat tttgtatagc cctcagtgac   21780
agcttaccat acccttccta ggttgtacag tattgtagtt acttgttcac aggcctgtat   21840
cctcctacta gactgagttg atggcagtta tgaccgatgg tagctgaagt tttatttaaa   21900
tattcaaact aaaaactctt tatctgcagg gacctctcct agtgtagatg catagtcgaa   21960
acttgataat tgacgtgtat tgctggtggt gagggaagtg ctgattgtgg tgcagacagc   22020
acattcctgg atgagggat agtataggca aaggcatgaa gaatgtttgg gagaatctgg    22080
aatgtagaca gaagagaaat tgtgttttga aaatcaaagt aagaagtttg gtaggcaatg   22140
aggagtattg ttttgtttt tgtttttaaa tagagacagc gtctcgccat gttgcccagg    22200
ctggtctcaa actcctgtgc tcaagcgatc ctcctgcctt ggcctcccaa agtgttggga   22260
ttataggagt gagccaccat gaccccaagg gcagttttg atcaggggat ttttcataca    22320
gcttgtgcag ctggtgctca aagtgtgatg aatgaatgaa accaacaaga tgtatctgaa   22380
ttactttgtg agtacattat ctttggaact tgtttcatgt ttacagaaag taaattggtg   22440
gtttaagtgt tgggagctgc ctgtgtatcc tttgtgtgaa agaattagaa cacacagatt   22500
ttattcttaa gtagtttcta attttgttga ggaaacaaac atttgaaagt tatgggcctt   22560
tgcaaaacca ttatacaagt aaataatact tagattatat gaagatatag aacaaaaaaa   22620
gtatctgagt agcataggt taatcaggaa acaattcttg gaggaagtaa tacaaggaaa    22680
tgggaggctg aggagagcat ttgcctctgc agtttatgga gaggatttta ttaaattatt   22740
```

```
caaattcatt tcaatagaat attcccagta gataacatta gcatttaaaa cagccaactt    22800
ctgccatttt cttacaaaaa ttcagctttt agagggaaag gaaaagtcat tcctttcctg    22860
tgatagatca tgtttgtttt ctaatgttgg attagagatg gggaagagg gaggcaaatt     22920 aagtgttaaa ctggaaggag gtgagggaaa gtggttgctt gggatcataa aatgcaaaca    22980
taatgttgct acttcctcat ttcactgaga gagtggtatt cataaccaca tcctggtttt    23040
cttcctcatt tcattataaa agagagccca gtttaactgt gttaattctt tgatgtaagg    23100
aaataccgta tgttgctttg aatacaacta aatcacatga tcataccaat aaagatgagt    23160
taccatgagt ttgttctatt ttatatacat tgcataaaat tcttggaatt ctttaccccct   23220 taatcctctg ttattcgtgg tgttttggat gagaatgttg ttttctcaa tctatggatt     23280 atttctttgt gatgtgaggt gaagctagta gttcagaaac acgtacgtga cagatacagc    23340
aaaagcttga attaataaag atgttctagg ctgaggcagg aggatcactc aaggccagga    23400
gtttgagacc agctgacaca acataatgaa acctcatctc tacaaaatga aaaaatttaa    23460
ttcagaaaaa aatattctaa tatttagata ggaaatagct aggaacgtaa ggagtaaatt    23520
atggtaggta gttaccacac actgacaaaa ttttaaacta acattttgcc tccacagctt    23580
gttcatgatc agatatttaa aaacgggagg accaaatacc acattctcac ttatttttta    23640 attttttttaa ttttttttttt ttttgagatg gagtctcact ctgtcgccca ggctggagta  23700
cagtggcgtg atctcggctc actgcaatct ccgcctccac ggttcaagtg attctcttgc    23760
ctcagcctcc caagtagctg gaattacagt catgcaccac cacgcccagc taatttttg     23820 tattttagt agatacaagg tttcaccatg ttggccagcc tggtctcaaa ctcctgacct     23880
cagcctgcct tggcctccca agtgctggg attacaggag tgagccaccg tgcctagcct     23940
gttctcactt ataagtggga gctaaatgat gagaacatat ggatacaaag aggaaaatga    24000
cacttgtggt gggtaggaag agggagagga ttagaaaaaa taacccattg ggtgctaggc    24060
ttagtacctg ggtgacaaaa taatctgtac aacaagccat tgtgatgcga gtttacctgc    24120
acaacctgca cacgtacccc tgaacctaaa ataaaagtta caaaaaataa gtagattaaa    24180
aatgggaggg ataggatacg gcgaagggac attatatgtt tatatcccaa taggcttatt    24240
ttcaagatac aaaagaaaga aagaaattca aatacattac taggaattcc cagagggatt    24300
ttattcttgg cctccttcaa aaagtagcgt acagccgggt gcgatggctc acacctataa    24360
tcccagcact ttgggaggcc gaggtgggtg gatcacctga ggtcaggagt tcaagaccag    24420
cctggccaac gtgatgaaac cccatctcta ctaaaaatac aaaaattagc caggcgtggt    24480
ggtgggcacc tgtaatccca gctacttggg aggctgaggc aggagaatgg cttgaacctg    24540
ggaggcggaa gttgcagtaa gctgagatct tgtcacagca ctccagcctg gcaatagag    24600 actgtctcaa aataaaaaaa aaaagtagc gtactaagaa tattctggta cctgtcattt     24660
tggtgcatta agctagggga ttgattgttt ggtttgtctt cttaattct gtgtatgatt     24720 ctacatttaa aaagaacaca actggctggg cacggcggct cacgtctata atcctagcac    24780
tttgggaggc caaggcgggc ggatcacctg aagtcaggag ttgagaccag cctgaccaac    24840
atggtgaaac ccggtctcta ctaaaaatac aagaattatc tggggcgtgg tggcacatgc    24900
ctgtaatccc tgctacttgg gaggctgagg cacgagaatc acttgaacca gagaggtgga    24960
ggttgcagtg agccaagatc acaccattgc actccagcct gggcaacaag agagaaactc    25020
cgtctaaaaa taaatacata catacataca tacatacata catacataca tacagaagag    25080
```

```
cactacttag ctcccccaga atcatctgaa cctgggaggt ggaagttgca gtgagctaag     25140
attgcaccac tgcactccac cctggacaat ggagcgagat tgtctaaaaa aaataagaag     25200
aataaaaaat aaagagcact gtatttcatt gttttgtgtt agttgctggg cacaggacag     25260
cagtagtctt tttaaataat tgacatatca taaaggttac ctatttaaag tgtacgatac     25320
aatggttttt agtatatcta cagagttgtg cagccagcac cacaatttaa ttttgtaatg     25380
tttttctctt ctgaaaaaga aaccatgaac cattagcagt cactccttcc tcatccaccc     25440
tccccaccct cggcagccac taatctactt tctgtctctg tagatttact attcgggact     25500
tttcatataa atggatgttt catgtaaatg ggatcataca gtgtatgttc ttctgtgtct     25560
ggctcctttc acttggcgta atgtatttga agttcatgtt gtagcatgta tcggtacttc     25620
attgcttcct attgctgaat aatatttcat catatggagc agtcatctct acttactata     25680
gggatttctc actggtaaaa aactatactc aaaataaacc tttcaaagaa gctttgtgta     25740
gtaggtttac cactgtatct gtttggacta gtggcagtag gtttacctct gtatccgttt     25800
ggactagtgc cagtgttagg tttgcaagag tttccctgtt acctgttttc cctgtttttc     25860
atgccaggaa agcttttcct tcaaatagtc ccatggctag ttccctcact tccattttat     25920
cctctgttct acccagggca ccccagctaa tttgcagcat gtctcccct ttccttttg      25980 cttttgtttc tgttggtatt tgtcactgtc taacatactt tatttatttt tattttttatt   26040 tattttatt ttcttgagac agtgtcttgc tctgttgccc aggctggagt gcaatggcgc      26100
gatctcggct tactgcaact tctgtctccc aggttcaagc aattctcctg cctcagcctc     26160
cagagtggct gggactacag gcatgtgcaa ccacacctaa ttttgtgtt tttagtagag      26220 acagggcttt gccatgttgg ccaggctggt cttgaactcc tgggctcatg tttatctatc     26280
tgcccacctc ggcctcccaa agtgctggga ttacaggcgt gagccactga gcctggacta    26340
gcaaactttg tattttatat gtttatctct tccaccagaa tacaaattcc aagagggcaa    26400
ggattattac cttttttgttt actactctgt actatagagt gcttggcaca tattagacgc    26460
tcggtaaatg tttaagatac aaggccagag gccaggcgtg ttagctcaca cctgtaattt    26520
caagcacttt ggaggctgag gtgggaagat agcttgagc gcaggagttt gagaccaacc     26580
tgagcaatgt aacaagaccc tgtctcaaca agaaaattaa aaaattagct gggtgtggtg    26640
gcctacaccc atagtcttag ctacttggga gactgaggtg ggaggatcac ttgtacctag     26700
gagttcaagg ctgctgtgag ctgtgattga gccactgcac tctagcctgg gtgacagagt    26760
gaaaccttgt cttttttttt ttttttttttg agacagggtc ttgctctatc atccaggctg    26820
gagtgcaatc gcatgatctc agctcactgc agtctctgcc ttctgggttc aagtgattct    26880
catgcctcag cctcctgagt agctgggact gcaggcgtgc accaccacgc ccagctaatt    26940
ttttgtattt gtgtgtgtgt gtgtgtgtgt gtgtgtggag acggactctc gctctgtcgc    27000
ccaggatgga gtgcaatggc gcaatcttgg cttactgcaa cctctgcctc ccgggcttaa    27060
gcgattcttc tgcctcagtc tcccaagtag ctgggattac aggcatctgc cataacacct    27120
ggctaatttt tgtattttta gtagagacag ggtttcacca tgttggccag gctggtcttg    27180
aactcctaac cttaggtaat ctgcccacct cgacctccca agtactggg attacaggca     27240 tgagccaccg tgcctggcca ttatctctaa aaaaaaaaa aaagtttaa gatatgaatg      27300 gtattgtgag tggtggtaac agtaacaatg taaagtattt tgaagtattt gtagtcgagg    27360
taggtgtgta cgtacacaca tgcacacaca aacatacaaa tgactgtttt agatgtagga    27420 aaaccagtg ttttttttatc ttgaaatctc attctgcgct ttcatggaca gcatagaaac    27480
```

```
agcaaggaag tggcttcctg ttttaacat taaaaacagg aaaggacaga cggtggtatg    27540
acctatatga acagtaagga aagtcgttaa ttaaccatgg ttgaaaggtt taaaagttgt    27600
agtctgaaaa cctttcattg agtatttcac ctactttct tcattaagta gagataaaaa    27660
cagaattatt ggtttataaa atactttag aatttataat gctttccttt tccctttttc    27720
ttttctttct ttgtgtgttt tttttttttt tttttttttt tttttttttt gagacaaggt    27780
cttactctgt cacccaggct gaagtgcagt ggcacaatct cagctcactg cagcctcgac    27840
ctccctgtgc tcaggtgatc ctcccacctc agcctccgga gttgctggaa ctacaggcac    27900
gtaccaccat gccctgctaa ttttgtgtt ttgttgtaga gactgggttt tgcccccagg    27960
ctgatcttga acttctgggc ttaagtgatc cgcctgcctc agcctcctaa agtgctggga    28020
ttataggcat gagccactgt gcctgggcca gattttttt ttttctttc agagacagga    28080 tcttgctctg ttgcccaggg ttgagtgcag tggcacaatc tcagctcgct gcaacctttg    28140
cctcccacgc tccagtgatt ctcccacctc agcttcttga gtagctggga ctagaggcgc    28200
acgctaccac aactggctaa ttttgtttt ttttttttg tagagacagg gtttcgcctt    28260
gttgcccagg ttgatcttga actcctgagc tcaagcgatc cacctgcctt ggcctcccaa    28320
aatcctggga ttataggcat ccaccactgc gtccaactat aatgaatttt aactgtgtga    28380
tgactccatt ttcaacactt cctcaggtgg gaattatttg ggatttaaaa attcttaatt    28440
taagttttga aacaactttg tcatgtttca gttacttcta aatctatctc ataaggctat    28500
ttccttcttt agtagaaaat acattttcca gctgggtgtg gtggctcata ccaataatcc    28560
cagcagtttg ggagactgag gcaggaggat tgtttgaggt taggagttta gactggcgtg    28620
ggcaacagag agagatcttg tctctacaaa aaatttaaaa attagccaag catggtggtg    28680
tgcacctgta tgtagtcctg gctacttgag aggctgaggt ggggagatag cttgagtcca    28740
agaatttgag gctgcagtga gctatgatca tgccacttct ctccagcctg gttacagag    28800 tgagacactg tttctaacaa taacaacaac aacaacaaca aatgttgccc aaataaaaat    28860
tcaaaacgtt atagattttt tttttactat cttgtctttg atatgcaata ttatgtttat    28920
aatgaaatgt cttgaaatct tttagtagta ctatcatacc agcaaacagc attagttatt    28980
attattatta ttattattat tattattttg agacagagtt ttgctcttgt cgcccaggct    29040
ggagtgcagt ggtgcgatct cggttcactg caacctccac ctcccaggtt caagagatca    29100
gccttccgag tagctgggat tacaggtgcc tgccaccaca cccggttaat tttttgtatt    29160
tatagtagag acgggtttcg ccatgttggc caggctggtc tcgaactcct gacctcaggt    29220
gatccacctg cctcagcctc ccaaagtgct gggattacag gcatgagcca ctgtgtctgg    29280
ccttccttca ttttaataat aatggatatt gaggcttttt tcatttcttg tcagtgatga    29340
ataaaactac tataaatgtt ctgatatatg catttcctgc atgtaaatat gagtttctcc    29400
agggttggaa ttattgagtt atagagttat agagtatgca tgtcttcagt ttcactagat    29460
agtgccaaat tgttttccaa agttattgta ctggtttgta cacctaccgg ctgtgtttga    29520
gaattctttt tttttgaga ctgagtctcg ttctgtcacc caggctggag gagtgcagtg    29580
gcgtgatctc agctcactgc aagctccgcc tcctgggttc acgccattct ctgcctcag    29640 cctcccgagt agctgggact acaggcgccc gctaccacgc ccagctaatt ttgttttgt    29700 attttagta cagacgggtt tcactgtgtt agccaggatg tcttgatct cctgacctcg    29760 tgatctgcct gcctcggcct cccaaagtgc tgggattaca ggtgtgagcc actgcgcccg    29820
```

```
gccaagaatt gttccacatc tctttactaa cactcagtat tgccagaatt taaaattttt    29880
gccagttcaa ttggtatata tgtactagtg tctcattgtg gttttaattt gcaattctct    29940
attgcccagt gaagctgaac agcttttat  atgtttaatg accattggaa gtgctgattt    30000
catgaagtct ctgttcaaat cttttgtccg tttttctact gggtttgtgt attttctaa    30060 gtggttttta ggaaatattt atgtatccta caagtatttt gcgtctacca tccctctttt    30120
gtggcttgtc tttcgcttag catagtgttt tcaagattca tgtaccattg tagcaagtaa    30180
cagtacttca ttcctatatc actgtatact attctgttat gtggatatac cacattttgt    30240 taccacctt  tggctgttgt gaatagtgct tctatgaaca ttcacataca agtacttgtt    30300
cgagtatctg tttccaattg gtacgtacct aagaatggaa ttgctgggtc acatggaaag    30360
tctatattta ccttaaaaa  aattattttt tggctgggtg tgatggctca cacctgtaat    30420
cccaacactt tgggaggcca aggtgggtgg atcgcttgag gtcaggagtt tgacaccagc    30480
ctggtcaaca tggtgaaacc ccgtctctac tgaaaataca aaaattagcg ggatatggtg    30540
gtgcacacct gtaatcccaa ctacttgaga ggctgaggta cgagaattgc ttgaacccag    30600
gaggcgaatg ttgcagtgag tctagattgc gtcactgcac tccagcctgg taacagagc     30660 aagactccat ctcaaaaaaa aaaaaaaaga aaaagaaaa  aatttatcac gttcatcgtt    30720
gtcaaagtct acatgtacct ttgagaaacc aacacacttt tccaccttgg ctgtgccatt    30780
ttgcatgtcc accaggaatg tattaaggtt tttctgagtc ttatagtttt atatttacg     30840 tttagggcta tgctccttt  gagttaattg tataaggtat gaggtttagg tcgggtcatt    30900
tttttggcca gtggatgtcc tagtgagaaa gttttaaaa  taagtatggc atttaaaagt    30960
aatctgtgaa ggtctaaata ctttatagtt ttgtagattt aaatttttct cccacgtttt    31020
cctttactta gcaagttttg aataaaagta aagctgaaat aaatttgttc cttaaagact    31080
gctagagttg gttacttgt  cccagttttt tttccctgca ctggatgcat aggtcaaggg    31140
tcgaacttta aatcatcctg accttgagaa gacactgaga cagttctaag catgttttcc    31200 aagctttta  tcctaacatc aaagcagtga ttgtttgcct caaatgctca tgtttgagag    31260 aaatttgtc  ttttgttata tcgagattgg tgccccagac tctaaaataa gtaaagtta     31320 ttaaattaga actgacattg agaattctta atggaattag tagtaacact accactaata    31380
gtgttagttt ggaataatac tagtctcagt tttggctttg tcactgcatt gttatgtgac    31440
ttggacaaag aatttaaatt ttattcagtg actctgtaaa atacatctaa taagttatta    31500
aacatctatt tctcaacaat aattataatg accacgttgt tgaaatcgtc acattattgg    31560
tagagttacc aaaaacactg taggtcattc aagccaacag agaattaggc atttatggct    31620
ttgtggaggg gcgagagcag tgaggttagg gcctccctcc cctaactggg cagctaccc     31680 aaactaggaa actgctcctg ccgtgagtac tctgagtgct ggcatcacaa ctgtcgcact    31740
gccagaggct ggtgaatagg cagtggcaca tagaatcgcg ctggtgccga cccagcactg    31800
aggtctgcag gggcttgcct cctacgctgg tgcaaagcgt ggccctgcc  atccagctgt    31860 tgtatgtgct tctcactggc agaccctaca tcacatccgc aacccgatca caagggtgtc    31920
caggaaatac agttttagc  cttccatctc ctaagtgtgt gtgtgtgtgt ctgtgtgtct    31980 tgtaggggt  ttgttatgtg tgtgttggtc atatgcagaa catagggaaaa gaatgggaag    32040 gacaatagca cagtggtctt gaagtgcttt gaacgctatc aaagtatttc agattgattt    32100
agtagcatca ccaaataaga ggcagtgtgg cattgggtt  gggagcacag agtaaagtta    32160
gaaggcctgg atcatcagtt cctggctctg cctctggctg cttcctaag  tgggaaagcc    32220
```

```
atttagcctt tctgaaagtg taagaaatat cttccttaag agtgtgcaga gtatgtatat    32280
ttacatactt acatatataa gtatataaat atgtgtgcat gtaaagcact tggcaagtgc    32340
ctggtatgtc ataaatactc agtagatggg cactcttgct gctgttgtga ttattcatca    32400
tctttatcat catcatgtaa acatatttga ctatctgtgt tggaccagaa tgatgcttaa    32460
caaagggaca gttgttagaa agtggacttc aaaaagtgat agcatccagc tttgccccct    32520
gtgttcttaa tgcctgtata ggtgctacaa taggtggtac ttatgtatat tatattaaac    32580
aatatgggat atttctaga aggcttacct taaataggct taaccagtaa aggatattta    32640
ttggcttctt attgagatgt ccctagacta cttttgataa ggtcttcatt gatctctaag    32700
cagcaaatcc aagagtttga gttgttctct tgagttgaga aggctcttaa gtgaggagta    32760
tttcaagccc agtgatccag catttagtcg cgagtaggta ttgttttccc tctccttaca    32820
tgtgctagga tatgggattt gtgaggatct tcaggaagaa tgtttatgag tatatcctta    32880
aggctgcttg gacttgactt taccattgtc actcccttat cagttaggta ttcgctcctt    32940
ctctggacaa acactctttt atagtactta ttatattgta tttatttgtg tgtttctcca    33000
ctacactaag agttcttagg gagtgtagag gttgttctta ctcattttta ttcccagtgc    33060
ccagtttagt gcctggaagg tactgctcag taaatgttca ataactgagt attaggtcaa    33120
tgatgatgag tattacataa gccttaacta aagtcacttc acagtgacca aactgaggag    33180
gaggaagaga gtggtggaga tgggggaatg agggtcggaa tagtggggct atcactcttt    33240
gcggagagaa ctgtcttgtt ctttaacgta tcctgaaagt ctggcataca acccagtatg    33300
tatcgagtac tcactaagat atatttgaat gaatgaatga aaagattacc cccctagttt    33360
aactgtggtc ttagagtgtt taaagttaac ctgatatttt tggaaataca ctcccattgc    33420
ctagaactgg aactgcaagt agtgaccct cccctccttt ttttcatggc taagctgcag    33480
ggagtttggt ttgctgccct tctcatcttt tttaaaatta ttattttat ttatttattt    33540 atttatttat ttatttattt atttattgag acagcttttc actctattgc ccaggctaaa    33600
gtgcagtggt ccgatcttgg ctcactacag ccccaacctt ctgagctcaa gtgatctgtc    33660
cacctcagcc tcccacgttg ctgggactgc aggcacatgc caccacacct ggctaatttt    33720 tgtattttt gtagtgacag agtttcacta cattgcccag gctggtctca aactcctggg    33780
ctcaagcgat ccaccccgcct tgagcccaaa gtgctgggat tacggcgtga gccactgcgc    33840
ccagccatgc ctatcaaatc tttctgctga acctactgac tgagatcaga gctactaccc    33900
tggagcttag ctaaggagta aaggggagct gagatttcgg ccgtaagtcc ctctctccta    33960
ccattctatg ccacccgctt ttggtcccta acatccctgg ttgtgacagc ttctcctcct    34020
ttaccctgtg ctactgtgac ttaatcactt gttaaggaga gatggaaatg cctgaccatg    34080
gcaggcacaa ttcttttgttc aggaaattgg aacccattgc ttccttccta atcccagaca    34140
gctgtgcctc tggttttctt tgtttagccc aaggctgagg ggtgaagctc tacttcattc    34200
tggcctgcag tctttttct atcttgggt ttgataatcc ctctggtatt tggagcagac    34260
tctaaggttt ttctgttta tatagtaaaa caaaaaatat tgcttttgtt gctaataaaa    34320
atttgtctgt aaggaaatat ttctcttaat attggagtta atactttgaa cattaatgtg    34380
cagtgtttag aaagattata aagaaatgag attggccggg cgccatagct catgcctgta    34440
atctcagcac tttgggaggc tgaggcaggc agatcctttg aggtcaggag ttcaagacca    34500
gcctgaccaa catggtgaaa cactgtctct gctaaaaaat acaaaaatta gccaggtgtg    34560
```

```
gtggcgggca cttgtaatct cagctacttg ggaggctgag acaggagaat cacttgaacc    34620
taggaggcgg aggttgcagt gagccgagat cacaccattg cactccagcc tgggtgacag    34680
agtgagactc tgtctcaaaa aaaaattttt tttttttaatt aaaaaaaaga aatgagataa    34740
tcagtactgt catttccttc attagaagcg ttagtactgt tacccttttt tacatgaatg    34800
aaaaggattg aagactactt tttgttttt cctttgggaa ataaatgcat ggataataac    34860
agccaaataa aaagttttaa ttagaattgg atatctctat tcctattttc attcaaccag    34920
tatacttgtt ggaaggctat caaaatggac atgccattta aatgaaaaat ttccaattgt    34980
gatagacatg ttatttatga atattttctg tcctgaggaa aattaactat tagaaccagt    35040
tgtaaaagag atggtggctg ggcatggtgg ctcacaccct taatcccagc actttgggag    35100
gccgaggtgg gtggatcgcc tgaggtcagg agtttgagag caacctggcc aacatagtga    35160
aaccccgtct ttaataaaaa tacaaaaaat tagctgggca tggtggcaga gtcctgtaat    35220
cccagctact tgggaggctg aggcaggaga gtcgcttgaa cctgggaggc agaggttgca    35280
gtgaggcgag atcacaccat tacactccag cctgggcaac aagagtgaaa ctctgcctca    35340
aaaaaaaaaa aaaaaaaaaa agagagatgg tatcaggtac tgcaaattct tagagtagct    35400
tctgactttg ctcagcctta tttataagat ttatctactg ggaggctcat tcaataggca    35460
cttgagagtc cggtgtcata gaaagttgtt aattttagag ttgtatgcag ccttctttag    35520
caatgaaaat cttttacaga ataaggctta agcttttttca atgttttga ctgatttagt    35580 taacagctta atttatattg gcaccaagcc cagatctaat ggttataaac tcagtagttg    35640
gctgatacag taaaaactgt agtttcgttt tcttgttgtt tggtttaccc tttacattca    35700
agagtttaag tagatctcat atggtctggt cacatgtgtt ctgagtagtg gtcataccac    35760
accaggcata gcatttctgc tccgctgtga cttgattttt tacagactta agttttagta    35820
caacttaatc tctcagagga agggttaagt tcctgagcat aggaattcat tttgggaatg    35880
tattttcttt tctttctttt taaaaatta tttgtagaga cagagtccca ctatgttgcc    35940
caggctggtc ttgaactcct gggctcaagt gatcttcccg ccttagcctc ccaagtgttg    36000
ggactacagg catgaaccac tgtgtcctgc cttcttttct ttttgagaca ggttctcgct    36060
ctgttgcaca gactggagtg cagtggtgta gtcatagctt actgtcactt cagattcctg    36120
gccacaagcg atccttccac cttagcttcc cgaagtgttg gggttacagg catgaaccat    36180
tgtacctggc ctctttttt tttttttttt ttcttttta aaaaattcct ttctaaaggg    36240
aaaagaacct aaggtgggtg gcttcctata accatttttt tttttttttg atatggagtc    36300
tcattctgtt gcccaggctg gagtgcagtg accacggccc actgcaacct ctgcctccca    36360
ggttcaagcg attctgctgc ctcaagcctc ccgagtagct ggaattacag gcacccgcca    36420
ccatgcccag ctaatttttg tatttttagt ggcgatgggt ttcgccatgt tggccaggct    36480
ggtcttgaac tcctgagact tcaagtgatc ttcccaccca cccacctcgg cctcccaaag    36540
tgctgggatt acaggtgtga gctaccacac ccggccccta tatcctattt tatagtgttt    36600 cttgttatt attttctctt tggatttgtt tcattttgat ccttgaaaat atgcaaagga    36660
tggaatctta attttggaat tgttttcctt ggttgaaatt ggaattatgt ggttttatg    36720 gcatttcccc taatctatta atgtgggagg aggcttgtgg ggagggaaga gccgtctttt    36780
tgagattatt agggagggaa accatttaat gacagaattg tatgactaca ttttattttt    36840
atgaggacta ctttgttaat ttacattctt gtgctctaca ttcatgaagt cagttatttg    36900
aaaccatgta atatatgtca actattaaag ttaagtgact tttatctgat aagagttgtg    36960
```

```
ttaaaataat catagagaat tgatgccttt ccagatgttt tcctgataca tcagggtttt    37020
ttttgttgtt gttttttgctg ttatccagct tggagtacag tggtgccatc atagctcact    37080
gcagccccaa tctactgggc acaagggatc tccctgcctc agcctcccga gtagctggga    37140
ctacaggtgc actgcacctg gctaattttt aaaatgtttt tgttgagaca gagtctcgct    37200
atgttgccca ggcttgtccc gaactcctga gctcaagcag tcctcctgca ttggctttct    37260
aaagtcctgg gattacagac gtgagccacc aagcctgtcc tgatttagca gttaattaaa    37320
tataagtggc ctctcattct caggtgctct tacagtatga aaatggaagt tgtaaagttt    37380
gtttttaaag taactcagtg gaatgataga cagtggagac ttggaagggt gagggagtga    37440
gggtggatga tgagaaatta cttaatgggt accatgtgtg ttatttgaat gactgatacc    37500
gtaaaatccc tgacttgtcc attacacaat cttgcacgta atgaaattgc ccttataccc    37560
cataaattta cataaataaa agatcatgtc atctgttaaa aaatttttta ataaagtaac    37620
tcagttaaat ttatggtatg tcaccatttc ttggcaggac tttgtgtcat tgtatcaaga    37680
ttttgaaaac ttttatacaa ggaatctgta catgaggata agagacaact ggaatcggcc    37740
aatctgtagt gtgcctggag ccagggtgga catcatggag agacagtctc atgattataa    37800
ctggtccttc aagtgagtct tggttgggaa attatttgac aacaattaca aaagggtttc    37860
ttcatttgag aaaatatgtt attataaatt gagtattctc tcaaaatagg agtagcagct    37920
gaggatacaa tatgattggt ttccttacat attcttcatt gttgagcttt ttaagatata    37980
tctttctatt acatttgata ctgtgttgga ttatagttca gaagaaaatt tggcttattt    38040 atttttttgag atggagtttc gctctgtcac ccaggctgga gtgcagtggc gtgatctcag    38100
ctcactgcaa cctccgcctc ccaggttcaa gcaattctca tgcctcagcc tcccgagtag    38160
ctgggactac aggcatgcac cgccacaccc agctaatttt tgtatttgtt ttagtagaga    38220 tgggggtttca ccatgttggc caggctggtc tcgaatgcct gacctcaagt gatctgtccc    38280
cctcagcctc ccaaagtgct gggattacag gcatgagtca ccgcgcccag cctggcttct    38340
ttatttttaa aaataactcc tattgataag aaacagtata caaaagttta gtctgtttta    38400
tttttggtct tgactttaaa aaaaaaaaaa aagaaaagct atcctttcca ttatgccact    38460
tatcagaatc aagtatccaa atttatttct ggatattttg atttctcaaa tgatttaagg    38520
atgatatgta gagtgttttt acttacatgg attgaatagt ttggaaaact ttttgtattt    38580
ttaacattgt atttgtttgt ttgtttactt attcatttat ttgagtcaga gtctcgcttt    38640
gttgcccagg ctggagtgca gtgtcacaat cttagcccac tgcaacctcc acctcccaag    38700
ttcaagtgat tctcccacct tagcctctct ggtagctggg actacagaga tgcaccacca    38760
tgctcagcta cttttttgtat ttttagtaga tgtgaggttt caccatgttg gccaggctgg    38820
tctcgaactc ctggcctcaa gtgatctgcc caccttggcc tcccaaagtg tcagagtctt    38880
gctctgtcac ccaggctgga gtgcagtggc accatcttgg cttactgcaa gctctgcctc    38940
ctgggttcac gccattctcc tgcctcagcc tcccgagtag ctgggactac aggctcctgc    39000
caccacaccc ggctaatttt ttgtgttttt tagtagagac agggtttcac tgtgttagtc    39060
aggatggtct caatctcctg accttgtgat ccacccaccg cggcctccca aagtgctggg    39120
attacaggcg tgagccaccg tgcccggcct acagcttgcc ttcttagctt ggtcaaatat    39180
cagtgacacc ccttctcatg tgtatattca cagcaagttt attatttgta gtgactacat    39240 tgtatttttac agtatacatg tgccatggtg tgacatgttg ggctgtgtta ataatctcaa    39300
```

```
aatctcaggg aattaaaaca gtaacagttt atccttatcg atacttcatg ttcatcctag   39360
gttggtgggg cccttgaacc attttgtcct tagttagggg cccaggctgc ctcagcttcc   39420
attgtatgaa atgtcactgg tctctgtatc tgaagaacag atgtggcaaa ttgtgcagtg   39480
gctctcaaag gatcctcatg tgtatatatt ctcatgtgcg ggagttactg agtatgtata   39540
tcttttaatg gataagtact gccaaactgc cctccaaaaa acaaacctga tattcttatg   39600
tacagtgtcc tgtaagataa ggtgattgtc ctggccaaca ctggatatca ttagttttaa   39660
aatctttatc actattaata aatgaaaatt gattatttta acttctattt ccataattgg   39720
tagtgtgttt gagattttt taatatagac tttgttctct ctgcttcctt ttgtgtcacc    39780
agttcattta atattacatg taagtacttt tttgctcatg agtttcattg ttttatgcta   39840
ttgatgcaca ggtatacagg gaatataata aagggtgtta taaacatggg ttcctacaac   39900
tatcttggat ttgcacggaa tactggatca tgtcaagaag cagccgccaa agtccttgag   39960
gagtatggag ctggagtgtg cagtactcgg caggaaattg gtaagtgaaa gctgtatttg   40020
gccagctgct gttttgaca ttgttttagt caggggcaaa taatagtaat attgacctag    40080
agtattaaat atctacactt tgtcatgtca tttagataag gtgaagaatg ctttgttttt   40140
ctgaagtgtg atggatgatt tcaatgcttt caacacattt tgagatgtgt ttatctttcc   40200
caatgtgtta tacatataga atgtccctcg aaaaatcctg ccagtgtttg tttcatttat   40260
aactttaatg ttgatttcat tggcttttgc aaatgttagt ggttaagagt gccacttatt   40320
aggatgttgg gcatatgaga gttaatctgc tttcatactg gtacatgggg gctaataata   40380
attcctgcct tatagagctc ttttaagaat tacgtaagct aatccatgta gagtacttgg   40440
aacatagtag acaataaata taaactcttt ttattattgt tttaagtttg taaaatataa   40500
aagagtaata actttatata aagagattca atttatttta attcagcgga agatttcaga   40560
ttgttccaat ttgattcaga gaactgacaa ccctggaagt tatgaaaact ttccaaatac   40620
ttattactgt aagcacagta gattaaaaga acagttcatt gttagttatt tctcagggtt   40680
ctagggattg gcaagcacag ttgggtgctt cttacccaag gttcctctca cggttgcact   40740
cagtggtggc tgtatggctg gagacatgaa gccttcttca ttcgcatgtt tcacctaggc   40800
tgcggtggct ggagctctgt gtggcctctc catgtttcta gcttgggttt cttcatacca   40860
tggtggtctt ggagagttgt tcatcatgca tggctgcagg cctctagagc aagcatgcaa   40920
agatacctga ctgaagccag gcacggaggc tcatgcctat aatcccagca ctttgtgagg   40980
ccaagatagg aagatcagct gaggccagga gttcgagacc agtctgagca acatggtgag   41040
acctgttctc taaaaaaata aagataaagt agccgaacgt ggtggcgcat gcttgtgatc   41100
ctagccattc aggaggctga ggccagagca tccctcgagc caaggagttt gaggctgcag   41160
tgagctatga tcgtgctact gcaccctagc ccatgacaga gtgagacact gtgtcaaaaa   41220
acaaaaacaa ggatacccag ttgaaagttg gaaggctttt tatgccctag ctgtacaggt   41280
cccaaagtat catttatgcc tcttctattg gccaaagcgt cgctaaggtc agcccagatt   41340
caagggttgt ggggattgcc ctcctccacc tccaaatggg aagaataaca aagaatttgc   41400
atccatattt aatcttccat agcaactctg tcagctcacg aaatttaaaa caacatgaag   41460
acagggaaaa aaataaaatt gtgcagattt ttatatctat ttatttagat agctagatac   41520
atggatatat agatagattg atgcatagat ggatgcaggg tctctgttgc ccaggctgga   41580
gtgcggtggt gcagtcagct cacttcagcc tcaaacttcg gtactccagc catcctccca   41640
cctcagcctc ctaagtagtt aggactatag gtgcacgcca ccatgcccag ctgattttt    41700
```

```
aatgtgattt tgtagagat ggggatctct ttcaagaggc tatgttgccc agggtgttct   41760
tgaaatcctg gcctcaagtg attctcctaa ctcagccttc cagaacactg ggattatagg   41820
tgtgagtcac catgcctggc cccaccatct aattttaaat attttcattc ctcctaaaag   41880
aaatgctata ctcagtagca ttcattggat actgtttccc ttccccctac aagtccttgg   41940
caaccagtag tctactttt gtctttatag atttgcctat tttggacatt aaatataaaa   42000
ggaattgtat aacatttggt cttttctgtc tggcttcctt cactagcaca atattttcaa   42060
attcatccat gttgtagcct gtaacagcac tccattcttt tctatgactg aataataatc   42120
ctttgtgtga gggtgccacg tcttgtttat ccacttatca cttgatggtc atttgggttg   42180
tttctacttt ttggctattg tcagcagtgc tgctgtgaac gtgggtgtac aagtttttgt   42240
atgatatatt tttgtttctc ttgggtttat acttactagt ggaattgcta ggtcgtatgg   42300
taactctgtg tttgactttt tgaggaattg ctaaactgtt ttccaaagag accgtactgt   42360
tttacaatct ctccatcgat gtatgagggt tcctattcat ttttatatca tcttccagtc   42420
atcttgtttg tagcccaact ttaacccttg attactttgc tacctgttcc ctctggtttt   42480
taagcttctc tagggttcca tacagtgaat ttacttggtt ttcaaaggat tccactctat   42540
aagggcatag atatgacctt cttctaactc tgtcattttc cagttgtatt agtttcctgt   42600
ggctgctgta acaaaatatc agaacagagt gacttaaaac aacaaaaatg tctagtctca   42660
taattctgtg ggttataagt ttggggtcta ggtgtcagca gggccatgct gtctgatgct   42720
ctggagaaac cttcctagct tctggtgtcg acagcaatcc atgacgttcc ctggcttata   42780
gcacatcact ccaccacacg gctgtcttcc tgtgtgtcaa acattgtcgt cttctggccg   42840
ggcacagtgg ctcatgcctg tcatctcagc actttgggag gccaaggcgg gcagatcact   42900
tgaggtcagg agttcaagac cagcctagcc aacatggtga aaccctgtct ttactggaaa   42960
tacaaacatt agctgggcgt gatggaaggt gcacgcctgt aatcccagcc actcgggagg   43020
ctgaggcacg agaatctctt gaacctgtga ggcagaagtt gcagtgagcc gagatcacac   43080
cactgcactc cacctgggca acagagtgag actctgtctc aagaaaaaca aaaaaacagc   43140
attgtcttct gtattccttc tgtgcatgtc tatcactgtg tccaaatttc ccctttctat   43200
aaagacatta gcatccccct aatggcctca tttttattt ttatttattt atttatttat   43260
ttatttttaa aatctttgta aaatttttt attgatacat aacatttgta catttgtgtg   43320
gggtacatgt gatgtgttgt tacatgtata gaatgtgtat agaatcaagt caaggtattt   43380
agggtactcg tcaccccaag catttattat ttctatatgt tgggatcatc aagtcctctc   43440
gtctagctat ttgaaatata caatacattg ttttaacta tagtcaccct actctgctat   43500
caaacattag aacttatttc ttctaactct atatttgtac ccatttacca gcttttcttc   43560 atctccccg ctcccctac ctcatctcaa cacacatcct tccagtattg ttttactcgc   43620
tacctccatg agattaaatt tagtgaggaa ggcatgttaa aagctgacat aggccaaaag   43680
cgaggcctct tacaccaagc aattagccaa gttgtgaatg caaaaaagt tctcgaagaa   43740 aattaaaagt gctactccag tgaaccccaca aattataaga aagtgaaaca gccttttatt   43800
gctggtagag agaaagtttt agtggtctgg ataaaagatc aaagcagcca caacattccc   43860
ttaaacccaa atctaatcca gaagaagatc ctaatcgctt caattctatc aaggctgaaa   43920
gaggtaagga agctgcagaa gaaaagctta agcctagcag aagttcattc atgaagctta   43980
aggaaagaag ccatccccac aacataaaag tgcaaggtga agcagtgaat gctgataact   44040
```

```
tcagcaagtt atccagaaga tctagctaaa ataattgatg aaggtggcta caataaatca    44100
cagattttca atgtagatga aacagcttta aattgaaaga agacaccatc taaaactttc    44160
acagctagag acaagtcaat gcctggtttc aaagcttcaa aagacaggtt gaccctactt    44220
ttaggtgcta attttaagtt gaaccaatg aatgacctca ttttaatttg attacctctg     44280
gaaagttcca gtttccaaag aaggtcacat tcttctggga atgaggacgt caaaatatct    44340
tttttggtgg gacacaatgg aacccgtagc atcatccttc tgtatatttt ccattttcat    44400
taattgtgtt cagaattaca gatgtccact aattaataaa aaattgagct tttagctttt    44460
atttcttggt tatccagttg ttttgtgatg attttcaaga ggaagatggg agtagaacat    44520
ttttatttcc ccctgccttt aaaacagagt ttctaactgg cactccagaa atgacaagcc    44580
ttgtgatcta atcctgtggt taaggagca ttgtgcagtg gcgacatata gtaaggatac      44640
attatgcctt tatggcattt gatattttat aaagtgctcg gctggatgcg gtggctcacg    44700
cctgtaatcc caacactttg ggaggccaag gtgggtggat ctcttgaggt caggagtttg    44760
agaccagcct ggccagcatg gtgaaacctg tctctactaa aaatacaaaa tagtcaggcg    44820
tggtggtccg cacctgtaat cccggctact gggaggctg aagcaggaga attgcttgaa     44880
cccaggaggt ggaggttgca gtgagctgag attgcgccac tgcactccag cctgggcgac    44940
agtgcgagac tctctctctc aaaaaagaa aaaagctca aacgtattat ctcttttgat       45000
cctcacaaca atgtcatgag gtagataggg caaattatta ttgctattta gaagtatta     45060 gcccagagag ttcctaaggg ctttgattaa gcaagcctta aggacacatg gcatccaagt    45120
ttagcattct tctttcccgc atcttttctc tctgtaatgt catttagtcc ttaaagattt    45180
gagtaccaat ataaaattgc ggtacaaatt taccagtcag ttcacagtga gggaagaacc    45240
tttttttttt tttttttga gtcagagtct cgctctgttg cctaggctgg agtgcagtgg    45300
tgcgatctca gctcactgca acctctgcct cccaggttca gcgattctc ctgcctcagc     45360 ccccgagtag ctgggattac aggcacacgc caccatgcct ggctaatttt tgtattttga    45420
gtagagacaa ggtttcacca tgttgccagg ctggtctcaa actcctgacc ttaggtgatc    45480
cgccctcctt ggcctcccaa agtgctggaa ttacaggcgt gagccactgc acctgccag     45540 gaagaaacgt ttttacctat cttttgctgt ataacaaacc atctcaaaac ttagtggttt    45600
aaaacagcaa cagattttat tgctcatgat tctgcaattt agggagggcc tgatgttatc    45660
ttagctccat gtggtattgg ataggcaatt atgactgtgt acagggtatc caagatgtct    45720
taactcacgt ttgacacttc agctgggtgg caggaagggc taagggctgg ctgggcatct    45780
ctgtttctct ttctctctgt ctcccctct ccttacgtct ttctctcctc cttccatagt     45840
ctcttatccc tcagttccca tccccccgcc catgttctgt ttttgcaaca ggccagttag    45900
attgttttac atagcagctg acttcaaaag tgtaaaagca gattttgcta ggcctcctaa    45960
ggcctagacc tggaactagt atgcacaaac aggaatggga gaaatttttc gcagcccct     46020 ttggggaaat tccactgcag gtgctgaatc agatttatt caactattgt gttctttatg     46080
agcacatatt actcttcaca atattatgaa gaatattact cttcataata ttgactcctt    46140
catagatctt agtctgaaaa ggacacaaca catatactat gatttctttt aataaagtga    46200
tgagtaattc ttaaattcag gattttgtga tactgacttt attaacttct tcacacagga    46260
aacctggaca agcatgaaga actagaggag cttgtagcaa ggttcttagg agtagaagct    46320
gctatggcgt atggcatggg atttgcaacg aattcaatga acattcctgc tcttgttggc    46380
aaagtaagat actctgtcat ttatgaaaac tccctcatgt atatcttctt ttgttttgaa    46440
```

```
aagcagtcag agtgagctaa aagctgttat aaactttagg ctaaacatag tttagccaaa    46500
gatatttcta ccacaaattg ttttttcttt tttttttttt ttttgagatg gagtcttgtt    46560
ctttcgccca ggctggagtg cagtggcacc atctcagctc actgcagcct ctgtctcttg    46620
gattcaagcg attctcctgc ctcagcctcc caagtagctg ggactacagc tgtgtgccac    46680
cacgcctggc taattttttg tattttagc agaggcgggg tttcaccatg ttggccagcc     46740
tgggcaacat agtgaggcct cgtctcaatt tgattttatt ttttaaatta aaaacaattt    46800
gtggccaggc gcagtggctc acacctgtaa tcccagtgct tgggaggct gaggcaggtg     46860 gatcacctga ggtcaggagt ttgagaccag cctgtgttta tatatttata tacatatata    46920
taatattgta tattatatat atatataaca tatatgtatg ttacatatta tatatattac    46980
atattacata ttatatatat aatatatata tccccaagtg ggtagtgtgt gtgagagggc    47040
acaatctgta tgtaaatgta aattatattt cagcagattg gtactctcat cctgaaaggc    47100
cccttgaggt tatttattct catgtttaac atgacactta ggaatggtat attgaaaacg    47160
tggtggatta actcaagcag gagaattgag ttttttgtttt ttggttgttt atatggtcac    47220
acttagctgt gtgactgtga gcatgtcaaa taatcttttct gatcctccaa gtttcttttg    47280
taaaatgagg tggttgagct agattaactc taaagtcctt tttagttatg cagtgtatgg    47340
gtctgtaagg tacagatggg acaaatgaaa acaaacagc aagataggag atttaaaccc     47400
acctgtgttg ataaacatta aatataaatg gtttgtacat tccaatgaga agacaaagat    47460
tgtcggataa aattaagtag gtttcctaat gtaaaatagc aacctatttt aaatatgaag    47520
acacagaggt taaaggaaa aggatagaaa aaaaatacag catgcaaata ataatcagaa     47580
gaaatgtgaa gtgcctgtat taatataaac aaagatttca gagcaagaaa tatttctggt    47640
gataaagaac attgtgtaat gattaaggaa ttaattcatc aagaggttat aatttttaaat   47700 gtgtaggtgc ttatcccatt tatgcctaat gttccattat tggaacgcta agcatgtggg    47760
agttatttat atcctactgc tcaaggtcat cgccagggtc tgattttgca attcaaaaaa    47820
ttgtaacctc tggcataaat gggttattaa cagagcgtca aagtacgtga agcagaaatt    47880
gatgaaacta aagaagtag acaaatagaa aattgtaatt agagacatta acccctctct     47940
cttttttttt ttttttttttg agacagagtc tcgctctctt gcccaggctg gagtgcagtg    48000
gtgtgatttc ggctcactgc aagctctgcc tcccgggttc acgccattct cctgcctcag    48060
cctcttgagt agctgggact acaggcgccc accaccacac ctggctaata ttttgtattt    48120
ttagtacaga cggggtttca ccgtgttagc caagatggtc ttgatctcct gacctcatga    48180
tctgcctgcc tcggcctccc aaagtgctgg gattacaggc gtgagccact gtgccctgcc    48240 ctaaccccctc tctcttaatt aacagaagaa tgaaacagaa aatcagtaat gatatagaat    48300
gtttggaaaa cactgtcaac cagttgacct aattgagagt catgaaacac ttcactcaac    48360
aacagcaaaa catttactac caaagaccat attctaggcc attaagccag ttttggtaaa    48420
tttgaaagta ttaaaattat tcaaagtatg ttctgtgatc acagtggaat ttaaattaga    48480
aattgataac acaaagatat ctggaaaacc tttgaatatt tgaaaattaa acaatatatt    48540
tctaaataac ccatgggcca aagaagaaaa aacaggggaa aataaacata ttttgaacta    48600
aatggaaatg taacctatta tagtttgttg gatgaagcta aagcaatgct cagatggaaa    48660
tgtatagcat taaacgttta tacaggttga gcattcctaa tcccaaaatc tgaaatctaa    48720
aatgtttcaa actcgtaaat attttgagtg tcatcatgac agctcaaaga aaatgcttag    48780
```

```
gggtgctaaa ccagtaaata taatgcaaat aatccaaaat ccataaaaat ctgaactctg    48840
aaacacatct ggtcccaagc attttgaata aggaatattc aacctgtatt agaaaaaaag    48900
taaagcagcc agactccatc ttaaaaaaaa aaagtaaagc ttgtagctta aaaaattaga    48960
aaaagaaaaa caaattaaac ccaaactaag cagaaggaag aatataatga tgataaatgc    49020
aaaaattaat gaattagaaa atagacaata ggaaaattag tgaaaccaaa gctgattctt    49080
tgagaaaatg aatatagttg ataaatctgt ggccagaatg gtcaggataa aagagataa     49140 ggtgcatatt accagtaaca ggaatgagag aggggacat cactacacgt cctatggaca     49200
ttaaaggata ataagggagt attaagaaca acttcatgcc aaaatattca acaacttaga    49260
taaaatacac aaaattcctt gtaagacata aatgtatggt tctttgactt cacgttataa    49320
tacgttgctg tcctgcattt tgaagtacaa gcctgagatt cttatttgtt agaatttta     49380 acactagagg attagaaaat ctcatcttgc tcttctctct gtatgcttac aagctctatc    49440
agaggattat ctagaattag acgttttcta cacagacctg aagatacaa ccataaggat     49500 ttatattcca gggccgggcg cagtggctca cgcctgtaat cccagcactt tgggaggctg    49560
agacgggtgg agatcgagac catcctggct aacaggatga aaccttgtct ctactaaaaa    49620
tacaacaaat tagccgggcg tggtggcggg tgcctgtagt cccagctact ctggaggctg    49680
aggcaggaga atggcgtgaa cccgggaggc ggagctggca gtgagccgag atcgggccac    49740
tgcactccag cctgggggac agagcgagac tccgtctcaa aaaaaaaga tttatattcc    49800 aaatcaaact ataattgaaa tattattaaa tattgtttaa tctgttaaag acagtaactt    49860
atccagtttt aatgatcctt tgaatctgat actgaatttc catgtgaggt ggttaattgc    49920
tcagtttgat ggcagggtgg ggcagtatat tgattaagag cataggttct ggaagcagac    49980
acttgtctta tttaataatt attttgtggc cgggcgcggt ggctcacgcc tgtaatccca    50040
ggactttggg aggccgaggc gggtggaaca cgaggtcagg agatcgagac catcctggct    50100
aacacggtga aaccccgtct ctactaaaaa tataaaaatt aggcgtagtg gcaggcgcct    50160
gtggtcccag ctactcggga ggctgaggca ggagaatggc gtgaacccgg gaggcggagc    50220
ttgcagtgag ccgagattgc gccgatgcac tccagcctgg gcaataatta gtattgctat    50280
tattattttg ttactgtgct tgtgaccttg agcaagattc taaactcctg aacaagagtg    50340
tcctcatatg taaagtggga gtgataatag tgtctgctac atagaattat tgtgaggatt    50400
aatagtaata atgcttttaa atcttttaac atgatacctg aaacattaag cgcttagatg    50460
ttaactgcta gtatgaatac ctttttatttt tgaaccaaag atttaataaa gcttaagaat    50520
aagttctaag ggaaaaagac agattgatac attgaaatgc tgaataaggc tgtctaaaaa    50580
aggctgtcta aaaagagttc ctttttgcca gaaaaaaga acataatgct tttgcaggtt     50640
tgccagaaaa atatttagct ggaaagagaa gaaaataaaa ttttgtgcgg aggggaaggg    50700
aagggagggt tctttttaag atagagttga atgccaagag tggtaagtaa agaatttgac    50760
ttgctgaaga gaaatctgac ttctctttat tttctccccc agtttcgctt tttcaatttt    50820 aacactttt tgaaacttta atttagactt acaaaaagag ttacaaaaga gtacagagag    50880
ttcctgtata ccattcattc agcttcccctt tatgttaaca tcttgcataa cagtggaact    50940
gtttcttaca gctaagaaat taactgtgac acaatactat aactaaagta caggacgtat    51000
ttggttttca ccagtttttc cgcttcagga tccaggtgag gatccacatt gtctttagct    51060
gttgtagctc ctcagtctcc tccaatctgg gatagttcct gtttttcttt gtctttcatg    51120
acctaaatac ttctgaaggg tactggtccc ttattttgta gaatgtctcc aatttgggtc    51180
```

```
tgtctgttgt gttgttatgg tttgattgag tccgtgcgtt attgagaaag ctaccacaga    51240
agtgatacca ttctcagtga atcatgcgag agactatgtg gttttgatac atattactga    51300
tgatgtaaat cttaatcgct tgtctcaggt gtcagcgggg attttctact accaacttac    51360
tgcttttctc tttgtaatca ccatatattg tggcagagat actttgggac tgtatatagc    51420
attttggatt aaactttcac ccactaactt tagtatgcat ctgtgatctt gcctgtggca    51480
gttattacct tggtgttctt tttttttttt tttttttttt ttttgagatg gagttttgct    51540
cttgttgccc tggctggagt gcagtggcgc catctcagct cattgcaacc tctgcttcct    51600
gggttcaagc aattctcctg cctcagcctc ctgagtagct gggattacag gcacccacca    51660
ccatgcccgg ctaatttttt gtatttctta gtagagatgg ggtttcacca cgttggccag    51720
gctggtctca aactcctgac ctcaggtgat ccagccacct cagcctccca aagtgctggg    51780
attacaggcg tgagccaccg cacccggctt accttggtgt tctaatggtg attttctat    51840 ttttctcatt ctttctatac ttactaatta gaattttttgt gtaaggaaga gttcttgctt    51900
ctcccttatt tatttctgtc gttgtgggtt tgtgaatatt tttattattt ggcttataat    51960
tcaacacaat tgcttctttt ttgttgctcg agttttagtt ttggccattg ggagctgctt    52020
caggtgggta cctgtgtcct ttgaatatat aataacttt tttttttaaa gcattcttat    52080
actttctggc atgataaaat gctccaggat catcttatat tttccctatc ccagttttgg    52140
aattaaccag ttctccaaga agtgctggtt cttttttttg gagaatgata tttagaaacc    52200
aaggtctggg aactaggtgt gtttattgct gaaggagtat cactgcttct caccctctcag    52260 tgactagagc tagaaaatgt atgtatatat gcgaactcat gcatacacac acatctgtgt    52320
gtgtgtgtgt gtgtgtgtgt gtgtgtgtgt gtgtgtgtgt gtgtgtatgc atgcataaag    52380
atttgaaagc caggagtcta ttgatactgc cggctctagt cttctccttt tccttattct    52440
ccttcttctc cttctcctcc ttctcctcct cttcctcctt ttcctcctct tcctcctctt    52500
cctcctcctc ctccttttttt tttttttttt ccccccagac agagtctccc tctgttgccc    52560
aggctggagt gcagcagcac aatttcggct cactgcctca ctgcctcagc cttttgtgta    52620
gcagagattt gaggcgcctg ccaccacgcc cagctaattt ttttgtgttt tcttttagt    52680 agagatgggg ttttgccatg ttggccaggc tggtctcgaa ctcctgacct caagtgatcc    52740
acccaccttg gcctcccaaa ttgccaggat tacaggcatg agccaccatg cctggccact    52800 tcattttaa tctgtacatt tttaaccagg tagctttttt atcttaataa atactatgtg    52860
cataataaaa atttcaaaca caactactgt tacaagtttc ttaagtattc ctttaagaat    52920
attctgtaat aaataagcat gtatatatat agttgacccct tgaacaacat ggtttgaacc    52980
atgcaggtcc acttacacgt tggattttttt caaccaaata tggagcagaa atacagtttt    53040
cagccaggca cagtgtctca cacctgtaat cttggcactt cgggacgctg aggcgggtgg    53100
atcacctgag gtcaggggtt caagaccagc ctggccaaca tggtgaaacc ccatctctac    53160
taaaaataca aatattagct gggcctggtg gtgggctcct gtaatcccag ctagctggga    53220
cgctgaggca ggagaatcgc ttgaatctgg gaggcagagg ttgcaagtga accaagatcg    53280
caccactgca ctccagcaac aagagcaaga ctccatctca cacacacaca tacacacaat    53340
atagtattca tggaacacaa aacccaagta tatggagggc ctgcaggtcc cacagggcca    53400
actgcaggac atgagcatgg atggatttgg ataaatgtga gggtgaggca gttctggaac    53460
caagtcctcc tgtagactga gggatgactg tgtgtctttg tatcttctct cttcttttta    53520
```

```
ttctcgtggg agcatgctat atactttctg caccctttc atctaattgg atattatgag    53580
gctattttg acagagaaaa accttttct gagttgagat ctgacaggtt gaagggcccc    53640
ctgagagatg aagagtaag aactgcagtg aaaaaaaaaa ccaaaccgag atcttcaacc    53700
ttttcttagt tgccttagca gaaactgatg tttgtgtgtt aaagcaaagc ttgtttgggg    53760
attttaaga caaaactgaa gcctacagtc catgctatgt ggggaaaaag ttaataagta    53820
ggatcttccc tggactctgg atatgagtag tagtgagaga atgcaccatt cccacagaca    53880
tgacccatc agctgccatt cccacagat aaacagaaca tgatactaaa actacatgga    53940
attctctcac gtaaagaaac caaacgttt tagagacgga tgtgtcatgt tttagataca    54000
aataaagacc tgttgccata tatctgagta tttacatcag tcatgggact gaagatatta    54060
aattaaaagg ctagaatttt gcatctactt ttaaggtgtc tttacaaaaa acaaatgatc    54120
gtgtacacct ttttcctctt cttaaaattg atcactgtgc tgttgtgcac aatttcctta    54180
ataagataca gctattagtg tttgtggcat tttgtgattt gtgtaactaa cctttcccc    54240
tccagcttct tacctttctg ttcctgtgat gttgcagggt tgcctgattc tgagtgatga    54300
actgaatcat gcatcactgg ttctgggagc cagactgtca ggagcaacca ttagaatctt    54360
caaacacaac agtgagtttg ctgaagaatt cactgctggc cttggtttg ctattctttc    54420
gatccatggt gggagttaac attagttata ttagcacttg aaagtataaa tgaagacaaa    54480
gtagcaacat ttaaaatgtt cttccggtcc agtcttttaa aattagaggt tgatggaagc    54540
ctcttgtaca aatataatac tatccttta tttgaccatg aagttttcca tcccatttcc    54600
ttgtttacag atccgttact caaatacatt tactcgatga ctatagtgta tcttgccata    54660
agactaacag tatttaagtg aataaatcaa gatctctgac tggttaacga agagacttaa    54720
tagataagcc agtccttaca atatagtgga caggtgctga agtacagcta tgaatagatg    54780
ctgtgggagc acagaggagg gtggccctga gccagacctt tcctccctca gtggaaatat    54840
ctttgtgtat tattaaaatg attatttaga ataaaaatgc gtaactttca tagttaaaac    54900
acacacatag gcagaaaagg tgaccaaact gtatgttaat agcatctttt cccaaaatgt    54960
gtacaggcac agacaaaagt ttggaagaat gtataccaaa atgttaggtg tgtacccgtg    55020
gatggaagga tcatagatga taacatcatt tttgtttttg ttttttgtttt tgtcttgtct    55080
aaaatgtttt acagtgagaa atgagatctt attaaatatc actatgtaac ctgttatttt    55140
cttttttttt tttttgaggc tagagtctcg ctctgtcacc caggctggag tgcagtggct    55200
caatcttggc tcactgcaac ctctgcctcc cgagttcaag cgattctcct gcctcagcct    55260
cccgagtagc tgggattaca ggagcgcgcc accacacctg actaattttt agtatttta    55320
gtagggacgg agtttcactg tgttggccag actggtcttg aactcccgac ttcagttgat    55380
cctcccgcct tggcctccca agtgctggg attacaggtg tgagccatca tgcctggcct    55440
cttttacaa tacacggtga ttgttgtttg tcattacatg taactctatc tcattcttaa    55500
ataccagtgt ggcagttagt gcctgggtgt gccctcattt aattgccccc tcaattggac    55560
atcggggctg tttctaaatt tttctactgg gaacagcact acagttacag ttttgtacca    55620
tcatctggtt agtgccttag gataaatttc tagcagtctc agaatgcatg gttaaaagag    55680
tatacatttt taatactttt ccaaattgcc tctaagcatt atatgaactt tttttttttc    55740
acttttattt taggttcagg ggtacatgta caggtttgtt atataggtaa attgcatgtc    55800
tcggggggttt gtgtacagat tatttcgcca cccaggtaat cagcatagta cctgataggt    55860
aggtagtttt tcgaacctta ccctcctcaa cctcccctgc ctcactctca agtagacccc    55920
```

```
agtgtctgtt gttcccttag tcgtgtctgt atgtactcag tgtttagctc ccacttacaa   55980
gtgagaatat gtggtatttg gttttctgtt cctgtattag tttgcttagg gtaatggctt   56040
ctagctgcat ccatgttgct gcaaaggaca tgatctcatt ctttcttatg gctacatagt   56100
attccatggt gtatatgtac atatatatat atatatttt attttattt ttgagacaga    56160 gtcttgctct gtctcccagg ctggcatgca ttggcatgaa ctcagctcac tgcaacctct   56220
acctccccag ctcaaccgat cctcccatct cagccaccct agtagctggg actacagatg   56280
tgttccacca cgcccggcca agtttttgt ttttgtttt ttgtgttttc ttttgtatt     56340 ttttgtaaag atggggtttc accatgttgc ccaggctggt cttgaactcc tgggctcaag   56400
caatccaccc accttggcct cccagtactg ggattatagg cataagccac cacgcctggc   56460
ccacattttt ttaatccagt ctactgttga tggacattta gattgatcct atgtctttgc   56520
tgttgtgaat agtgctacaa tgaacataca catgcttgca tcttgtatga attttcctc   56580 aacaacatga gattgactgt tcctactcac tggccaacat aggctatggt gaatcatttt   56640
aaatctttcc aaatctaatg aggaaataat atgttagttt ttatttcatt gcttattaga   56700
tatagaacaa cttttgcat ttttactgtt tttttaactc tacttgtaag ctaatgtgtt    56760
tgtatttctt tataaattgg ccattttcaa attgtttcta ttttttactg attataagag   56820 cccctttatat taattatctt ttcctttatg ttgcattatt ttattattat tttttgaga   56880 cagggtcttg ctgcatcacc caggctggag tgaagtagca gaaccacaac tcaccacagc   56940
cttgacctcc taggttcaaa tgattctcct gcctcagtct cctgagtagc taggactgta   57000
ggcatccacc accatgccgg actagtgttt tttatttttt atagagacaa agtctcgctg   57060
tgttgcccag gttggtcttg aactcttagg ctgaaacgat cctgctgtct cagcctccca   57120
aaatgctggg attacaggag tgattcacca tgcccagact gcactatttt tatattttg   57180 actttgtttt cagtgtcttc ctgtacagac tcatgaaaat gttttgttg ccacacttac    57240 tgttttacga ctttcggatt ttacacaata ccctcctcat tctcagatca taatgttatt   57300
ctttcatgtt ttcttctggg agttttgcga tatattttt atttaaattt atgtggaatt    57360
tgggggcata acattggaga gattgaattt ttttttctaa gtagataata tggttaagca   57420
ttctgctata ggtatttctt tttttgaaa cagtcttgct ctgtcaccca ggctggaggg    57480
cagtggcgtg atcttggctc actgcaacct ccgtctcctg ggtttaagcg attctcatgt   57540
ctcagcctcc caagtagctg gaattacagg tgcccaccac cacaaccggc taatttttt    57600 tgtattttta gtagagacag ggttttgcca tgttggtcag tctggtctcg aactcctgac   57660
cttaagcgat tcacccgcct cggtctccca aagtgctaag attacaggcg tgagccacca   57720
cacctggctg atgcttcttt tatctaaaat tttgaccagt attatttttc tcctccttct   57780
atatataaac agagaaaact aaaataattc ctgtgttttt acttgtcttc agctgatcgc   57840
catacattgc tctctgccta agaactggag gctttgcagg acttggggag gccaaggagg   57900
gcagatcacc tgaggtcagg agttcaagac cagcctggcc aaaatggtga accccacct    57960 ctactaaaaa tacaaaaatt agctggatgt ggtggcatgc acctgtaatc ccagctactc   58020
aggaggctga ggctggagaa tcacttgaat ccaggaggcg gaggtttcag tgagcagaga   58080
tcacgccact gcactcctgc cttggcgaca gagcaagact ctgtctcaaa aaaaaaaaa    58140 caaaaaaact ggaggctttg agtcaggacg taatttactt ctgtagggaa catctcctga   58200
atcttgatta ggtcgtatgc agattttttt cttagaaatt actgaatgtg taagcacagt   58260
```

```
cacaacccta gactatctta tttgtgtttg tgttctgtgt ttttattacc ttatctcttt    58320
ttctgtcaaa attgtttttct gcaaagagca aaatcatgta cttttataac tccttcctcc    58380
agttacaagc aatacagaat acaaaatcag attttatgat agggccaggc gtggtgctca    58440
cgcctgtaat cccagcactt tgggaggccg aggcaggcgg atcacctgag gtcagaagtt    58500
caagacaagc ctggccaaca tggtgaaacc ccgtctctac aaaagtacaa aattagcctg    58560
gcgtgatggc gggtgctggt aatccgagct acttgggagg ctgaggcagg agaattgctt    58620
gaaccttgga ggtggaggcc tcagtgagga gagatcacac cattgcactc cagcttggat    58680
gacagaggga gactccatct caaaaaaaaa aaaagattt tatgatagga tgtctcccac    58740
ccctattaag tattccccag acttaatgtt gcttaaattt ggggagttt ttttaagga    58800 cttcatttca gggcaggtat tttaagtatg aaatctgtag tgtggcaaca atggtcttca    58860
aagcatttgt ctttaacaag gaaattatga tcatcattaa tggcagtagc agccaagttg    58920
tttccaggcc cattaaccac cataagaacc aacagagcca caagaacttg gttgtttatg    58980
gacaactgat gaagtcaaac atggaacaat ttcaactgat tgtcaggctt gcttaacaca    59040
cagacttata catgccccag acgggtgtat ttttaaccca gtaccaaaat aaaactcttt    59100
aacaagcgtt tattgagtac gtcctgggtg aaaggaaatg gagcacgcac tgtgaagttt    59160
ttttacgcct tgcgtttgtt tttttaggag gagtatgtgt ctgtgatggt ttattcacac    59220
tctctcgctc tgtctttttt acgcattat ttccgaatga ctcactggga ttagagatac    59280
agtttgattc tgtattttc gataaacaca cagaagctaa cttaatggca gggtatttaa    59340
catgagacac tggtcatttt ataaggaagc taatgaactg agttagccac caccgtcctt    59400
tagtcaagtt tcgatggttt tgaacatttg ttacattttg gatttcaatt caaggtggca    59460
ataattcacc tattttgccc tgcttttttc tgcccaactc taattatgtc ctttgctatc    59520
tgaggcatgg tttctgaatg agaaatatat ctctgcattt ccggaataaa gttaggaaag    59580
aggaagatgc ggtataactg ttcttttttg tgctctgtag atatgcaaag cctagagaag    59640
ctattgaaag atgccattgt ttatggtcag cctcggacac gaaggccctg aagaaaatt    59700 ctcatccttg tggaaggaat atataggtaa tcctgcttta ttattcttac ctttgtgact    59760
tggccccatg aagtcataga attttttaac tgaagggaac attagtctat cccctctgg    59820 aaactaagga gacagtgttt ataagtcgct aaaatacctg gaaacagagt cagcattaga    59880
acagaagtct ttttgtctag ttcttcgtta ttctttccat aatactacat ggtcaccaaa    59940
tcccctttct atttgagtct tttatttttc tagtttgtag agggaaccta tatgtagggg    60000
caagaattgg aatatatatt ttaatatgtc aaaacaaatt acacaccatt taattttaat    60060
aaatatttta ttttaggctg agtgcagtgg ctcacgcctg taatcccaac actttgggag    60120
gcaaaagtgg gaggtcgctc gaggccagga atttgagacc agcttgggca acatagtgag    60180
accctgtctc tgtaaaaaat aaataaaaat taaaagaaa tatttattt tggttaacct    60240 ttacagcttt tacacgtatt tttaccacct aatttttttt gttcttttgt gtcattttaa    60300
ttgcctgtgc aacgtgatgc aaagtctcat gttgcctgta attacaagct ttagaagaat    60360
ctgctgtgac cttaattatt tttgtcgtga attaagattg cttgtgtttg gtgcttgttt    60420
tttgtttttt ggtggtttgg gtggcttttt ttttaagatg gaatctcgct gtgtcaccca    60480
ggctggagtg cagtggcggg atgtcggctc actgcaacct ccgcttcccg gttctcctgc    60540
cttagcctcc cgagtagctg ggattacagg tgtgtgccac caagcccagc taattttgt    60600 attttttagta gagacggggt ttcactgtgt tggccgggct ggtctcgaac tcctgacctc    60660
```

```
aagtgatccg cctacctcag cccaccaaag tgctgggatt acaggtgtga gccaccgcgc    60720
ccagccagtg cttgttttaa aagtccagtt ttctttcccc tagtcttttg ccttgccatg    60780
gcttcatcta cctttgtcag tttaagccac agatacagtt gtcagaccat ttaaaaccca    60840
ataaactcag ccgggcaggg tggcttattc ctgtaacccc agaactgtgg gaggccaagg    60900
cgggtgtatc acttgaggcc aggagttcga gactagcctg gaaacatga ggaaaccccta    60960 tctctactaa aaatacaaac attatctggg cgtggtggtg gcgggcacct ctagtcccag    61020
ctacttggga ggctgaggca caagaatcgc ttgaacccag gagtcaggga ttgtagtaag    61080
ccgagattat gccactgcac ttcagcctgg acaatggagc aaaactctgt cccaagaaaa    61140
aaaaaagaag cagtaaactc aataataatg aagtgccaaa ctcccaattt tgatttaaaa    61200
agtctcagtg tatatgtgta tatatatatt ttttcatgtt ttgccagcat ggagggatct    61260
attgttcgtc ttcctgaagt gattgccctc aagaagaaat acaaggcata cttgtatctg    61320
gatgaggctc acagcattgg cgccctgggc cccacaggcc ggggtgtggt ggagtacttt    61380
ggcctggatc ccgaggatgt ggatgttatg atgggaacgt tcacaaagag ttttggtgct    61440
tctggaggat atattggagg caagaaggta acgagccat gagaatgagc gattagagat    61500
aaagtcactg gcaattagat ttggtacctc aggcctagca gatgggccc tgaactggga    61560 tgtccgcaaa tttgcctctg gtttaggctc ataataccag tgagtgactc taatgtctcc    61620
tcactgaact aaaggctggt tctgttcatt gtttgttgtt ttcttatttg agcttctttc    61680
taagctacat gctgatctga gatatagaat accctcttgt gtgaaagaac acacagtggt    61740
gctccctgcc cgccccagcc ttctgttggg tttgcattgt gctcacagtt tcaaaaacag    61800
tggggttgtc atgggagccc atgggaatag caggtcacct tgcccttgga cacaaatata    61860
tcatgagtga acatggagac aggaagcaaa aaagttgtgc cagctgtggg gtactacaaa    61920
gcattgtatt tttcaatttt taaactatga agttgccttt tctgggtctt tgtagtcaga    61980
aaaaaatcat acggtgaatt ttgatgcagg taagaatctg tggtgtggtc gaaatggtga    62040
accataaaga cagaggcctg ggtctgaata ttttctcggct tactttgtta gacctcaggg    62100 aaaacatttta acctcccagt ttccttgtca gtaaaatgga gataaatatg cccagcttgt    62160
aagattgtag taagggttta aaaagtaata tatgtccatg ctacaacgtg ggtgcacctt    62220
aaaaacatta tggtaagtga aaaaagtcac aaaaagtcac atattgcatg ttttaaaata    62280
tgtgatacct agaataagca tagaaacaga aagtagatta gtagttgccg gaggcggagg    62340
ggatagggaa atggaaagtg aatgctaatg ggtatgaggt ttcctttcag ggttatggaa    62400
atgttctaaa attagtggta aaagtggcac aactctggat atactaaaaa ccactgaatt    62460
gtgctttaaa acggtgaatt ctgtgtatgt ggcttatatc acaatgaagc tgttattttt    62520
aaacgttgat tgcaatgtta gggaaaaaat aatgtatgtc aggtatttgt atatggcaca    62580
gaggaggtgc tcataaatgt tcttaatttt gcttcaccac tcaatattcg gagtattaaa    62640
gaatggttat gctgggcaca gtagctcaca cctgtaatcc cagcactttg agaggctgaa    62700
gtgggaggat tacttgagcc caggagttca ataccagctg ggcaacatag tgagacttca    62760
tctctacaaa aaagtaaaaa aattagctgg gtgtggtggt ggcacatgcc tgtagtccca    62820
actatggggg aggctgagat gagaggattg cttgagcctg ggagatcaag gatgcagtga    62880
gccgtgatta caccactgca ttgcagcctg ggcaacagag caagacccta tcacagaaaa    62940
aaaggtcatt ctttttaatac ttgattgcct gttagagaga actcatttc agtgacttttt    63000
```

```
aatcagcttt gatagatttt ttttttttttt tttttttgag accaagcctt actccattgc    63060
caggctggag ttcagtggca caatcttggc tcactgcaac ctccgcctcc tgggatcaag    63120
cgattctcct gcctcagcct cccaagtagc tgggactaca ggcacgtgcc accatgccca    63180
gctaattttt tgtatttta gtagagacag ggtttcaccg tgttggccag gatggtctcg    63240
atctcttgac ctcgtgatct gcccgcctcg gcctcccaaa gtactaggat tacaggtgtg    63300
agccactgca cctggccagg tttgatagat ttttatctca aatattacct ttttgttaat    63360
gggaccaggc tcactttgga gagttgtttt ttagtaagct ttgtggctgt gaaccaaagg    63420
atagaaaaat aatactctgg gagatcatta aagtacaata tatttgtgct tttggttttt    63480
ttagtacaat ttttaatatt tttgagataa aactgtttca tagccacatt tgtgtccccc    63540
taatttgttc tggtacataa gcttcttgtg tgtgcatttt aaagatttgg tgaaattaaa    63600
agatatcaga gaatagggat atacaattaa gttttttga aatccttgta aatgacagag    63660
ttttacttta ttcagtgaga tgtcattggc attttaataa aataccttgt aagtttctat    63720
ttcacattta tatcatttta tacatttctg catatctgga ggaagttcta atgctcttaa    63780
agttgatgtt agagaactgt tatttagggg tagaaggatg ggctttatag gcacacagag    63840
ctgcagatga cattttctgt gatacttgga attaaatcat tatatctaaa aagcaatcca    63900
aacaccttgt ttaattcagc tgtgttcatt tatttttaac tttttttttt ttttttttt    63960 taagacggag tctcactctg tcccccaggc tggagtgcaa tggcgcaatc tcagctcact    64020
gcaacctccg tctcctaggt tcaagcgatt ctcctgcctc agcctcccaa gtagctggga    64080
ttataggtgc ccgcctccac gcacagctga ttttgtatt tttagtagag atggggtttc    64140
accatgttgg tcaggccagt cttgaactcc tgacctcagt agatccaccc accttggcct    64200
cccaaactgc tgggattaca ggcatgagcc accatgcacg gccatatttc taactttaaa    64260
tgatacattc tccaaattta gaggggttgt tttaaaacta gttttctct tatgttgttc    64320 catgtttaaa aaacaaaacc aaacctaaga actttgccat gtttctgacc cagttgttgc    64380
cagcggtatg cttcgaccat gttggttgac cttgtatctc agattagtgt ccctattcca    64440
gtgccattga agtgaggagt cctctagaac ttagaaggaa aggactgaca ttgccggtga    64500
atgcaagaat tgtctctact tatctgcctc tgtgaactcc ccaggagctg atagactacc    64560
tgcgaacaca ttctcatagt gcagtgtatg ccacgtcatt gtcacctcct gtagtggagc    64620
agatcatcac ctccatgaag tgcatcatgg ggcaggatgg caccagcctt ggtaagtctt    64680
tcttttcttg aaacattgca taagtccacc tagcagccaa acgtgctgtt tttcttgagc    64740
tttttcctta aaataaatag tcaggtttac taataggcag agctggctgg tgtgtggttt    64800
ccatggacac tttttagtg tgtttgatac atatgccatg agaacgaccc tggctcactt    64860
tctatggaat tttcttgttt atagatggga ggctttactc ttactatcct acatacccctc   64920 ttaactcaga ggtaatatac cttcgaggtt tttcttgaat tacataattt tatgtgaagg    64980
tataattcac tgttagtgat gttttcattaa cagcatagtt aagagctgct gttttcataa    65040
attagtattc ctgattaat gcctttttaa agagtttcta ctttcatata cggtagataa    65100
taaatgacat cctgaatcag tttatttgt ctttgatggg attgtagtc ccaactagat     65160 gccttgattt aaacatacta ctgtgaacag tgaagttcag tgttcactt ctgacatttg    65220 actttattc tgcaacacca gagggcagta ttgactgcag aacagtggta ctaaaagggg   65280
agcaactggg tgtctgtctt tactttaaaa aatatttca ttgcatgtat gagacaataa     65340
tttcacttgt cgcttttttt ttttttttt ttttttgaga cggagtctca ctctgtcacc    65400
```

```
caggctggag tgcagtggtg tgatcttggc tcactgcaag ctctgcctcc cgggttcaca   65460
ccattctgcc tcagcctccc gagtagctgg gactacaggc gcccgccacc acgcccggct   65520 aattttttg  tattttaat  agagacggga tttcaccgca ttagccagga tggtctcgat   65580
ctcctgacct cgtgatccgc cctcctcggg ctcccaaagt gctgggatta caggcgtgag   65640
ccaccgtgcc cggcccagtt gttgcttttt taatgcttgt aaagtcagtt tggcatttgt   65700
aaaagatttc acattatcag ccatgagctc tccactctac agttatgtaa tactttattg   65760
taagattgat ttggcttgca tcgaataaag tggcacatct gattttggtt ggtttaagac   65820
tgttttcttt ctttctttt  ttttttttct ggttttttgtt tttgagacag agtcttgctc   65880
tgtctcccgg gctggagtgt agtggtgcga tctcagctca cagcaacctc gcttcccag    65940 gttcacatga ttctcctgtt tcagcctccc aagtagctgg gaccacagga gtctgccacc   66000
acacctggcc atttttttg  tatttttgt  agagatgggg tttcaccatg ttgcccaggt   66060
tggtcttgaa cccctgggct caagcagtct gcctgcttg  gccttccaac gtgctggaat   66120
tacagctgtg agccaccaca cccagctgac tgttttcttt tcttttctt  tcctttcctt   66180 ttctttcttt tgagatggag ttttgctctt gttgctcagg ctggagtgca atggcatgat   66240
cttggctcac cacaatctct gcctcccagg ttcaagcgat tctcctgcct cagccttccc   66300
gagtagctgg gattacaggc atgcgccacc acacccggct aattttgtat gtttagtaga   66360
gaccgggttt ctccgtgttg gtcaggctgg tctcgaactc ccgacctcag gtgacctgcc   66420
tgccttgact tccaaaatg  ctgggattac aggcgtaagc caccgcgccc agtcgactgt   66480
tttcttaaat cagaattta  ccttaacatt ttttctgatc tgtgctagat ccttgttatc   66540
tctaatgaga gatttttgga aatagtgaaa tgtgatcatt tcagttttg  tgaattaatt   66600 ccttgaagaa gttgttttat taatgttgca aacacatagt ggagcctgtg aatagctccc   66660
tgttaataac agctatatct cctctccttc tgatgtggtg ttagtggaaa ctgtgtgtga   66720
atctgagaga cagacatata tacacacata tatatacata cagctagcat ttctctaggt   66780
acttcacata ggcacactta ccttactgat tcagcacaca ggtttaggtg actaagaaat   66840
ggctaagagc tatcaaagtt aacattggat aatttatttg ccctgttcca gaacatggat   66900
ctgtgtgaca cattaccccc agataaatga cttatctgta ctaaatgatg aaatctgggc   66960
tgtgctagta gtgagaaaat gaaacatggt aattatatat aggctttgga tcagcacaag   67020
ttttctagtt tttgcctcta gccaccccca aagcttagtg atgtgacaca acagccatct   67080
gattatgctc acagatgcca caggtcaaga attcggtcag ggcacagcag ggatgacttg   67140
tctttgctct gttgtctggg gctggcctgg aagactcaag tgtctggaaa gactgagatg   67200 gttggtggt  gggatcatct ggaagctttt ccactcacat gtcacctggg ctggagtgac   67260
ttggagccag gctcagctga ggctgttgac cagagcacct tcatgcatgt atcttttcaa   67320
tgtggcttag gctcctcatg acatcgtgac tgtgtaccca gaaaggatgc ttcagagagc   67380
aagcattcca aagaacctgg cggaaacccc atgaccttt  ctgacctgtt gttaacaagc   67440
aggtcactaa ggccatcccg gattgaaggg gtggggaact agattccacc tcccagtgg   67500 aggcatgtca aagaatttgt ggctggtttt tttttttg  agatgcagtc tcaaggagaa   67560
gtaccatgct ttttaaaca  accagatctt gggagaactc agagcgagaa ctcactcatt   67620
acccaaggat ggcagcaagc cattcacgag gatcctcccc atgatccaca cacctcccac   67680
caggccctac ctccgtcatt ggggatcaca ttccatcctg agatggacaa acatccaaac   67740
```

```
catgtcagtg aatatattac atttatcatt aaaactttgt tattgttgga ttccagagta    67800
cattaagtac ctggtattga aagtaaggct taaacatgta tatgtggttg cttattgtta    67860
aatgttttca tcttttttgtg tgaagaaatg ttgctctttg gtgagagtac agagccttca   67920
gaaaagctgc agcatgtaag ggaaggtgag atccagtttc cacacgactt tgtgagcgct    67980
cctttcccct tcctcccaac ttttttccgca tttcccctcc agtttctatc cttttcccaa   68040
ggaagaacag gacatatgac taggttgaca gatcttgaaa ggcaacttca ctaggatctc    68100
aggtgagata ataatgaatg ggaattgtgc tgccaggatg cctgtacctg gagtgggaat    68160
actgagcaca ggccagggag tagaaaaaat gaggcctagg aaattctgtt aaattccact    68220
agacatttga aattctaact tttactttac acatcactaa tccgtgtcca ctaatggaaa    68280
tttagctgta gtatctacat acgaatcaag gcaaagtgtt tgaccaaatc aactaaaatt    68340
ttgcttttcc attttccaga gctgtgcttt gatgtatttt atttctgtcc aaaggtgtag    68400
ttaataataa catgcatagc acccagctta gtgtgtgaca tctaggatcc tttcagtaaa    68460
tttattgaat gactgaatga atgcacgcat gattggcaat accagaaaat cagtgggttc    68520
ttcaagtact ttattgtaac attgcttgaa tagttgaatg ttaagccaga atgaccaaat    68580
tatgaaacca aattaactag ataggtacat tttaatagat acattttaa ataatgtcag     68640
aacgctttat agagttttgt acttctttgt tttgaaagga actgggtcct tgcaggcagc    68700
tactgatgta ggagaaaaaa gactaccctg agcagattga ggtttaatta aaactaggtt    68760
tggctcattt gaattaattc cagtaataga cttgttaatt aggtgttaaa tgatcacctt    68820
gagaataccg gggaactgtc aaaaactaag agaactgaga cacttaaaaa aaaaaaaaaa    68880
aaaaaaaaaa aagacattcc aggacaatgc agtggcacat gcctggagtc ccagctactc    68940
aggaggctga ggcacgagga tcgcttgagc ccaagagtcc tgggctgtag cacactgtgc    69000
cagagacgtg tctgcaccaa gttcagccat cagtatgatg acctcccaga gtaggggac    69060
caccaggttg cctaaggagg ggtgaattgg cccaggttgg aaacgaacag gttaaaactt    69120
cccctgctga tcagtagtgg gattacgcct gtgaatagcc actgcactcc agcctgggca   69180
acatagcgag accttgtctc tttaaaacaa aacaaaacaa aaaaacattc caagattccc    69240
atgcagaagg gttagaagtg ttgaaaaaac acagccttgc tgggagggggg tcataaagag   69300
agactttcct gcctgtcttc agggctgaca gcttttaacc ctcccgtcaa gcaccatact    69360
tcctgagccc aagaacgttt gggtgttgac tttcttcttt gttgtgcttt aaagtaattt    69420
atttcactat tagaaattca tcgaaataaa aattaagttt tctggtaagc acagttttgt    69480
tcttacccac agtagagttt agcagtttat ctgatgctgg gaatcagact cgcttcctcc    69540
tgttttgtga ctttctgcct agaatgctgt tgtttggaaa aaaaaaaaaa aatacttgtt    69600
tccgccgggt gcgatggctc acacctgtaa tcccagcact tgggaggcc gaggcaggcg    69660
gatcacctga ggtcgggaat tcaagaccag tctgaccaac atggagaaac cctgtctcta    69720
ataaaaatat gaaaattagc tgggtgtggt ggcgcatgcc tgtaatccca gcactttggg    69780
aggccaaggc aggcggatca cctgaggtcg ggaattcaag actagcctga ccaacatgga    69840
gaagccctgt ctctaataaa aatacgaaaa ttagctgggc gtggtggcgc atgcctgtaa    69900
tctcagctac ttgggaggct gaggcaggag aattgcttga acacaggagg ttgcggtgag    69960
ctgagatcgc gccattacac tccaacctgg gcaacaagag cgaaactcca tctccaaaaa    70020
aaaaagtgt tttaccattt gttaaacact tatcaagcaa caagcaacta ctctctacat     70080
agtggtagat atgctgtgtg ggagatgcag agttgaacaa taggtgatct ttgcctttga    70140
```

```
aaaaacagtc cagtggtagg ggtaagattc ccgggaagaa ctagtctcag aggcacagat   70200
aaattcttcc tttgttcagc ttgtcttttc tcaatttcct cctccattct cttctacaac   70260
ctcctccttc actcactccc actcccctaa aaccttaaac ttccttaaac cagctaagtt   70320
tttgaagcaa actcatattt tagatttctt atataataac tttctatata aatgaaattt   70380
ttctgtggat actgtcactc tagtaaatta tcagcaatca aagcagcttc ttgattattt   70440
tttaaagcag cttcttgatt attgagcaca aaaggccttt taaccaatgg cttaagcctt   70500
ctgaaatcag caagcaatat gaccacctta caggtggaga aatttgagct catgtatgga   70560
acaagttttc tcaatatctt gtctccaact agaatgtagc ttttctaact ccatctgctt   70620
ctacttctga ggttgcatga tgatagttag cattttatta aaacagacta ttttataatc   70680
tgtttctaat tttctgctaa ttttccaaag tttaattgtg agtaatcagc ccaacaaatg   70740
aaagctcttt tgggcatttg cctccctgtt ttctctccat ggatcagtag ccctttcccc   70800
acctttctgc ttcagaaatg gattctgaat actcaagagc ttttgcaaca tggtgtgtct   70860
attttttatt ccactgctat ctttttcttc caaatccaaa tgctattaaa agtttcttgc   70920
aacaagaaca ttctctcctt ttgtgcctcg tttcagagtt agtttgaagc tagcaattag   70980
gatgcccagt gtctattgtt tgttgaagaa taattctaac tttctaaacc ttcacataat   71040
tggaattgct tttctccccc cagaattatg tctgagggct ttatttttca tcaaatagac   71100
ttgatcctag ctgttcccca actttatagc agatacttaa tatgtataaa ccagtgacct   71160
gatagatgga atctgctcaa agtaagaacc tgatacccgg ccgggcacga tggctcacgc   71220
ctgtaatccc agcactttgg gaagctgagg cgggtggatc acctgaggtc aggagtttga   71280
gaccagcctg accaacatgg cgaaaccctg tctctactga aatacaaaaa aatttagcca   71340
ggcatggtgg cgcatgcctg caatcccagc tacttgggag gctgatggag gagaatggct   71400
tgaacctggg aggtggagat tgcagggagc cgagatcacg ccattgcact gcagcctggg   71460
agacaagagt gaaactccca tctcaaaaaa aaaaaaagtg cccgataccc tactaagagc   71520
ttgccggatt tgaaagcttt ccaaaaagga attgattttt ttttaattgt cacctatagt   71580
ttttctaatt atctaaatat tttatttgta tctacctccc tgctatctac tttggcagta   71640
gagtgaggtg ttaaagaaaa aattattcct gtcacttgtg aaacatgata agacagactt   71700
ccttcaaggg ggccatggta ataagcatag ggatgactgc aatgggtct tccagtgggg    71760 gagagagggt gggctgcagt ctgactccaa taaggacaga tgaggattta cagccaagga   71820
acagggtggg agtgagtaga tagaaaaata ctaagaggaa acatcagggg taaggggat    71880 gcttgccttc agcattcttg ttgaaggtag gccagggtga taagatacca ggggtagtca   71940
tgtaggggat tttctctaat ctgacttagc aggattattg ctcaaactgg attctgcaag   72000
aatggagaag gaggcgcaac gtcaggactt tatcagaaag gactccaaga ggagcctgac   72060
tcaagtttgg tcaaggaga gagtctttgt caggttcaga atgacctcat taacatgaac    72120
tctttaagcc cctgttctca gactttgtcc atggaccacc tgcatcagag gtacttttag   72180
tacagtggtt cataccttgc ttacacacag gaaagcttaa aaaaatagtg ccagtgttag   72240
agaccttctg tagacccatt gagtatctca aggcgaggcc tccctgccat ggcatggtgt   72300
tatttaaaag caccccagat gcttctcatg taaggcccca tttcagaacc actgctgctt   72360
gttaaaaatg aagattctag tttgttccac ccaccctact gagtcttggt ggatgaggcc   72420
ctagaatatg cattgaaaag aaaaccttag gctggatatg gtaatcctga cattttggga   72480
```

```
tgtaatcgta acattttggg aggctgaagc tggaggatca cttgaggtca ggagtttgag    72540
accagtctgg gtgacatagt gtgagcctct gtctctacaa aaaattctaa aaattagcca    72600
agtgtggtgg tacacgtctg taatcctagc tacttgggag gccaaggcgg aggattgcac    72660
aaacccagct atgatcacac cactgcattc cagcttggat gagagaggga aaccctatct    72720
ctagaaaata aaaagagga ttgtcttttt gacaatcctc ttttttttcct tttaacttttt    72780 ttacctcagt accaaagcag ctctactgat tgatggtaat tgaaaaagga aaagaaactg    72840
gaagtcaaga tacaaatgag ggagatgttt ggcttgtaag acaggcattt gctggcagag    72900
ctaagttgcc atttttggtt gtttctggaa ctctaaatgc ctgggatgct gacactccct    72960
tctgaacagc tgatgattct ggctgattga atcagtggca taggtggaga agttagaaac    73020
cagttaggtg cagcaggaaa acagaactaa gcattcagag atctgtggtc atggttccta    73080
aggctagttg gaattaatta tttttgtttt acttttttttg gggggggctg cttgtatttt    73140
tataacctat taatcctcaa attacttagt acataaccta caaatggcct tgcccactat    73200
aaagttgtta aaatgtttag tattaaccgt tttgtaaaac tctgattgtc ttattgtatt    73260
gccttctacc tctaaaactg ttaacttaaa tccaagccaa gcctttacca gagattacct    73320
ttatttgcta gctgtcttca tctgtgggta gatacattac tacagtgttt acgttcctta    73380
tctctttgtc tcagagtagc ctgtgatatg ttccagcccc aacagaggac agtagaatgg    73440
tccattaaga ctttctgagg ccaaggtggg cggatcactc gagatcaaga gttggagacc    73500
agcctggcca acatagtagt gaaaccgtgt ctctactaaa aatacaaaaa ttagccgggt    73560
gtggtggtgc acgcctgtag tcccagctac tcaggcggct gaggcaggaa aatcactgga    73620
acccgggagg tggaggttgc agtgagctga gatcgtgcca ctgcactcca gctcaggcaa    73680
cagagtgaga cttggtctca aaacaaaca aacaaaagac tttctgtcct gcctgtgggt    73740
tggcacccgt taaaactcag ttccttgatt tttcacaggc acttggcctc ttttctgcct    73800
tttgtggagg gccctctgtt tctggctgtg cattagcaac cattcttta aacttctgat    73860 tatattgaat cagcaacttt aagcttgccc ctgctgcttg tcatacatcc tgtggcagtc    73920
ctcaggaaat cctagttttt ggcattgaaa tgaattaaag gattaagcca caagagggtg    73980
ggggtgataa actgtgcttt taagaggaat ttactgtgca gtacttggtg ttagcaaaag    74040
cagttctagt tcttacaggg agataggaaa ccaaggggct gctttagaac agcatcccta    74100
ggatatgaag acgcagatct gtctgctttg atgttcttta gcttgacagt ggccccggct    74160
gagcactttg atatttgtcg ccagtctagc aaaatagggg ttgtgtcttg gagatggtaa    74220
acctagttcc cgttgctttg cttcagtgtt agaaaattac tgaactcttg cttcctggaa    74280
gtcccttata aatctcccctt ttacaagact gttctctggg gcacgaaaat gcctttgctt    74340
ataaagagcc tgttgaaggt ccatttattt tccttttctt aacagaaaga ttttccagtg    74400
ccatttagtt aggacttacg ggaaacatgt tgttaaaatc aatctgtcct gttagctaat    74460
atttctttta ttttcatttt gagcttttag ataagattct ttatctttct gtgagataat    74520
gtgaaaaaaa acacaaaaga aataaattca aataccagta tactctggtt tttaaaaata    74580
tcttcactga cttttttttt ctttacatgc tctactctcc ctctcaccct acttccttct    74640
tcacttttca cttggtactt tcagatattc tttgtgggtt tttcttggtt tttttttttt    74700
tttccggaca cagagtctgt ctcactctgt tgcccaggct ggagtgcagt ggcacaatct    74760
tggctcactg caacctccgc ttcccaggtt caaaccattc tcatgcctca gcctcctgag    74820
tagctgggac tacaggcgcg tgccactatg cctggctact ctttgtattt ttagtagaga    74880
```

```
cggggtttct ccatgttggc caggctggtg tggaactcct gacctcaggt gatccacccg   74940
ccttggcctc ccaaagcact gggattacag tcttgagcca ctgcacctgg cctagatatt   75000
cttagatata ttcatgatgc atcccatcta gatgcttgtg atgagtatat aatttactga   75060
tctggaaagt gtgacaagag tttaaagtgt tatctgctgc cttctccccc cactttagag   75120
ctgttcaaag aaagtgacca ttgatcattt taaaagatga gcaaaggaaa gactgcttct   75180
tttttaaaaa agaaaatttg atgacctact gttagaacac atttccacat ggaccccccg   75240
cttctaaatg ggtgtatatc cagatcatcc agtctgtgtg cacagagtcc ttgcatttct   75300
aagttcaaaa tagtaattta aatgaaagta ggccatcata aggcattgct aggaagaggt   75360
tactcttgat agatgaatgt gctgcttttg gtaagaatta gtttgttatt tatatttaaa   75420
ttttgtaggc cgggcctggt ggcttaaacc tgtaatccta ccattttggg aggccaagac   75480
gggtggatca cttgagccca ggagttcaag accagcttgg gcaacatggt gaaaccctgt   75540
ctctacaaaa aaataaaata aaatacaaaa attacccagg catggtggct tatgcctata   75600
gtcccagcta cttgaggtgc tgagacagga ggatcacttg agcctggcag gcggagattg   75660
cagtgagctg agatcacacc actccagcct gggtgacaga gtgagtccct gactcaaaat   75720
aaataaataa ataaataaat aaataaataa aatgttttgc aagcatacct tctgagtaca   75780 gttacactt gccttattct tagattttac atgttacaca tattttggt tctgtgaaca   75840 gattatatat ggcatatttg tagttctaaa ctacttctgc aactaaacat gcattatatc   75900
actcatttcc cctcagtgga actggtatat atggacttat gccataatta aatgttagca   75960
atgagagaga tctacccttta aaataataaa atgtgctggg tgcggtggct cacgcctgta   76020
atcccagcac tttgggagtc taaggtgggt gatcgcttga ggtcaggagt tcgagaccag   76080
cctggacaac atagcgaaac cccatctcta ctaaaaatac aaaaattagc caggtgtggt   76140
ggcggccgtc tgtagtccca gctactcggg aggctgaggc aagagaatca cttgaaccca   76200
ggaagcagag gttgcagtaa gccaagatca caccactgca ctccagcctg ggcaactgag   76260
caagactccg tctcaaaaaa tttaaaaaat taaaaaataa aagtaaaaat aaataaaatg   76320
catttcaaaa tcaaatggag accatttctt gatgatctgg gctgctgtgc cttcctcttc   76380
ctgcatatgc acagctaatt gagaatgtgg tgttaaattt attagcagat aagaactctg   76440
tccattacat ttttttttgta tgtttcaggc cttttaaggc atattattcc tttattgctg   76500
tctgatcttc aaaacatatc cagaggacct tcttattact tttttttttt tttttttttt   76560
tgagacaaga gtttcgctct tgttgcccat gctggcaggc tggagtacaa tggcacaacc   76620
tctgcttacc gcaacctccg cctcccaggt tcgagcgatt ctcctgcctc agcttcccga   76680
gtagctggga ttataggcat gtgtcaccac acctggctca ttttgtattt ttagtagaga   76740
cagggtttct tcatgttggt caggctggtc tagaactccc gaccccaggt gatctgcctg   76800
cctcggcctc ccaaagtgct gggattatag gcatgagcca ccttgcctgg cttaattgtg   76860 ttttttatt agttcaagcc acaataagaa gtttattcag tcagcaatct gtttttgact   76920
acttaaccac gtgccagcta caaaaaaata acatatagct tcaaaagcct cttaagcggc   76980
tgggcacagt ggctcacgcc tgtaatgcca gcactttgga aggccaagac tggcagatca   77040
cttgaggtta ggagtttgag accagcctgg ccaacatgac aaaacccccat ctctattaaa   77100 aatataaaaa ttagccagac ttggtggcag gcacctgtaa tcccagctac ttgagaggct   77160
gtggcaggag gatcacttga gcccaggagc cagaggttgc aatgaaccga gatcacacca   77220
```

```
ctgtactcca ggctgggcga cacaacgaga ccccatctcc aaaaaaaaaa aaaaaaaaaa  77280
aaagcctctt aagataaaat tttcatttttt ttgaattctc agaataaaca acagtttctt  77340
agtgttagat tacaattatt tcttaatacc acttagatcc ttcttttttt aattaatttt  77400
ttctctttt ggtgtctgag tgggccttag agttagaaaa taactgtctc ctgttggctt  77460
gccttttctc tttttcctca aggtctttaa tatctcccta gaagataaaa aggatatatg  77520
cccatttgtt tctgtttttt cccaatttga tgatagaaga ataggcctta aaatattata  77580
ggtcttgtta taggtaaaat aacaaaaata gaaaataata taaatgatct tacatatgta  77640
aatataaaat aagttttaa agaccgtttg tttaagcatt tcattaagtg ctttaatgga  77700
gtatcccatt ttcttaaaac agccttatct agtaggtagt tatcatcatc atcatcatcc  77760
ccattgccat tcccattttg cagatgaaga aaccaaactc agaggttaag tgacttggct  77820
gtagccatac agctactaga tgctcaagcc aggatacaaa cgtagatagt ctgacttcag  77880
aagtttatat accacaggct ggggatagtg gctcatgcct gcaatcccag cactttggga  77940
ggctgaggca ggtggatcac ctgaggtcag gagtttgaga ccagcctgag caacatggcg  78000
aaacccatc tctactaaaa atacaaaaat tagccagatg tggtgacgca tgcctgtaat  78060
cccagctact tgggaggctg aggcacaaga atagtttgaa cccgggaggc agaggtagca  78120
ttgagccaag atcaagccac tgcactccag cctgggcaac agagcaagac tctgtctcaa  78180
aaaaaaagtt tatatagaac caaattaaaa ctactaataa gtgaaattca ggaagatggt  78240
gaaattatta gttctctctt tcttctgag acctgcatta ctgctttgat gtatgacatc  78300
caaaatgact gtcttattat ttcaagttta aaatgtcctc catgcaagca tatctctgtg  78360
cctattctag attattagat gtgagaataa aattagctca ggtagagaca ggatcccatc  78420
cccattatga tggggtgtgc atgagtggta gttttcagaa aaggacggtg tctgcttgcc  78480
atcttgaaca ctcagatttg caaaggtaat ttgcctcacc tggatgataa ttactgggtg  78540
atgtgatggt agaggtactc taaattggag aataaaggaa aacctcaaaa gctttggaaa  78600
gttcatagca tcgtagaggg taaaatatat gaagcttgtt tataaactat aaatcagagc  78660
attagagaat gaagtgatta tatgttagta aaatcagctg tgtccttgtg ttatgtgtta  78720
aaattaataa gagtgtgcac aggaaataga aaatggagaa ttggaaacaa caagggaagt  78780
aagatagtcg ttcatttcat ttttcaaagt taaggctaag ccgaagggtc ggaacatgtt  78840
gtatggaaga taggaacagc atgattttaa gagaagaata catgaacaag tgaaataaca  78900
gtggccgttt attgtctgct taccatgtag ttagcactgt tctaactgct tttcattaaa  78960
ttctcagaac aagtattaaa tgttagacat tattttcccct cttttacaaa agggggaagc  79020
tgagaggtta aggaaacaaa gaggttaagt tgcttaccca aggacacata gttactagtg  79080
ttggagccag tttgaactca tggatccagt tccagaatgc ttttgtgta ctagatattt  79140
attaatgtat tagatgattg tttgccttaa tgtaattgac tatataggta attttgctt  79200
gtaatttaaa ttagttcgaa tacataacgt gttttcattt tcccagcgta tttcaacttg  79260
gcttatctgc tcagtgttct tgggggagtt actagggaaa aaaatataac agtatttgtc  79320
ctcagagttt gcagtttgtt ctggcaacac gagaccacac ataaacggca taagtacagt  79380
aacaggaact tataaacaag agcaaattaa tgaattacaa agtagagaca tgtcttaaaa  79440
tgtgccatag ggaatctttc cataactttt tttttttttt aacttctgcc ctttatcttt  79500
catagtgttc tttggtttct ttggggtttt taaagataag aagtacatag gccaggtgca  79560
gtggctcacg tctgtaatcc tagcactttg tgaggcagag gcgggtagat cacgaggtca  79620
```

```
ggagttcatc agccttgcca agatggtgaa accccatctc tactaaaatt ccaaaaatta   79680
gctgggtgtg gtggcaggtg cctgtagtcc cagctattca ggaggctgag gcaggagaat   79740
tgcttgaacc tgggaggcgg aggttgcagt aagccaagat tgcaccattg cactccagtc   79800
tgggcaacag agcgagactt catctcaaaa aagaagtgg ggggtgggg gaatacatag      79860 acattggtag aaataacaa aacaaaatt aaatttaca aattgcttgt atttactgat       79920
ttgcatgatt ttcacctaaa ctgcagaaaa ttgtccatag gagtttttac tagtagtatt   79980
ttatctttac cactgatcta atggtagaaa aagaaataga gctctaagag aggttttttt   80040
ttcttctttt taaaagttat cacttgtctt ttgtttacat agaaaagtgt ggctttggaa   80100
taaattatat tacttgaccc acctcccaca aaagttttgc ttaaactcgg cctataggct   80160
ggaaggacta ggatgaaaag gggtattgct aatggatact ggtttctttt tgagtgatga   80220
aaatattcta acatttattg tcataagagg tgcagaactc tatactaaaa aacatttaac   80280
tgtgtgcttt aaatgggtga attttatggc acgtgtatat tatctcaata aagctgttta   80340
aaaaatcacc tggtgacgtg aatccattgg tcaaaaataa aataaagaga aaaaaaaaac   80400
caaaaaatac ctgacctaca gtgagcaaac agtgtcacct ataataaatt taaaactttt   80460
ttattgtggt aaatatatat aacaaaatta atcatttttc ggtacaattc agtggcatta   80520
catacatcca gtgctgtgca accatcacca ctatccattt atagaacctt ttcatcatct   80580
cagaaaataa ttttaatat tctagttcaa gtttggaagc agtagtcttg acctactgca   80640
tttcaaaatc taggctctag aaatacttgc tccaccaaaa ttgagttgtg tctccacagt   80700
ttttagcctt tttgctggtt tccctcaaa ccaacttttt cttttgtgtt tcctatctca    80760
ggtaatggca tcactattca tgaagttgtc caaacaagaa atacctatca tcgtttctct   80820
cctttatccc ctgtatttag tcaccagtgc ctatggatca tgcttcctta atatctttga   80880
acctgtctac ttctccatat ctcattgtta tttacttgac ttagattcct gtccactttc   80940
acctggtttt aatagccagc cagtcataat agtagaggaa tcagtcaagc aaaaatgctt   81000
tggaagaatt aaataagcaa tgctgaacat caggaattgt agatatccgt acagagagtt   81060
ccagtaaaat tttatgagtc cacgacccct tttctaagca gtctggtcca tgttggtctc   81120
atacctcata tgcaggattc attcattcat taaatatttg tttcatacct tgtttgtaac   81180
acttctgtct gccttctaaa tgtatcctca gtccactttc taccacttgc tactgtgttc   81240
atccaagtca ccatcttccc tcctgtggtg tctctgcttc cctctttgca tctattctaa   81300
atatagatag ctctcagtgt gatcctgatg ggagatcata tctatcttct gtttaagaac   81360
cctccccaaa ggccttctca tcccgcctaa agtcagtgaa gacctgtggg cccttgggat   81420
ctatctgtct gttgacttcc tctatcccac tcttcccctc actcgctgtt ccatatttct   81480
tgcatatgct gggtgtgctt tttgctccgg gtcttggcag tttatagaaa tagcacttgg   81540
ggctgggtgt ggtggctcac agctgtaatc ctagcacttt ggaaggccga ggcgggcaga   81600
tcacctaaga ttgggagttc gagaccagcc tgaccaacat ggagaaaccc tgtctctact   81660
gaaaatacaa gattagccag gtgtggtggc gcatgcctgt aatcccagct actcgggagg   81720
ctgaggcagg agaatcgctt gaacccggga ggcgagggt tgcagtgagc caagatggcg    81780
ccattgcact ccgcctgggc aacaagagcg aaactccatc tcaaaaaaaa aagaaatag    81840 cacttggctg catcaggtct ttcctgaaac acttctttag tgagtattaa ttttgtttgt   81900
tgtccatctc ccacactgga atgtaagctg cataaaggca ggagttttgt ctgtttcatt   81960
```

| | | | | | |
|---|---|---|---|---|---|
| tgctgcagaa | tgtccagggt | ctagagcaat | atctggtgca | tcatgagtgc | tcagcatatg | 82020 |
| tttttttaat | gacatctgct | tccctagtgc | acaatatgtt | ctccccttt | tgtgtagtct | 82080 |
| tcttttgcc | tttggtgaaa | tcaatttttt | tttattttgc | ctttggtgaa | atcaatttct | 82140 |
| atttcttcta | tgtttagcat | atgtgtgtgt | gtgtgtgtac | tgaaatatgt | gaaatgttta | 82200 |
| ttatttaatt | ttatatacca | gatttctgtg | ttaaaaattt | tttatatcat | aaagttagac | 82260 |
| tgccctgagg | cttcagaaat | gttagtagcc | tcctaatttg | acttctttag | tgtttaagtt | 82320 |
| tctttcagaa | atcctgaaac | atatccacaa | ccgctgtatg | tatacagttt | cttttaacac | 82380 |
| ttatttggtg | aatttatcaa | tatgaatttg | tcatgtttct | caaatgagc | acttttaaaa | 82440 |
| aattggtaat | attgaatttg | atgaaaccta | ttatttatat | ggagtaaata | atatgaagtg | 82500 |
| gaacaaattt | acatgttccc | tttgagactt | tttatagata | tgcatttgtg | tgtgtgtgtg | 82560 |
| tgtgtgtgtg | tgtgtgtgtg | tgtgtgtgag | agagagagag | aaagagagag | agacagggtc | 82620 |
| tcattctgtt | gtccaggctg | tagtgcggcg | gcatgctctc | agctcactgc | aacctctacc | 82680 |
| acccaggctc | aagcagtcct | cccacctcag | cctcccaagt | agttgggacc | acaggcgtgc | 82740 |
| gtcaccacac | ctggtaattt | ttgtattttt | tgtaaagacg | gggttttgcc | atgttgccca | 82800 |
| ggctggtctt | gaactcctga | gctcaaggga | tcctcccgcc | tcggcctccc | aagagtgctg | 82860 |
| ggattacagg | catgagccac | tgcgcccagc | ccatatttat | tctaaaagaa | agaagtagag | 82920 |
| gttataacag | gaattcaaaa | ttcagttggc | accagcaaac | cccagagact | taggaatatt | 82980 |
| ttttgttact | tttgctatcg | aatctaaacg | ttcatttgcc | caacctactt | ccccttcct | 83040 |
| gaaagaagta | aaaattactt | ttggaaattt | cctgaataaa | tggagtcagg | aatcccagca | 83100 |
| gttcttactg | ttaaaggacg | tgcttgcaca | cgtaaagaag | ggtctgttta | cctaaggttt | 83160 |
| atttagctct | ggaacatcgt | aagccctggt | acaagtccag | ccttcccgaa | actaactgct | 83220 |
| tgcgtgtaca | ctccctgctc | agcttcgccc | cttttaaaat | gaagtcaaaa | cattctaatt | 83280 |
| tggtaaaggt | gttaggtcct | gagaaattat | tactttgtca | atattaccgt | atttgctttt | 83340 |
| cagaatttca | gattccagtc | atcctagaga | gcatattatt | tctacaaaaa | ctgttttagg | 83400 |
| aggactttgt | tatacattgc | tattatactc | acccagagac | agttactttt | tttttttttt | 83460 |
| ttttttgcaa | cggagtttcg | ctcttgtcac | ccatgctaga | gtgcaatggc | acagtcttgg | 83520 |
| ctcactgcaa | cctctgcctc | ctgggttcaa | gcaattcttc | tgactcagcc | tcccaagtag | 83580 |
| ctggaactcc | aggcgtgcac | caccacgccc | agctaatttt | tgtatttttt | tagtagagac | 83640 |
| agggtttcac | catgttggtc | aagctggtct | caaactccga | accgcaggtg | atctgcccac | 83700 |
| cttggcctcc | caaagtgctg | ggattacagg | cgtgagccac | tgtgcccagc | tgacatttaa | 83760 |
| attttttaat | ctgaaactga | cctttctgt | taacatgaag | catttgttca | tgctttgcta | 83820 |
| ctatggtggt | gtcatttaa | cttttctt | gctgaataat | tttgtactcc | attgtatcct | 83880 |
| cataatttca | attgtagtgt | cccatagccc | tccaaaaaa | gcagtcagaa | tcagatttt | 83940 |
| tatttatt | atttatttat | tttattttt | atttttattt | tttgagacag | agtcttgctc | 84000 |
| tgttgcccag | gctggagtgc | agtggcacta | tctcggctca | ctgcaagctc | cgcctcctgg | 84060 |
| gttcacacca | ttctcctgcc | tcagcctccc | gagtagctgg | gactacaggc | gcctgccacc | 84120 |
| acacccagct | aattttttgt | attttagca | gagatgggct | ttcactgtgt | tagccaggat | 84180 |
| ggtctccatc | tcctgacctc | gtgatccacc | tgcctcggcc | tcccaaagtg | ctgggtttac | 84240 |
| aggtgtgagc | caccgcgccc | agcccagaat | cagattttta | tattaagtta | ctaattttt | 84300 |
| gtgccagccg | tccatcagcc | tccccatctt | ggcagggtat | gcagaagaaa | aacctaatag | 84360 |

```
taaaatatct agggaaaatg tcttcatgag aattaaagca aatgcacaga taaaaaacga   84420
atatttttat taccaggatt ttctattctg tgtattcatt cacgtgagca tttaaagaga   84480
gaaagggaaa gaagggaagg ccagctttca tttcttgcct caggacattt aagtttgaag   84540
tgctgttttc ctaacactta ccccatctta caatacaaat tcccggaata tgcagcacca   84600
aaaatttcag tattttttcca gatttgtctt aaaaccaaag gttaagagga gagttcctga   84660
gcccacacct gtaatattta gatggttctg ttttgttgtt gttgttgttt ttaagtaaaa   84720
ggggtattat taaataatag ttggctgtat ttaaaatcat caatagagag atgagaaatt   84780
taacctcaat tccattttg tttaactttg ggtgattttc caagtatttt aaatttttatt   84840 tttattctta ttgaagtatt gacattcata caatgaagtg tacagatctt agacatacag   84900
ttttcataaa tatactcatc taatcaccac ccagattgca gtataaaaca ttccaggctg   84960
ggtgcagtgg ctcacgcctg taatcccagc actttgggag gccaaggcca gcagatcacc   85020
tgaggttggg agttcaagac cagcctgacc aacatggaga aaccctgtct ctactaaaaa   85080
tacaaaatta gccgggcatg gtggcacttg ccttaatccc agctactcag gaggctgagg   85140
gaggagaatc gtttaaacct gggaggtgga ggttgcggtg gaccgagatt gtgccattgc   85200
actccagcct gggcaacaaa agcaaaactc catcacaaaa aagaagaaga agaagaagag   85260
gaggaggagg aggaggagga ggaggggggag ggggaggagg aggaggagga ggagaaggag   85320
gagaagaaga agaagaagaa gaagaaagtc atggtccctg tgaagaaata actttcaggg   85380
cttatggtag agaacagtca accaggaaga gtaccatctt cctgagaagc atatggaata   85440
gtctagaggt attttttggtc acagactagg ttgctgtggc actgttggca tgcacagccc   85500
agaggccagt gatgctcaat gttgtgcaag gcactaaaca gcctaaacaa tgaagaactg   85560
ttttgcccaa aatgccaaca acaatcttac tgagaaactc tggaaatggt tgactgaaat   85620
tttgcagggt gccctctttg gaagatgcag gatggcagaa atcctagatt aaaatgggaa   85680
aggagaatgc aggatggaag gaaatctgtg ggcaccacct ctttccctgg gattctgcat   85740
gatgtagtag actgaaggag aagcagtgtg atgtggcgga ggcggtgtta gggaagaatt   85800
cacagtaggt agatgagtct caacagggtg ggccaacgtg cattgttgat tatttgtaat   85860
gcaacaaagt tactcactta ttcctcttct aaattcctac gttaaatact taacattccc   85920
ttttagtcaa tcctagcaat acaggagcta gaatacatca ttgagtcatt caaagtccag   85980
tctttgaaac cagaagaacc agggagtcaa gtcttggttt ctctatttta agatatgtaa   86040
cctcactggg catcagttta gtttcttagc tgtaacataa ctcttaaata tgccttgctt   86100
ctaaaaggga gaggtgggaa agcctactaa gtctgttctt cctctcagaa gttacttata   86160
tggtgtattg aaagatcttg tggtttaggc ctggtggatc acttgaggtc aggagtttga   86220
gacgagcctg gccaacgtgg tgaaaccctg tctctactaa aaatacaaaa attagctaag   86280
tctggtggcg ggcacctgta atcccagcta ctcaggaggc tgaggcacga gaatcgcttg   86340
aacctaggag gtggaggttg tagtgagctg agatcgtgcc gctgcactcc agcctgggca   86400
acagagcaag actccatctc aaaataaata aataaatatt tttttttttt aaaaagatc   86460 ctgtggttta aatgttgagc atgatggaaa tttgaaatgt ttttaaccca ggtttgctta   86520 tcttttttttg aaagcattac ctgatttcat ctgagatttt ctactatgca cactatttgg   86580
agttcttgga aatgatgtaa taacaatagt cactcctatc tcctcctcca cataagtcca   86640
agataccttc agctgagatg agattaagct gttgttctaa catgtggagt tagctgtagc   86700
```

```
accataaatg caagagaatt cttaatttaa attaatataa atcaacatat tctttcattt    86760
gtttatgata gactataaag tactgtctta tcaggagata aggcaggcta gcagttgact    86820
tggtaatatt tagagatgta gtaaccaaag caaaatgtaa tattcccctg cttagaaatt    86880
gctttactgg gccaggcagg tggatcacat tagcccagga gtttgagacc agcctggcca    86940
acatggtgaa gtcccatctc tactgaaaat acaaaaatga gccaggcatg gtggcgcaca    87000
tctgtaatcc cagctacttg ggaggctgag gcacgagaat ctcttgaatc caggaggtgg    87060
aggttgcagt aggccaagat tgcaccactg cactccagcc tgggcgacag aatgactctg    87120
tctcaaaaaa aaaaaaaaa aaaaagaaa gaaagaaatt gctttcctag aaaaagtgaa    87180
aaaaagcaaa cattaattgg gcctagcact gtgctatttt ctttactcac tttgcttaaa    87240
gggagtcagt actgagagct tccataatta ctttggtaat agcctttgaa aacgtagttt    87300
gctttgactt atctgatgtt ataaacactt gtgtaagagg tctttaagat ataagttcca    87360 gtttttagatt tcaatagaga cacacaacgc aggcaaagta aacatcaagg gtatgtaagt    87420
ttatttctat cagtggagaa catactttgt catgtcctgg tttaaactgt cctagaaaag    87480
gcatatttgt taaaaaaaaa aaaaaaaaaa aaagaagaag ttttcaaaga gaaacttcac    87540
aggaatgaaa tgtgttcttt ctctctctat agtataatcc aaccaaagta aaatatgaga    87600
aaaggtgtac ttccaaataa taaaaataag gctgggcaca gtgactcacg cctgtaatcc    87660
cagcattttg ggaggctgag gtgggtggat cacttgaggt cagacgttca agaccagcct    87720
ggccaacatg gtgaaaccct gtctctacta aaaatacaaa aaattaacc aggcatggtg    87780 gcgggcgcct gtaagctcag ctactcagaa ggctgaggca ggagaatctc ttgaacctgg    87840
gaggcagagg ttgcaacgag ccaagattgc accattgcat accagcctgg gcgacaagag    87900
tgagactctg tctcaaaaaa caaacaaaaa ataacaaaaa taagaccttt gaaacagatg    87960
attaaagtaa aagattgaca gttagcttca attcttataa aaaattgtta aatgaaagag    88020
atatgaaata accacaattt gctattatag tatatattag agctagatga tgggtagtat    88080
ttttccatat tttatcctgc tttatgtcaa ttaattccta gttaatgctg aaaactaact    88140
gaaaccattc ttggagctat ctatttgagg gaccctgagc tgatatagaa aactttacc    88200 tgctttgaga atataacctt taagaagaaa aggggggct gggcgcagtg cctcatgcct    88260
gtaatcccag cactttggga ggccgaggcg ggcagatccc ctgaggtcag gagttcgaga    88320
ccagcctgat caacatggag aaaccccgtc tctactaaaa atacgaaatt agccaggcat    88380
ggtggcacat gcctgtaatc ccagctactc gggaggctga gtcaggagaa ttgcctgaac    88440
ccgggaggcg gaggttgcta tgagccgaga tcgcgccatt gcactcctgc ctgggcaaca    88500
agagtgaaac tccatctcaa aaaaaaaga agaggaaaag aggggtgggg aagttcttca    88560
atttcaaatt ctttcagtgc actgtaatta attggaaagt ataagttgga ggagtagcag    88620
taattttatt ttattttccc caggaagaca gattatatat cagcatattc aggaaatcta    88680
agaagattag gagctgtgta atgaagtata atatgagtta ggagatcaac tctggctgaa    88740
catccttaat atttgtgtcc tttattttga aagatttcag ttaacaacag aaatgttatt    88800
tttgaagctg caggctcaaa catgtttttg ttggttatgg tataagttgt ataaaagctc    88860
atcagctaaa ctggaaatca tattactact gaagcagctg agtgcatgct ctattctttg    88920
aagtataatg ctaaatagta ctagtttaag acaaaaatgt ctgctgcctt tatattcctt    88980
actttattac atggatcttt tcctggcttt caaaaaaaca aaaaaaaaag cagtcttgag    89040
cgttcagaaa attttatagaa cactgtctgt tctaagtcac acctatctag gagggcttat    89100
```

```
ggagtttatt tcagtaataa tatagtagtt ccttctaacc ttaagattac atgcatggct   89160
gagaatcttg agaaatttgg attaagactt gataaaatat tccttttaaa aatgactgaa   89220
aagcaattgg tacaccttaa atctgtttgg cagtgattaa tgtagttccc taaatctaat   89280
tctgttttgt aaacgtgatt gaaggttatc aatatctagt ggttatcagt aggtagataa   89340
ttgtggcgct ccttcaacct ctaccctcca tccttttcaa ggccttctag ttccttaaga   89400
gaactaaatc taggcctggt gcgatggatc agttgagggt caggagtttt agaccagcct   89460
ggccaacaaa gtgaagccct gtctctacta aaaatacaaa aaattagcca ggcatggtgg   89520
cacttgcctg taatcccagc tactcaggaa gctgaggcag gagaatcgct tgagcctgag   89580
aggcagagat tgcagtgagc tgagatcgca ccactgcact gcagcctggg caacagagtg   89640
acactccatc tcaattaaaa aaaaaaaaaa agaggccggg cgcagtggct cacgcctgta   89700
atcccagcac tttgggaggc cgaggcaggt ggatcatgag gtcaggagat cgacatcatc   89760
ctgcctaaca tggtgaaacc ccatctctac taaaaataca aaaaattagc cgggtgttgt   89820
ggcgggttgc tgcagtccca gctactcggg agtctgaggc aggagaatgg cgtgaaccca   89880
ggaggcggag cttgcagtga gccaggagca cgccactgca ctccagcctg ggcaacagag   89940
tgagactctg tctcaaaaaa aaaaaagaa ctaaataatc taatgatgct gttacagcat   90000
attgatcttt tatatctatt ccttccttcc tgagaataag attattgta aagaggttga   90060 agactaaaaa tgacctgtta aagttatcta cattttccaa gaaattaact acatatttac   90120
ttttctctgt ctcttccatg ccaagctgta gatttttta cagtagagtt cctaaaaata   90180
gttttattct aacaaaccat attgaagtcc aaaaggacag ccacacagtt aagtttattt   90240
gtaaaattca agagtcagta cagatttttc tcctccaaat tgcttttatg cttttatca   90300 cccttaaaag taaagattta tgtttgaaaa gtaggaaaga attctgacct ctttatattt   90360
ccatctgtgt tctttcggag ccaaagataa aaacttctta agagcagtat ttttttaaac   90420
agtgctaaac tttcttcttt gtttcaagtc tgtattagac cagatacttg ctgaaactct   90480
gcagtgaaaa atccttggga ctgagctact acactggcgt taaatagcaa ttggtcttct   90540
tgcataaata ttaactgcta ttttatatga tactcaagtc aaagtgggta actatgttgt   90600
ctgttaagat tcagtttcac tttaagagca aaggataact attttctaac gtgtaaatgc   90660
cagggcttac tgatttgtct acatttattt tactgctttt attttcctgt tattctcttt   90720
gaaattagta agttaaacca taagaaattt cctgctttaa ggtcaaaaat ggtagcatgt   90780
tggcagtttg atggttcagc ctagcaattt taaaggataa caggccactt tattttata   90840 tatttattta tttatttgag atggagtctc tgtcacccag gctggagtgc aatggcataa   90900
tctcggctca ctgcaagctc cgcctcctgg gttcatgcca ttctctcgcc tcagcctccc   90960
aggtagctgg gactacaggc gcccaccacc acgcccggct aattttgttt ttgcattttt   91020
agtagagacg gggtttcacc gtgttagcca ggatggtctc gatctcctga ccttgtgatc   91080
cgcccgcttc agcctcccaa agtgctggga ttacaggcgt gagccaccat gcccagccct   91140 ccttttaaa tttttttaat ttttcttttt tttttcgag acggagtttc actcttattg   91200
cccagggcag agtgcaatgg cgcagtctcg ctcacggcaa cctctacctc ccaggttcaa   91260
gcaattctcc tgcctcagcc tcctgagtag ctgggattac aggcatgcac caccacacct   91320
ggctaatttt gtattttgg tagagatggg atttctccat ttggtcaggc tactctcaaa   91380
ctcccaacct caggtggtcc gcctgtctgg gcctcccaaa gtgctgggat tacaggcgtg   91440
```

-continued

```
agccaccgtg cctggctcat ttttcgtaag tgacagagtc tcacactatg ttacccaggc    91500
tggagtgcag tggctgttta caggtgcagt catagctcac tacagcccca aactcctgac    91560
tcaagagatc ctcctgcctc agccccccaa gtagccagaa tcacaccact gtgcctggct    91620
ttcctttttt taaaaattga tacataatat ttatggggta catatgatat tttgatagat    91680
gcatacggta tcaaatattc tgatcaaatc agagtatttt ggatatgtgt caccgcaaac    91740
attatcattt ctgtgtgttt agaacatttc agctcttcta gctattttga atacacggt     91800 aaactattgt taactgtagt catcctgtgc tatcaaaagc tataatttat tcctcctatc    91860
taactatatg tttgtaccca ttaaccaacc tctcttcaat cccccttccc ctaccattcc    91920
cagcctctgg taaccactgt tctactctct acctccatga gatcaacttt tttagctccc    91980
acatgagtca gaacatgcga tacgtgtctt tccgtgcctg gctcatttca cttaacatca    92040
tgaccttcag tcccatccat cttgtgcaaa tgacagcatt tcattctttt catggctgga    92100
tagtattccg ttgtgtgcat ctgccacatt ttctttatcc attcatccgc tgatacttag    92160
aatgattccg tatttggctc ttgtgaatag tgctgtagta acatagctg tgcacacatc     92220 cctttgatac actgatttcc tttatttgg ataaacagca gtagtgggat tgctggattg     92280
tatggtagtt ccattttag tttgaaaaaa ctttttttt tttttttaac agaggctagt      92340
taatttgtga ttagatagct aaaaggtttg tgatttttt ttaaaggtgg tggctgggca     92400
gcatggtggc tcactcctgt aatcccatgc acaatcaag gttagaatat tttcatcgtc     92460
cctcctggaa gttcccttct gccccttgc tatcagccgc cttcccatac tttctggcaa     92520
ccatgaatct gttttctgtc attacagtat gtcttttag agtttcatac aaacgaattc     92580
atacagtgtg cagtctcatg tctggcttat ttcaatgaac attatatttt gagattcatc    92640
agcattgttg ccttagcaat catttgttcc ttttcatata tttcctttct ctcctcatgt    92700
ttcttctacc tttttgaaca tatagatcat atttataatg gccttaaaca tccatatctg    92760
ctaatactcc gttatttttg gtcggttttt attgactgac ttttcccctg gttgtacgtc    92820
atattttcct gttctttga atgcctggaa ttttaaaatt atatgttgga cattaattt      92880 acattgctag tttctatatc ttgttgtttt cctttaggta atgttggact ttgttcttgg    92940
aatcagtagg atcctttcaa agcttgcttt taaggttagg gtgggttcag accaattttt    93000
agtctagggt tcatttatct ccactactaa ggtgatagga gtagagtccc cttctgagga    93060
ctctgttaga taacccacat attataagat ctttatattt tggtggacaa aaatacaaac    93120
tattcccagc tccatgtgag tgcaggaatt gtttggccta ttgctttctg atggatcttt    93180
tccccagcct ctgctagttt cttttcatgc gtatagaaat cagtaccctt cccaaagttc    93240
aaagggaccc ttcagcagat ctctaaagct ctctcatcgc accccacctc cctgctcctg    93300
tacactgccc aacaaattct agcccccgca gcctccccag ctctgatctc aactgaccac    93360
tctccactcc aatctcagat gtcctcagct ggcaagactg ggccctcctt ccctgtgcag    93420
cagcctgcaa cctgccttca ggcagcacag tctggcattc cccgtggttc aatgtctaaa    93480
agtcattgtt tatgtacttt gtccagtttc ctattgttta cagcaggaag ataaatccag    93540
cctctagtac tccatggcca gaagaagtct catcttctaa atgtaaatta agcatgtatt    93600
gatacttcta gggggaagtt aggggacttg gctcatcagt tcccaacata cttaaatata    93660
acacacttta atgtctgctt tcttctttgt aacttaagcg atgacataaa tgatgctctt    93720
cagtgctcac actaggctaa tctaagcttg agtgttttc tgtgatcaac ttgaaattat     93780
ctacataaag agtattaatt ttgacttatt tgtggccaac ttatatagag tagcttccca    93840
```

```
tgaatgatgg atatgttagt attctgattc taaggacatt gttagctatc tgtatgtctg   93900
gttaatttgt cataagaact tatgtcatgt atcatgcttg gacttttaaa aatatgaact   93960
tgctgatttt ataatctata tatgaaaatt actgcagcct tttctattca tgagtattca   94020
tggttgagaa gattctaaaa cagttcttag ccctttccaa gcagatcttt taaatttatt   94080
gctttgctct gtataacaga acagttgttt ggatatcttt tcaaagattg acttaccata   94140
atgtcaaaac ctgcccaaat atttagtcag ttggcaattg cagacagaaa cgtgtgtttt   94200
aatctatttg tgttttaggg aagatgagca aaataggatt aaagatacga ttttatacta   94260
ttacagatat gttactgttg tctggtaaga attttaagga aacaggctag gcgcggtggc   94320
tcatgtctgt aatcccagca ctttgggagg ccaaggtggg tagatcactt gaggttaggt   94380
gttcgagacc agcctggcca acatggcgaa accctgtctc tactaaaaat acaaaagtta   94440
gctgggcgtg gtgatgtgca cccgtaaccc cagctatcag gaagctgaga caggagaatc   94500
gcttgaaccc gggaagcaga gattgcagtg agccaagatc gtgccgttgc actccagcct   94560
gggcgacaga gtgagacacc gtctcaaaaa aaaagaaag aaaaagaaaa aagaattgt   94620 aaggaaacaa caaatgaaa ctcagaagat gaaaatttgg gggtctaaag gcttcatctc   94680
tggtcttatg tgtaaaattt atttgcagca cagttaatta gaatgaatct taaagttaga   94740
agatgtaaat tctagttgca gctatgccac ttgctacttg taatgtgcca cacactattg   94800
tgcaactgta ggcatgtcac taccttggtg agagtctccc cacctataat atgaagataa   94860
tcataaatat cctgcctact gtcaagggat ttgtggagtg ctcagtgagg gggtatggct   94920
gaaattcttt gaggatgcta acgctccatt aaacgttttt tacattatta taacttctgc   94980
tgttaacagg tagaatgaca gaatacaaaa tgagacattt tacatttata ttccatatgg   95040
tttactctgt aaaatatttt atggtgaaat ggaaaaaaac gaaacagaac tgattagata   95100
gaatggagat agaggagatt tactgtcttt ttttccattcc tttttactta ggattatttt   95160
gttttctctc accgtgactt tccaggtaaa gagtgtgtac aacagttagc tgaaaacacc   95220
aggtatttca ggagacgcct gaaagagatg ggcttcatca tctatggaaa tgaagactct   95280
ccagtagtgc ctttgatgct ctacatgcct gccaaaattg ggtacgtttt gttgcagatc   95340
acagaccagt ctgtccttat ccttatctgt gatgtgagac cagggcttat gtattttgtt   95400
agggaaaatg gtcttgtcct tactgtgtta accttcattt ggtacatatg ccatagatca   95460
aatagtggat tccaaattgt aaagtatgtt aatttgttct tctttcatta aacatttgag   95520
tttcatgtac tctctagggg cctgggatag atcagtgaat aaaatacaaa catctctgtc   95580
cttgtggagc ttacagtcta gtaggggca acagtcagac agacataata aacaaatgaa   95640
ctgtgtacga tgttagaagg tgtcaagtgc tatggaaaaa aatagagcag gacctatatg   95700
gggagttgag agtgccctgt gggcgggccg ataacactat taaatagggt ggtcagggta   95760
aggaagcctc cttgggaagg aaaatgacat ctgagcaaag atttgaagga gctgacagcc   95820
actggagaaa gaagcatctg tgcaaaggcc acagtacaga agcgagcttg cttagctgac   95880
ggaagagtag caaagaggtc cctggaattg gagcaccgtg ccccagggcg agcagtgggc   95940
catgaggtca gagaggtttt atcagagtgt gttattggat acttaccagg tgtgcagatt   96000
acaccagctt ctttggtttg tatgaggcat acataatgga aagccctgcc ctaggatagc   96060
tttcaatgta tttgagaagt ccagatgtat aatgaaacca gaagcatttt gaaaagcaaa   96120
tgaacagtaa ttatactgaa caaatttat tatatgcaaa gtggccctga agatgtagaa   96180
```

```
taaaggagtg acctgcttag tataggctca gtaagaaagg cacatcttgt tggatgggtg    96240
agttttgagc tggatcttaa agcatttctc cagtttgatt gaactcattg aaggagcaat    96300
ttttgtaaat ttttgaatcc ccagtgtcca ccacagtctc cgacactcag taaatgttta    96360
ctgaaatgaa tatgggagag gaaattaaat cagggaacct ggaagtaatg tgattcaaag    96420
agaatgaaag ggaagtaagg aaaaggtgct ccctgagaga aaagaagaa tttgggtttc      96480 aacatgaagt catatgggca gttggtatta tggcttcaga ggggatgggg aaggattttc    96540
ttcattcttc tttaagtgga attctcataa acaaacatga agagttatca gatccaaagg    96600
actcagtcta gagctctctt taaagaaggc tgtgtctcct ttattctaca taggtgcaac    96660
tgactgtgta cactttaatt aggaaagatt tagagaaggt acaggaccca aagggcaca     96720 aaaaagcaat aactactaaa tataaggaaa acaactctgt atacagcatg tataaagaaa    96780
agcaaggtat atttggggag ataaaagttg taaaggcatt aagatgtgtg tttgttgaga    96840
aaaaataaat ttgtgcattt aagaagttaa aaaaaaaga tttagagaag gtaaagaatt     96900
agaataaggc actagacagt ttgggagcat gtgctgaaga tacagggcac ccaggttcat    96960
gctgacacaa aggaggtatg ttgaggaaga tgtactggta ctacagagag tgggaaaagg    97020
ctgtgaaaag actggcatta atgtaatgcc aaatgtgcag gatctgtata gcccaggctg    97080
gagtgcaatg gcgtgatctc ggcttactgc aacctccacc tcccaggttc aagcaaatct    97140
tgtgcttccg cctccccagt agctgggatt acagatgtgt gccaccacac ctggctaatt    97200
tttgtatttt ttagtggaga tggggtctaa ccatgttggc caggctggtc tccaactcct    97260
gacctcaggt gatctgcccg cctcggcctc ccaaagtgct gggattacag gcacgagcca    97320
ctggcccggc cacattttt tattctcaaa caaatgctgt aaacagctta aggaaaagt      97380 tgaaacataa gggaggtcaa taagaggaaa agacaaaaag caacataatt tgggccaggc    97440
acagtggctc acacctgtaa tcccactttg ggaggccgag gtgggtggat cacaaggtca    97500
ggagatcgag accatcctgg ccaacatggt gaaaccccgt ctctactaaa aatacgaaaa    97560
tcatctgggt gtggtggtgc acacctgtaa tcccagctgc tcgggaggct gaggcaggag    97620
aattgctaga atctgggagg tggaggttat ggtgagccaa gatcgtgcca ctgcactgca    97680
gcctggcgac aaagcgagag actcaaaaaa aaacccacat aatttagtag acaaaattaa    97740
ctaaaagtta gaatgtgtta tttagacaag atacagatgt ggagtaaggc cacagggcct    97800
ccaatttggc ttacgatagg ggtgggggat tgttaaatac gaattgtgtg gtctgagtaa    97860
tcagctgaag ccagcgggtg aactggcctg acagacacca aaggaagccc tgaattctga    97920
agcagtgttg ttcccaagac aattaaagaa acgtgtgatc tggagagctc atgccagtca    97980
gccattctgc tagcagaaaa gatgtgccgt gttacagcag atcccccaca gctgcagaat    98040
cctcagaatt tgcggattaa tgttaaactg ccaagcttaa catttcaagg accagatttt    98100
aattaaatac aggttcattt tgaagcctct gaaccactat tacatatcag gacactttt     98160 ttttttttt gagacagagc cttgctctgt tgctcaggct ggagtacagt cgtgtgatct     98220
tgccttacta cagcttctgc ctccaagctt cgagagattc tcatgcctca gcctcctgag    98280
tagctgggac tacaggtgca tgccaccaca catagctaat tttttgtatt tttggtagag    98340
acgggatttc accatgttgc ccaggctggt tatttcagtt ttgtgaagga caccatatag    98400
gagaagactg ctttaggatt gactttaaaa gtatttgtga gctgtcaatt ttaactttaa    98460
aaggagttaa aggaaactcc tattagaagt ctccaatgcc tgcatcacca aagagttgaa    98520
atctttgagg acagcaggtc ctctgtaatg agtgcttttt cactcctcct ggtttctgtt    98580
```

```
cttgttttcc cctttgcagc gcctttggac gggagatgct gaagcggaac atcggtgtcg   98640
ttgtggttgg atttcctgcc accccaatta ttgagtccag agccaggttt tgcctgtcag   98700
cagctcatac caaagaaata cttgatactg taagtaggca ctttcacctt gatataaata   98760 tgcctttat taaaagggcc tgtatattag atgaaattca taatatattg atcttgatgt   98820
tcttgtgagc acctaagaca gaggggtga cagtgctacc aaaaacattg gcatttacaa   98880
aaaaactgtc acccaccaca cctgcatcat gagagctctg gagaattttc cggctttgtc   98940
ttgctctact gtctccctca ctatggactc tacaattctc tttccactct agctatttct   99000
acattaagct ttctcatatg ttgttctgtc taaaattttc tctcttgagc tttctctccc   99060
ctctgcctgg ctgactgcca ctcattcttc acatctccat ttaaaggaaa attgctcagg   99120
ggcgccccac accttcttgc tctgtgttcc cttggaatcc tgagattctc ccttactaaa   99180
ttcttcacac ctataattat ttaatagcag tcttctccat tagataaata ttgaggatag   99240
gaataagtct gttttactga ttctatatcc cagcacccac cacactgcca ggcatctagt   99300
tggggatcat tattactaag cttaattatt tattatctca agatattctc atctctatat   99360
attctcttaa tatgttattg ttgcaagtct aagatttcag agtttaaatc attattgcca   99420
tctgggagtt tataaagctt tagaacatga catttgcata aaattagttg ctagaaatat   99480
ccattaatga gttagagagc tactaatttt tttttctttt tttgagagag agttttgccc   99540
tgttgcccca ggctggagtg caatggcgtg atctcagctc accacatcct ctgcctcctg   99600
ggttcaagca attctgcctc agcccctga gtagctggga ttacaggcat gcgccaccat   99660
gcccagctag ttttgtattt ttagtagagt cagggtttct ccatgttggt caggctggtc   99720
tcgaactccc gacctcaggt gatccgcctg cctcagcctc ccaaagtgct gggattgcag   99780
gcgtgagcca ctgcctggca agagctacta atcctaaaga acattatgaa tgcttcttta  99840
taaaagttaa ttataacaat ttgatggaca ttttgtattc ctgaatagcc gaagacttga  99900
cttttcttct ctgtttctac acagcaaaat ttctatgagt ataagtgtat tcccttttaa  99960
aaaacaaaat tgtagtaaga acacttaaca tgagatctgt cctcttaaca aattttttcca  100020 tgtcgaatac agtattgtta actataggca cagtgttgtg agcatattct taattacatt  100080
ctgacaatat ccaattagat tcaactttttt gatattgtat cttttttttc tttattttga  100140
ttatgcctgt cagatttttc caatggattt ttctcatttc tcagaaattt tactggtgaa  100200
tttctgtgat gattttttttt aacctagaga tttcagcttt tctttccttc ctactctatt  100260
gatgttttaa gaattttctt ttttctttct catgttcacc tgttaactca gaatttcaat  100320 gtgccttttaa aaaaagtct gtgtaactat aaccagtgtc tatggcagta atccatgcct  100380
tctgaccaca actttgactt ctgagaactg tacacattca tgaaagaatt tagatgtaac  100440
caggatatct ccttaggata tctaaggaga tttctgttgc caacaagtat gtttgccaac  100500
tgagagttct aatccttttc ataagattct cttgagggat tgttgggctt tgcctcccat  100560
ttagtttttt aaagcataaa gtgcattttt tgaaaccatg gatttgttaa agtcatttttg  100620 tcttatgatg ttttatggaa ctaaacgtgt actagaccat tatgagatac aaattaatttt  100680 tcatttaata atgggcctca tgacatgatt ctgtatatag aaagtgctgt aaaatacaca  100740
cacacacatg cgcgcgcgcg cacacacaca cacacacagc tagagctcat aaatgaattc  100800
atcaaagttg cagggtaaaa gatcagcaca caaaaaaatta gtgcttttat acaccagcaa  100860
tgaacaaatg aaaagaaaat ttcttttaca attttcaaaa gaagaaaata cctagtaata  100920
```

```
aacttaagaa agcctttcct ggctgggtgc ggtggctcac acctgtaatc ccagcacttt    100980
gggaggtcag gcgtttgaga tcagccttgc caacacagtg aaacctcatc tctactgaaa    101040
atacaaaaaa ttagccaggc atggtggggg gcacctgtaa tcccagctac tcgggagact    101100
gaggcggaag aaccacttga atctgggagg cggaggttgc agtgagctga atcgcacca    101160 ctgcactcca gcccgggcga cagtgcgaga ctctgtctca aaaaaaaaa aaaaaaaaa    101220 aaaagccttt cccttgtaca ctggctaatt tacacttgta cactgtattt ttagatgtgt    101280
atattgaaaa ctataaaact ttgctgaaag aaattacaga agacttaaag aaatggaatg    101340
acatcctgtg ttcatggatt ggaagattta atattgttaa gatggcagta tagcaaccta    101400
cagatcctgt gttcagcatt tctcagaaaa aaatggactg ggagaccta agccactggc    101460 cctttttgc agaaattaaa aggctgatcc tcaaatgtat atggaactgg cagggaatag    101520
ctaaaatagt actgaaaagg aaaagcaaag tgggaggact cacacttctt aattttaaaa    101580
caaagctaat tactacaaag ctacagtaat tacaacagtc gagtactagc ataaggatag    101640
acgtatagac cagtgaagta gaattcagag ttcagaaata aagcacaagc atctatggcc    101700
aatttgtttt caacaaggga gccaagacca gtcaatgaga aaagaatagt ctcttcaaca    101760
aacagtacta ggtcagctgg atgcagaaga gtgaagtttt aaccctacag catggataaa    101820
ccttgaaaac attaggctaa atgaaagaag ccaaaacaaa gactacataa cttacaattc    101880
catttataag agatgtccag aacaggcaaa tcatagggtc agaaaataga ttggtggcag    101940
ccagcctgag aggaggggga gtgaggattg agacaacgag tattgggttg cttttaggg     102000 tgataaaaat actctaaaac tagatagtga caaaagttgc acaactctgt gaatatactt    102060
agaagcaatg aattgtatac tttaaaagtg aattttgctg aatgtgaatt gtatctcaaa    102120
gctataattt tgttattttt taaaatggga agcgcaagga tattggctca ggggagcggc    102180
aggatggctg tcctagagga ttcggttact cagctctata atgaatacat gttttctcc     102240 tagaaaccca ccttacctgt gatctagagg ttctgtgtag actgttaatg aatggcgatg    102300
catgtaatgg ctgcctgtcc ctaacatacc caaataccc acacaagagt cagcactcat     102360
tagaatgtca tcttatattc acatgacacc gatttgtctg aaatatttgg agtgggatca    102420
aaggaaatct tgtaatctag atccccttgg gctactgagg atttcttttt ctatctaatg    102480
attacttttc tacattgatg aaaaaattct agattcttct aaagtttata aatgtccatt    102540
actttgtgat cttagtcatg tgcacttttg tcttattatt attattttga ggcagggtct    102600
cagtcaccca ggctggagta cagtggcatg atcttggctc actgcagcct ccatctccca    102660
gcctcaaggg atcgtcccac ctcagcctcc agcatagctg ggactatgcc tgccaatttt    102720
tttttctttt aagagacgag gtcttactat gttgcccagg ctggtctcaa actcctgggt    102780
tcaagcagtc cgcctgcctt ggcctcccaa agtgctgtga ttacaggctt gagccaccgt    102840
gttcagcctt gactttttt tttttttttt tgagacagag ttttgctctt gttgcccagg     102900
ctggagggca atggcatgaa ctcaactcac cgcagcctcc gcccctggg ttcaagcgat      102960 tctcctgcct cagcctcccg agtagctggg attacaggca tgtgccacca cgcccagcta    103020
attttgtatt ttcagtagag acagggtttc tccatgttgg tcaggctgat ctcaaactcc    103080
cgacctcagg tgatctgccc atctcagcct cccaaagtgc tggaattata cagacatgag    103140
ccaccgcgcc cggccagctt tgactttgt cttaaattat tacatcttgt cacagaggtc     103200
aggtgaataa atggtcgatg ggttctccca gcttaatttc agacttaaat tgtttccatg    103260
tggagctttc acttatacct cttctcagag gtaccgctgt tgtgatagca cattgacgtt    103320
```

```
cagctcttat ttgctttat attttcaca ttttgaaatg aagaatattt tttcttgtgc   103380
tacaatacat cagtaatact ggtggttttc tctctccaaa cactgatttt ttaaaaaaat  103440
gaagtttaag atgccaggtg tggtggctca tgcctgtaat cctaacactt tgggaggcag  103500
aggtgggtgg gtaacttggt gccaggagtt caagactagc ctggccaaca tggcaaaacc  103560
ctgtctggac aaaaattagc tgggtgtgat ggcacatgcc tgtagtccca gctactcaag  103620
aggctgaggc agagaatctc ttgaacccag gaggcagagg ctgcagtgag ccgagatggt  103680
gccactgtac tccagcctgg gtaataaagc aagactctgt ctcaaaaaaa aaaaaaaaa   103740
aaaaaaaaa gttgctgggt tcgttggctt acgcctataa tcccaacact tgggaggcc   103800
aaggtggtgg atcacttgag gttgggagtt caagaccagc ctggccaaca tggtgaaacc  103860
ccatctctac taaaaataca aaaattagct gagcatgatg gcgggcacct gtaatcccag  103920
ctacttggga ggctgtggca ggagaatcac ttgaacctgg gaagtggagg ttgcagtgag  103980
ctcggagggc gccacagcac tccagcctga gcaacagagc gatactccat ctcaaaaaca  104040
aaagggagag atgacaaatt gtattcggtt ttgtaagttc agagtgcata aacttttc     104100
taccaagcat atcatacttt gaattatagc ctttattctg catacctggc tattcacaac  104160
ccattattca tggtgagctt gaaggccttg ttcaaaaagc agctccttcc acagctgtat  104220
tgtagtctga tcttgtaaat gcactagaca taagtcctgc cgaaggataa tcttgccatg  104280
attgttttta gcaaagtaaa acaccaggca tgcctgcatc ctactggctc tgacagacct  104340
ctactttgtc ttgtgtattt taggctttaa aggagataga tgaagttggg gacctattgc  104400
agctgaagta ttcccgtcat cggttggtac ctctactgga caggcccttt gacgagacga  104460
cgtatgaaga aacagaagac tgagcctttt tggtgctccc tcagaggaac tctccctcac  104520
ccaggacagc ctgtggcctt tgtgagccag ttccaggaac cacacttctg tggccatctc  104580
acgtgaaaga cattgcctca gctactgaag gtggccacct ccactctaaa tgacattttg  104640
taaatagtaa aaaactgctt ctaatccttc ctttgctaaa tctcaccttt aaaaacgaag  104700
gtgactcact ttgcttttc agtccattaa aaaaacattt tattttgcaa ccattctact  104760
tgtgaaatca cgctgaccct agcctgtctc tggctaacca cacaggccat tcccctctcc  104820
cagcaccttg cagacttggg cccatcaaga gctactgctg ccctggctc cgcagcctgg   104880
atacttacct ggccctcctc cctagggagc aagtgccttc cacttacttc ccatccaggt  104940
ctcagaggtc tcaaggccaa ccttggaatc cttatttaac cattcaagta atcaacggaa  105000
gttttcaccc tttaatctta agtttagcct tttaagaaaa acagtaagcg atgactgctg  105060
aaaggctcat tgtgtaatct cccaaggggt tggtcttatt ccattttctt ctggtcacca  105120
gatgatttct tcctttacca tcaaatactt cttcataatg gtcacagtct gaggatgtgc  105180
gcaaattctg gttcttccca agctctaacc gtaacacgtc ccaccccctt tttaaagcac  105240
ttactgtttt cagagcaccc atatcccacc ctggtgagaa ggccactctc acatctgagt  105300
gttgggtaca aagctgctcc gtagagtgat gtgcactcct ggtgggtgag gggcagggc   105360
agtggcagtg tgcaaagaat tgattactcc ttgcagagcc tgtggcttgc attcctact   105420
gctttctacg tttgaaaatt atgacagtct ctggctaggt ctgggtccag attaggattt  105480
aaactgataa aggaaactgt tggtaaatcc tctgctcaga aagcatttat catgttccta  105540
tttaaggatt aggtttatta atttaggcct cttagaagct aacccactta aatattactc  105600
ttctgaatgc tagttctctt ttattcttga tgtcctaagt caattgaatc tggcatctgg  105660
```

```
ggctagggtc tgcctgtcta catatttttt attttttttct gagaaattct gaacacatag  105720
atctctttcc taaactgaca ttttctattt tgactgtttt catactataa ccaggtaaag  105780
ggacttcttt cagagagctt tatactgcct gaccaaagaa caaatctgaa aatcaccatt  105840
ttaaagttat ttttcagtt gaaccaaagt ttaagtgaag aggacttttg gcatattata  105900
cccaggatca gtttgtcttt ttgtatccat caagtattac aggagaagga ttgggaacag  105960
aatggaaaaa cagtgtatga aagtcatgtt acaggccgag tgcggtggct cacacctgta  106020
atcctagcac tttgggaggc tgaggcaggt ggctcacttg aggtcaggaa ttcaagacca  106080
gcctggccaa catggtgaaa ccccgtctct actaaaaaga caaaaaatta gctgggcgtg  106140
gtggcgggca cctataatcc cacctacttg gtaggctgag gcaggagaat cgcttgaacc  106200
caggaggcgg aggttgcagt gagacgagat tgtgccactg cactctagcc tgggtgcag  106260 agcaaaactg tgtctcaaaa aaaaaagtca tgttacacat ttaagttttt gaaattgctc  106320
cttttatcgg taaagattct caatccaaat tctcctgggt gtgttgtcat cagctgtgat  106380
atgtttgtgc acattacgta tagcagagga tgtaagcaat attattgttt gtgaagtttt  106440
gtttttaatg tcttgagtat gagttatgtt tagtcactgt cagcatctga aactttaat  106500 aagcccttga gatattccaa agtttatttt tactttttta aagaacagaa aaagatgaat  106560
gaaagaacca aggagagatg cagagactat atttagcatg tataggttaa agtaagaagg  106620
aggttgtggt aactaaatag gagtcctata aaatcaaata cattgtcaac cttttctgca  106680
catctagttt cctaccatag aatcccactg gaataccaca tagcttttgc actgcagtta  106740
ctatttacta atgtaaacgt agggtttgta aagtcacaa acttataagc aatgaactta  106800
cctgctagtc tttttatttt ggcttgcatg aagtcactgc aaattcaaat gtcagtaccg  106860
gcatttaaaa tatatctata tcactttgtt ggtacaaagt tatttcaaga taagtgtaat  106920
tttgttacaa gtttattttg aagagacaaa tctcctgtga tctatgcagg acctctgtac  106980
tttctaaaga acaaaatgtt atgtagacat tatacatggt tggttgtctc ttcttgaaac  107040
tgtaatgtaa atctagggtc cagtcatatc ctaggtatca tcatttatcc aagtacttgg  107100
aggaatacaa gtatatataa atacagtcat tgagaataag tcgatttgag gcatacaaga  107160
gtagtttctt acacagtttta acacggcctg attcaagact ctgataggat tcaaacagat  107220
accggttaac catgactacc aaaactgatc atctgagtcg attgatagag gtgtgactag  107280
tccttagcac ttttctcat tcctcttttt attcagcatt gctgttacct atttcaggtt  107340
tataagacct ctttcagcag atcacatcag aagccaggaa atgcatagct aggagatgtc  107400
aaaagcccat atgaggagtg gaccaagcag cagtggcggt ttctcctcgc atctttttt  107460 ttttaagctt taacttagca ggggcatgga ctttatagca ctttttcaac ttttttgcttt  107520 gctttggata agaaatcctt acctttaaaa aaagcttcta gtctccataa cccccaaagt  107580
actgcttatt tgtttgaaga atccagccat cgtagtgctt tagtcactat cgtaaacatt  107640
catgataggg caaggatttt aaaacaggat tcttgcttct gtagtcatca aggtgaacag  107700
aagcatccta cacaaccact aagggctcta tgtttgtgtc atgcctcttc aaacaccaag  107760
gagttgaaca tgcttccagt gatttgtctc cgtaatgcct tcttcctta tttggcctttt  107820 ctttctttct gtaccttcaa gttcttgatt tttaaaattc caactctaga gaaaccaat  107880 atatggtggt gctgggcttt gaagatagca tatcagacgc cttggttctg tttgtacact  107940
tagccttaca tttcaggagg aggcttttca ttagggcctt aagctagctc ctttggcttt  108000
taaaaaaaat ttttttttcaa atttcttcat tacctaaggg agcctgcatc taaatttctc  108060
```

```
aactagttca gcctagctga attttctagt gtgttataca ctttgcttcc ttcttattgg   108120
tgaaaaccag ggggatgagt ggcttccatg gagagatttc ctgatttctc agggaggaaa   108180
aaagtgatga catttaccac tacttttatg ttttcccct ttttccaaat tgataaggat   108240
ttctggttcc tagtgatccg ggattgggca acagtgcaga actgccagtc atgccgtagg   108300
ccgtgaagaa agaatgtgag taactgttgt tttgcaagga tttgtagggt tatgggcagt   108360
tgttgtttga agcattgcta tgacctaatt cccaaggtat cttcctctc ttggtgttct    108420
aggtaagcca atgagcttta atctctactt gctataaccg tgtgcttaga aaaagaggtg   108480
agagtagtgg ttttccttca aactgtccac attcatgaag attatgaatt gttaggacag   108540
ccagggcaag atagaccctg tctctacaaa aattttttc taaattaacc gggcatggtg    108600
gtgcctgcct gtagtcccac ctgtgtggga aatcacttg agcctgggag gtcaaggctg    108660
cagtgagcca tgattgcacc cctgcactcc agcctgggtg acagagtgag accctggctc   108720
aataagaggg ggaaaaaaaa ttgttaggag ctgggtgcgg atgcagcctg caatcccagc   108780
tacttgagag gctgaggccg gaggattgct taaacccaag aatttgagcg tagcctgggc   108840
aacacagcaa gaccccatct aagaaaaaaa tgttttttaa atcagcttag cccaaagggg   108900
ttgtgaatgg ggaggtataa aaagcaaaga ttattttttg gctactaagc caagaactta   108960
cagggatttt tttttcagt cccagaacct acagataccc tgctacttgc ttcacgtgga    109020
tgctcagtgc ccagcagcca tcttaataca ttaaaccagt ttaaaaaata ccttccatgt   109080
ggagaaaaac atgtcttttt ctcgcctcaa ctttatccac atgaaatatg tgcccatggc   109140
tgggcgcagt ggctcacctg taatcccaac actttgggag gctgaagcag gcagattgct   109200
tgaggccagg agttcgagaa cagtctggcc aacatggcga aacctcatct ctactaaaat   109260
tacaaaaatt agccgggcat ggtggcacat gcctgtaatc ccagctacgt caggaggctg   109320
aggcacagga attgcttgaa cccaagaggc agaggatgca atgagccaag atcacaccac   109380
tgcactccag ccttggcgac agagggagac tctgtctcaa aaaaaaaaa aaaaggtgtg    109440
cccaggcccc tagccattgc catgtgccca gccagagagc caaattgagg gctggcttc    109500
cctatcacac agaataaatg ctagtgctag ccaatgatcc ctttgctttt aatgtataga   109560
aaatactgtt gttcctttg tcatttccag tgacatctgt tttctaagca gctctttct     109620
agggaggaaa ccaaaggggc taggttaaga ccctaataga aatgtttttt ctaatctctg   109680
gtgagtctgg aagtgtcaca ttcacagtcc acccttggga gtggcttggt ggagctgggg   109740
acaaggtttt gttactaca tagtgcacat gataaatggc cttaaactgt gattctttct    109800
ggtaggataa gttataataa actgacccta aagaatgcaa t                        109841
```

<210> SEQ ID NO 2
<211> LENGTH: 7250
<212> TYPE: DNA
<213> ORGANISM: Homo sapiens

<400> SEQUENCE: 2

```
ccttggccga gaccggtcct ctgcggagag ggccccgccc tctgtgaagg cccgcccggg     60
aattggcggc ggcgctgcag ccatttccgg tttcggggag gtgggtgggg tgcggagcgg   120
gacttggagc agccgccgcc gctgccaccg cctacagagc ctgccttgcg cctggtgctg   180
ccaggaagat gcgccggag cccggaggct gctgctgccg ccgcacggtg cgggcgaatg   240
gctgcgtggc gaacggggaa gtacggaacg ggtacgtgag gagcagcgct gcagccgcag   300
```

| | | | |
|---|---|---|---|
| ccgcagccgc | cgccggccag | atccatcatg ttacacaaaa tggaggacta tataaaagac | 360 |
| cgtttaatga | agcttttgaa | gaaacaccaa tgctggttgc tgtgctcacg tatgtggggt | 420 |
| atggcgtact | caccctcttt | ggatatcttc gagatttctt gaggtattgg agaattgaaa | 480 |
| agtgtcacca | tgcaacagaa | agagaagaac aaaaggactt tgtgtcattg tatcaagatt | 540 |
| ttgaaaactt | ttatacaagg | aatctgtaca tgaggataag agacaactgg aatcggccaa | 600 |
| tctgtagtgt | gcctggagcc | agggtggaca tcatggagag acagtctcat gattataact | 660 |
| ggtccttcaa | gtatacaggg | aatataataa agggtgttat aaacatgggt tcctacaact | 720 |
| atcttggatt | tgcacggaat | actgatcat gtcaagaagc agccgccaaa gtccttgagg | 780 |
| agtatggagc | tggagtgtgc | agtactcggc aggaaattgg aaacctggac aagcatgaag | 840 |
| aactagagga | gcttgtagca | aggttcttag gagtagaagc tgctatggcg tatggcatgg | 900 |
| gatttgcaac | gaattcaatg | aacattcctg ctcttgttgg caaaggttgc ctgattctga | 960 |
| gtgatgaact | gaatcatgca | tcactggttc tgggagccag actgtcagga gcaaccatta | 1020 |
| gaatcttcaa | acacaacaat | atgcaaagcc tagagaagct attgaaagat gccattgttt | 1080 |
| atggtcagcc | tcggacacga | aggccctgga agaaaattct catccttgtg aaggaatat | 1140 |
| atagcatgga | gggatctatt | gttcgtcttc ctgaagtgat tgccctcaag aagaaatca | 1200 |
| aggcatactt | gtatctggat | gaggctcaca gcattggcgc cctgggcccc acaggccggg | 1260 |
| gtgtggtgga | gtactttggc | ctggatcccg aggatgtgga tgttatgatg gaacgttca | 1320 |
| caaagagttt | tggtgcttct | ggaggatata ttggaggcaa gaaggagctg atagactacc | 1380 |
| tgcgaacaca | ttctcatagt | gcagtgtatg ccacgtcatt gtcacctcct gtagtggagc | 1440 |
| agatcatcac | ctccatgaag | tgcatcatgg ggcaggatgg caccagccctt ggtaaagagt | 1500 |
| gtgtacaaca | gttagctgaa | aacaccaggt atttcaggag acgcctgaaa gagatgggct | 1560 |
| tcatcatcta | tggaaatgaa | gactctccag tagtgccttt gatgctctac atgcctgcca | 1620 |
| aaattggcgc | ctttggacgg | gagatgctga gccggaacat cggtgtcgtt gtggttggat | 1680 |
| ttcctgccac | cccaattatt | gagtccagag ccaggttttg cctgtcagca gctcatacca | 1740 |
| aagaaatact | tgatactgct | ttaaaggaga tagatgaagt tggggaccta ttgcagctga | 1800 |
| agtattcccg | tcatcggttg | gtacctctac tggacaggcc cttttgacgag acgacgtatg | 1860 |
| aagaaacaga | agactgagcc | ttttggtgc tccctcagag gaactctccc tcacccagga | 1920 |
| cagcctgtgg | cctttgtgag | ccagttccag gaaccacact tctgtggcca tctcacgtga | 1980 |
| aagacattgc | ctcagctact | gaaggtggcc acctccactc taaatgacat tttgtaaata | 2040 |
| gtaaaaaact | gcttctaatc | cttcctttgc taaatctcac ctttaaaaac gaaggtgact | 2100 |
| cactttgctt | tttcagtcca | ttaaaaaaac atttatttt gcaaccattc tacttgtgaa | 2160 |
| atcacgctga | ccctagcctg | tctctggcta accacacagg ccattcccct ctcccagcac | 2220 |
| cttgcagact | tgggcccatc | aagagctact gctggccctg gctccgcagc ctggatactt | 2280 |
| acctggccct | cctccctagg | gagcaagtgc cttccactta cttcccatcc aggtctcaga | 2340 |
| ggtctcaagg | ccaaccttgg | aatccttatt taaccattca agtaatcaac ggaagttttc | 2400 |
| acccttaat | cttaagttta | gccttttaag aaaaacagta agcgatgact gctgaaaggc | 2460 |
| tcattgtgta | atctcccaag | ggtttggtct tattccattt tcttctggtc accagatgat | 2520 |
| ttcttccttt | accatcaaat | acttcttcat aatggtcaca gtctgaggat gtgcgcaaat | 2580 |
| tctggttctt | cccaagctct | aaccgtaaca cgtcccaccc ccttttttaaa gcacttactg | 2640 |
| ttttcagagc | acccatatcc | cacccctggtg agaaggccac tctcacatct gagtgttggg | 2700 |

```
tacaaagctg ctccgtagag tgatgtgcac tcctggtggg tgaggggcag gggcagtggc    2760
agtgtgcaaa gaattgatta ctccttgcag agcctgtggc ttgcatttcc tactgctttc    2820
tacgtttgaa aattatgaca gtctctggct aggtctgggt ccagattagg atttaaactg    2880
ataaaggaaa ctgttggtaa atcctctgct cagaaagcat ttatcatgtt cctatttaag    2940
gattaggttt attaatttag gcctcttaga agctaaccca cttaaatatt actcttctga    3000
atgctagttc tcttttattc ttgatgtcct aagtcaattg aatctggcat ctggggctag    3060
ggtctgcctg tctacatatt ttttattttt ttctgagaaa ttctgaacac atagatctct    3120
ttcctaaact gacattttct attttgactg ttttcatact ataaccaggt aaagggactt    3180
ctttcagaga gctttatact gcctgaccaa agaacaaatc tgaaaatcac cattttaaag    3240 ttatttttc agttgaacca aagtttaagt gaagaggact tttggcatat tatcccagg     3300 atcagtttgt cttttgtat ccatcaagta ttacaggaga aggattggga acagaatgga    3360
aaaacagtgt atgaaagtca tgttacaggc cgagtgcggt ggctcacacc tgtaatccta    3420
gcactttggg aggctgaggc aggtggctca cttgaggtca ggaattcaag accagcctgg    3480
ccaacatggt gaaaccccgt ctctactaaa aagacaaaaa attagctggg cgtggtggcg    3540
ggcacctata atcccaccta cttggtaggc tgaggcagga gaatcgcttg aacccaggag    3600
gcggaggttg cagtgagacg agattgtgcc actgcactct agcctgggtg acagagcaaa    3660
actgtgtctc aaaaaaaaaa gtcatgttac acatttaagt ttttgaaatt gctccttta    3720 tcggtaaaga ttctcaatcc aaattctcct gggtgtgttg tcatcagctg tgatatgttt    3780
gtgcacatta cgtatagcag aggatgtaag caatattatt gtttgtgaag ttttgttttt    3840
aatgtcttga gtatgagtta tgtttagtca ctgtcagcat ctgagaactt taataagccc    3900
ttgagatatt ccaaagttt attttacttt tttaaagaac agaaaagat gaatgaaaga     3960 accaaggaga gatgcagaga ctatatttag catgtatagg ttaaagtaag aaggaggttg    4020
tggtaactaa ataggagtcc tataaaatca aatacattgt caacctttc tgcacatcta    4080 gtttcctacc atagaatccc actggaatac cacatagctt ttgcactgca gttactattt    4140
actaatgtaa acgtagggtt tgtaaaagtc acaaacttat aagcaatgaa cttacctgct    4200
agtcttttta ttttggcttg catgaagtca ctgcaaattc aaatgtcagt accggcattt    4260
aaaatatatc tatatcactt tgttggtaca aagttatttc aagataagtg taattttgtt    4320
acaagtttat tttgaagaga caaatctcct gtgatctatg caggacctct gtactttcta    4380
aagaacaaaa tgttatgtag acattataca tggttggttg tctcttcttg aaactgtaat    4440
gtaaatctag ggtccagtca tatcctaggt atcatcattt atccaagtac ttggaggaat    4500
acaagtatat ataaatacag tcattgagaa taagtcgatt tgaggcatac aagagtagtt    4560
tcttacacag tttaacacgg cctgattcaa gactctgata ggattcaaac agataccggt    4620
taaccatgac taccaaaact gatcatctga gtcgattgat agaggtgtga ctagtcctta    4680
gcactttttc tcattcctct ttttattcag cattgctgtt acctatttca ggtttataag    4740
acctctttca gcagatcaca tcagaagcca ggaaatgcat agctaggaga tgtcaaaagc    4800
ccatatgagg agtggaccaa gcagcagtgg cggtttctcc tcgcatcttt ttttttttaa    4860
gctttaactt agcaggggca tggactttat agcactttt caacttttg ctttgctttg      4920 gataagaaat ccttaccttt aaaaaaagct tctagtctcc ataacccca aagtactgct      4980 tatttgtttg aagaatccag ccatcgtagt gctttagtca ctatcgtaaa cattcatgat    5040
```

```
agggcaagga ttttaaaaca ggattcttgc ttctgtagtc atcaaggtga acagaagcat    5100
cctacacaac cactaagggc tctatgtttg tgtcatgcct cttcaaacac caaggagttg    5160
aacatgcttc cagtgatttg tctccgtaat gccttcttcc tttatttggc ctttctttct    5220
ttctgtacct tcaagttctt gattttaaa attccaactc tagagaaaac caatatatgg    5280
tggtgctggg ctttgaagat agcatatcag acgccttggt tctgtttgta cacttagcct    5340
tacatttcag gaggaggctt ttcattaggg gcttaagcta gctcctttgg cttttaaaaa    5400 aaatttttt tcaaatttct tcattaccta agggagcctg catctaaatt tctcaactag    5460
ttcagcctag ctgaattttc tagtgtgtaa tacactttgc ttccttctta ttggtgaaaa    5520 ccaggggat gagtggcttc catggagaga tttcctgatt tctcagggag gaaaaaagtg    5580
atgacattta ccactacttt tatgtttttc ccctttttcc aaattgataa ggatttctgg    5640
ttcctagtga tccgggattg ggcaacagtg cagaactgcc agtcatgccg taggccgtga    5700
agaaagaatg tgagtaactg ttgttttgca aggatttgta gggttatggg cagttgttgt    5760
ttgaagcatt gctatgacct aattcccaag gtatctttcc tctcttggtg ttctaggtaa    5820
gccaatgagc tttaatctct acttgctata accgtgtgct tagaaaaaga ggtgagagta    5880
gtggttttcc ttcaaactgt ccacattcat gaagattatg aattgttagg acagccaggg    5940
caagatagac cctgtctcta caaaaatttt tttctaaatt aaccgggcat ggtggtgcct    6000
gcctgtagtc ccacctgtgt gggagaatca cttgagcctg ggaggtcaag gctgcagtga    6060
gccatgattg caccccctgca ctccagcctg ggtgacagag tgagaccctg gctcaataag    6120 aggggaaaa aaaattgtta ggagctgggt gcggatgcag cctgcaatcc cagctacttg    6180
agaggctgag gccggaggat tgcttaaacc caagaatttg agcgtagcct gggcaacaca    6240
gcaagacccc atctaagaaa aaatgttttt ttaaatcagc ttagcccaaa ggggttgtga    6300
atggggaggt ataaaaagca aagattattt tttggctact aagccaagaa cttacaggga    6360 ttttttttt cagtcccaga acctacagat accctgctac ttgcttcacg tggatgctca    6420
gtgcccagca gccatcttaa tacattaaac cagtttaaaa aataccttcc atgtggagaa    6480
aaacatgtct ttttctcgcc tcaactttat ccacatgaaa tgtgtgccca tggctgggcg    6540
cagtggctca cctgtaatcc caacactttg ggaggctgaa gcaggcagat tgcttgaggc    6600
caggagttcg agaacagtct ggccaacatg gcgaaacctc atctctacta aaattacaaa    6660
aattagccgg gcatggtggc acatgcctgt aatcccagct acgtcaggag gctgaggcac    6720
aggaattgct tgaacccaag aggcagagga tgcaatgagc caagatcaca ccactgcact    6780
ccagccttgg cgacagaggg agactctgtc tcaaaaaaaa aaaaaaaagg tgtgcccagg    6840
cccctagcca ttgccatgtg cccagccaga gagccaaatt agagggctgg cttccctatc    6900
acacagaata aatgctagtg ctagccaatg atcccttgc ttttaatgta tagaaaatac    6960
tgttgttcct tttgtcattt ccagtgacat ctgttttcta agcagctctt ttctagggag    7020
gaaaccaaag gggctaggtt aagaccctaa tagaaatgtt ttttctaatc tctggtgagt    7080
ctggaagtgt cacattcaca gtccacccctt gggagtggct tggtggagct ggggacaagg    7140
ttttgtttac tacatagtgc acatgataaa tggcctttaaa ctgtgattct ttctggtagg    7200
ataagttata ataaactgac cctaaagaat gcaaaaaaaa aaaaaaaaa                7250
```

<210> SEQ ID NO 3
<211> LENGTH: 561
<212> TYPE: PRT
<213> ORGANISM: Homo sapiens

<400> SEQUENCE: 3

Met Arg Pro Glu Pro Gly Gly Cys Cys Arg Arg Thr Val Arg Ala
1               5                   10                  15

Asn Gly Cys Val Ala Asn Gly Glu Val Arg Asn Gly Tyr Val Arg Ser
            20                  25                  30

Ser Ala Ala Ala Ala Ala Ala Ala Gly Gln Ile His His Val
            35                  40                  45

Thr Gln Asn Gly Gly Leu Tyr Lys Arg Pro Phe Asn Glu Ala Phe Glu
    50                  55                  60

Glu Thr Pro Met Leu Val Ala Val Leu Thr Tyr Val Gly Tyr Gly Val
65                  70                  75                  80

Leu Thr Leu Phe Gly Tyr Leu Arg Asp Phe Leu Arg Tyr Trp Arg Ile
                85                  90                  95

Glu Lys Cys His His Ala Thr Glu Arg Glu Glu Gln Lys Asp Phe Val
            100                 105                 110

Ser Leu Tyr Gln Asp Phe Glu Asn Phe Tyr Thr Arg Asn Leu Tyr Met
            115                 120                 125

Arg Ile Arg Asp Asn Trp Asn Arg Pro Ile Cys Ser Val Pro Gly Ala
130                 135                 140

Arg Val Asp Ile Met Glu Arg Gln Ser His Asp Tyr Asn Trp Ser Phe
145                 150                 155                 160

Lys Tyr Thr Gly Asn Ile Ile Lys Gly Val Ile Asn Met Gly Ser Tyr
                165                 170                 175

Asn Tyr Leu Gly Phe Ala Arg Asn Thr Gly Ser Cys Gln Glu Ala Ala
            180                 185                 190

Ala Lys Val Leu Glu Glu Tyr Gly Ala Gly Val Cys Ser Thr Arg Gln
            195                 200                 205

Glu Ile Gly Asn Leu Asp Lys His Glu Glu Leu Glu Glu Leu Val Ala
    210                 215                 220

Arg Phe Leu Gly Val Glu Ala Ala Met Ala Tyr Gly Met Gly Phe Ala
225                 230                 235                 240

Thr Asn Ser Met Asn Ile Pro Ala Leu Val Gly Lys Gly Cys Leu Ile
                245                 250                 255

Leu Ser Asp Glu Leu Asn His Ala Ser Leu Val Leu Gly Ala Arg Leu
            260                 265                 270

Ser Gly Ala Thr Ile Arg Ile Phe Lys His Asn Asn Met Gln Ser Leu
            275                 280                 285

Glu Lys Leu Leu Lys Asp Ala Ile Val Tyr Gly Gln Pro Arg Thr Arg
    290                 295                 300

Arg Pro Trp Lys Lys Ile Leu Ile Leu Val Glu Gly Ile Tyr Ser Met
305                 310                 315                 320

Glu Gly Ser Ile Val Arg Leu Pro Glu Val Ile Ala Leu Lys Lys Lys
                325                 330                 335

Tyr Lys Ala Tyr Leu Tyr Leu Asp Glu Ala His Ser Ile Gly Ala Leu
            340                 345                 350

Gly Pro Thr Gly Arg Gly Val Val Glu Tyr Phe Gly Leu Asp Pro Glu
            355                 360                 365

Asp Val Asp Val Met Met Gly Thr Phe Thr Lys Ser Phe Gly Ala Ser
    370                 375                 380

Gly Gly Tyr Ile Gly Gly Lys Lys Glu Leu Ile Asp Tyr Leu Arg Thr
385                 390                 395                 400

His Ser His Ser Ala Val Tyr Ala Thr Ser Leu Ser Pro Pro Val Val

```
            405                 410                 415
Glu Gln Ile Ile Thr Ser Met Lys Cys Ile Met Gly Gln Asp Gly Thr
            420                 425                 430

Ser Leu Gly Lys Glu Cys Val Gln Gln Leu Ala Glu Asn Thr Arg Tyr
            435                 440                 445

Phe Arg Arg Leu Lys Glu Met Gly Phe Ile Ile Tyr Gly Asn Glu
450                 455                 460

Asp Ser Pro Val Val Pro Leu Met Leu Tyr Met Pro Ala Lys Ile Gly
465                 470                 475                 480

Ala Phe Gly Arg Glu Met Leu Lys Arg Asn Ile Gly Val Val Val
            485                 490                 495

Gly Phe Pro Ala Thr Pro Ile Ile Glu Ser Arg Ala Arg Phe Cys Leu
            500                 505                 510

Ser Ala Ala His Thr Lys Glu Ile Leu Asp Thr Ala Leu Lys Glu Ile
            515                 520                 525

Asp Glu Val Gly Asp Leu Leu Gln Leu Lys Tyr Ser Arg His Arg Leu
530                 535                 540

Val Pro Leu Leu Asp Arg Pro Phe Asp Glu Thr Thr Tyr Glu Glu Thr
545                 550                 555                 560

Glu

<210> SEQ ID NO 4
<211> LENGTH: 53
<212> TYPE: DNA
<213> ORGANISM: Artificial Sequence
<220> FEATURE:
<223> OTHER INFORMATION: Primer

<400> SEQUENCE: 4
gggacaagtt tgtacaaaaa agcaggctat gcggccggag cccggaggct gct        53

<210> SEQ ID NO 5
<211> LENGTH: 53
<212> TYPE: DNA
<213> ORGANISM: Artificial Sequence
<220> FEATURE:
<223> OTHER INFORMATION: Primer

<400> SEQUENCE: 5
ggggaccact ttgtacaaga aagctgggtc cgtcttctgt ttcttcatac gtc        53

<210> SEQ ID NO 6
<211> LENGTH: 26
<212> TYPE: DNA
<213> ORGANISM: Artificial Sequence
<220> FEATURE:
<223> OTHER INFORMATION: Primer

<400> SEQUENCE: 6
ccacaggccg gggtatggtg gagtac                                      26

<210> SEQ ID NO 7
<211> LENGTH: 26
<212> TYPE: DNA
<213> ORGANISM: Artificial Sequence
<220> FEATURE:
<223> OTHER INFORMATION: Primer

<400> SEQUENCE: 7
gtactccacc atacccggc ctgtgg                                       26
```

```
<210> SEQ ID NO 8
<211> LENGTH: 43
<212> TYPE: DNA
<213> ORGANISM: Artificial Sequence
<220> FEATURE:
<223> OTHER INFORMATION: Primer

<400> SEQUENCE: 8
gaacgttcac aaagagtttt gttgcttctg gaggatatat tgg          43

<210> SEQ ID NO 9
<211> LENGTH: 43
<212> TYPE: DNA
<213> ORGANISM: Artificial Sequence
<220> FEATURE:
<223> OTHER INFORMATION: Primer

<400> SEQUENCE: 9
ccaatatatc ctccagaagc aacaaaactc tttgtgaacg ttc          43

<210> SEQ ID NO 10
<211> LENGTH: 32
<212> TYPE: DNA
<213> ORGANISM: Artificial Sequence
<220> FEATURE:
<223> OTHER INFORMATION: Primer

<400> SEQUENCE: 10
ttcctgccac cccaattttt gagtccagag cc               32

<210> SEQ ID NO 11
<211> LENGTH: 32
<212> TYPE: DNA
<213> ORGANISM: Artificial Sequence
<220> FEATURE:
<223> OTHER INFORMATION: Primer

<400> SEQUENCE: 11
ggctctggac tcaaaaattg gggtggcagg aa               32

<210> SEQ ID NO 12
<211> LENGTH: 126
<212> TYPE: DNA
<213> ORGANISM: Artificial Sequence
<220> FEATURE:
<223> OTHER INFORMATION: Primer

<400> SEQUENCE: 12
gccactacct gagcccgttg tcagcgtagt ctgggacgtc gtatgggtaa gcgtagtctg     60
ggacgtcgta tgggtaagcg tagtctggga cgtcgtatgg gtagacaccc ctccttatta   120
catttc                                                              126

<210> SEQ ID NO 13
<211> LENGTH: 126
<212> TYPE: DNA
<213> ORGANISM: Artificial Sequence
<220> FEATURE:
<223> OTHER INFORMATION: Primer

<400> SEQUENCE: 13
gaaatgtaat aaggaggggt gtctacccat acgacgtccc agactacgct tacccatacg     60
acgtcccaga ctacgcttac ccatacgacg tcccagacta cgctgacaac gggctcaggt   120
agtggc                                                              126
```

<210> SEQ ID NO 14
<211> LENGTH: 36
<212> TYPE: DNA
<213> ORGANISM: Artificial Sequence
<220> FEATURE:
<223> OTHER INFORMATION: Primer

<400> SEQUENCE: 14
gcccaactgg tcgcggtatg tgtgaaatat ttggcg                          36

<210> SEQ ID NO 15
<211> LENGTH: 36
<212> TYPE: DNA
<213> ORGANISM: Artificial Sequence
<220> FEATURE:
<223> OTHER INFORMATION: Primer

<400> SEQUENCE: 15
cgccaaatat ttcacacata ccgcgaccag ttgggc                          36

<210> SEQ ID NO 16
<211> LENGTH: 42
<212> TYPE: DNA
<213> ORGANISM: Artificial Sequence
<220> FEATURE:
<223> OTHER INFORMATION: Primer

<400> SEQUENCE: 16
gtactttcac taagtcgttt gttgctgctg gtggttacat tg                   42

<210> SEQ ID NO 17
<211> LENGTH: 42
<212> TYPE: DNA
<213> ORGANISM: Artificial Sequence
<220> FEATURE:
<223> OTHER INFORMATION: Primer

<400> SEQUENCE: 17
caatgtaacc accagcagca acaaacgact tagtgaaagt ac                   42

<210> SEQ ID NO 18
<211> LENGTH: 43
<212> TYPE: DNA
<213> ORGANISM: Artificial Sequence
<220> FEATURE:
<223> OTHER INFORMATION: Primer

<400> SEQUENCE: 18
cttatcctgc tactccgctg tttgaatcaa gagtaagatt ctg                  43

<210> SEQ ID NO 19
<211> LENGTH: 43
<212> TYPE: DNA
<213> ORGANISM: Artificial Sequence
<220> FEATURE:
<223> OTHER INFORMATION: Primer

<400> SEQUENCE: 19
cagaatctta ctcttgattc aaacagcgga gtagcaggat aag                  43

<210> SEQ ID NO 20
<211> LENGTH: 40
<212> TYPE: DNA
<213> ORGANISM: Artificial Sequence
<220> FEATURE:

<223> OTHER INFORMATION: Primer

<400> SEQUENCE: 20
ctaatgggta ctttcactac ttcgtttggt gctgctggtg                             40

<210> SEQ ID NO 21
<211> LENGTH: 40
<212> TYPE: DNA
<213> ORGANISM: Artificial Sequence
<220> FEATURE:
<223> OTHER INFORMATION: Primer

<400> SEQUENCE: 21
caccagcagc accaaacgaa gtagtgaaag tacccattag                             40

<210> SEQ ID NO 22
<211> LENGTH: 20
<212> TYPE: DNA
<213> ORGANISM: Artificial Sequence
<220> FEATURE:
<223> OTHER INFORMATION: Primer

<400> SEQUENCE: 22
gagtccagag ccaggttttg                                                   20

<210> SEQ ID NO 23
<211> LENGTH: 19
<212> TYPE: DNA
<213> ORGANISM: Artificial Sequence
<220> FEATURE:
<223> OTHER INFORMATION: Primer

<400> SEQUENCE: 23
ctgagggagc accaaaaag                                                    19

<210> SEQ ID NO 24
<211> LENGTH: 23
<212> TYPE: DNA
<213> ORGANISM: Artificial Sequence
<220> FEATURE:
<223> OTHER INFORMATION: Primer

<400> SEQUENCE: 24
gagagggtta gggataggct tac                                               23

<210> SEQ ID NO 25
<211> LENGTH: 18
<212> TYPE: DNA
<213> ORGANISM: Artificial Sequence
<220> FEATURE:
<223> OTHER INFORMATION: Primer

<400> SEQUENCE: 25
gcagccattt ccggtttc                                                     18

<210> SEQ ID NO 26
<211> LENGTH: 18
<212> TYPE: DNA
<213> ORGANISM: Artificial Sequence
<220> FEATURE:
<223> OTHER INFORMATION: Primer

<400> SEQUENCE: 26
ggattgccca gcggatgg                                                     18

```
<210> SEQ ID NO 27
<211> LENGTH: 20
<212> TYPE: DNA
<213> ORGANISM: Artificial Sequence
<220> FEATURE:
<223> OTHER INFORMATION: Primer

<400> SEQUENCE: 27
ttacaggtgt gagccagtgc                                                  20

<210> SEQ ID NO 28
<211> LENGTH: 22
<212> TYPE: DNA
<213> ORGANISM: Artificial Sequence
<220> FEATURE:
<223> OTHER INFORMATION: Primer

<400> SEQUENCE: 28
tgtgcaaaaa tactaagatt tc                                               22

<210> SEQ ID NO 29
<211> LENGTH: 22
<212> TYPE: DNA
<213> ORGANISM: Artificial Sequence
<220> FEATURE:
<223> OTHER INFORMATION: Primer

<400> SEQUENCE: 29
cacaatcttg cacgtaatga aa                                               22

<210> SEQ ID NO 30
<211> LENGTH: 23
<212> TYPE: DNA
<213> ORGANISM: Artificial Sequence
<220> FEATURE:
<223> OTHER INFORMATION: Primer

<400> SEQUENCE: 30
cctcagctgc tactcctatt ttg                                              23

<210> SEQ ID NO 31
<211> LENGTH: 21
<212> TYPE: DNA
<213> ORGANISM: Artificial Sequence
<220> FEATURE:
<223> OTHER INFORMATION: Primer

<400> SEQUENCE: 31
tctgcttcct tttgtgtcac c                                                21

<210> SEQ ID NO 32
<211> LENGTH: 23
<212> TYPE: DNA
<213> ORGANISM: Artificial Sequence
<220> FEATURE:
<223> OTHER INFORMATION: Primer

<400> SEQUENCE: 32
tcagaaaaac aaagcattct tca                                              23

<210> SEQ ID NO 33
<211> LENGTH: 22
<212> TYPE: DNA
<213> ORGANISM: Artificial Sequence
<220> FEATURE:
<223> OTHER INFORMATION: Primer
```

```
<400> SEQUENCE: 33
agtctgaaaa ggacacaaca ca                                              22

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34
gctcactctg actgcttttc aa                                              22

<210> SEQ ID NO 35
<211> LENGTH: 20
<212> TYPE: DNA
<213> ORGANISM: Artificial Sequence
<220> FEATURE:
<223> OTHER INFORMATION: Primer

<400> SEQUENCE: 35
tgatcactgt gctgttgtgc                                                 20

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36
aagactggac cggaagaaca t                                               21

<210> SEQ ID NO 37
<211> LENGTH: 20
<212> TYPE: DNA
<213> ORGANISM: Artificial Sequence
<220> FEATURE:
<223> OTHER INFORMATION: Primer

<400> SEQUENCE: 37
tgaggcatgg tttctgaatg                                                 20

<210> SEQ ID NO 38
<211> LENGTH: 20
<212> TYPE: DNA
<213> ORGANISM: Artificial Sequence
<220> FEATURE:
<223> OTHER INFORMATION: Primer

<400> SEQUENCE: 38
tgctgactct gtttccaggt                                                 20

<210> SEQ ID NO 39
<211> LENGTH: 20
<212> TYPE: DNA
<213> ORGANISM: Artificial Sequence
<220> FEATURE:
<223> OTHER INFORMATION: Primer

<400> SEQUENCE: 39
acttcagcct ggacaatgga                                                 20

<210> SEQ ID NO 40
<211> LENGTH: 20
```

<212> TYPE: DNA
<213> ORGANISM: Artificial Sequence
<220> FEATURE:
<223> OTHER INFORMATION: Primer

<400> SEQUENCE: 40
gagcctaaac cagaggcaaa                                               20

<210> SEQ ID NO 41
<211> LENGTH: 21
<212> TYPE: DNA
<213> ORGANISM: Artificial Sequence
<220> FEATURE:
<223> OTHER INFORMATION: Primer

<400> SEQUENCE: 41
gaccatgttg gttgaccttg t                                             21

<210> SEQ ID NO 42
<211> LENGTH: 20
<212> TYPE: DNA
<213> ORGANISM: Artificial Sequence
<220> FEATURE:
<223> OTHER INFORMATION: Primer

<400> SEQUENCE: 42
gtccatggaa accacacacc                                               20

<210> SEQ ID NO 43
<211> LENGTH: 25
<212> TYPE: DNA
<213> ORGANISM: Artificial Sequence
<220> FEATURE:
<223> OTHER INFORMATION: Primer

<400> SEQUENCE: 43
aaatatttta tggtgaaatg gaaaa                                         25

<210> SEQ ID NO 44
<211> LENGTH: 22
<212> TYPE: DNA
<213> ORGANISM: Artificial Sequence
<220> FEATURE:
<223> OTHER INFORMATION: Primer

<400> SEQUENCE: 44
tggcatatgt accaaatgaa gg                                            22

<210> SEQ ID NO 45
<211> LENGTH: 20
<212> TYPE: DNA
<213> ORGANISM: Artificial Sequence
<220> FEATURE:
<223> OTHER INFORMATION: Primer

<400> SEQUENCE: 45
gcctgcatca ccaaagagtt                                               20

<210> SEQ ID NO 46
<211> LENGTH: 20
<212> TYPE: DNA
<213> ORGANISM: Artificial Sequence
<220> FEATURE:
<223> OTHER INFORMATION: Primer

<400> SEQUENCE: 46

| | |
|---|---|
| cactgtcacc ccctctgtct | 20 |

```
<210> SEQ ID NO 47
<211> LENGTH: 20
<212> TYPE: DNA
<213> ORGANISM: Artificial Sequence
<220> FEATURE:
<223> OTHER INFORMATION: Primer

<400> SEQUENCE: 47
```

| | |
|---|---|
| cctgccgaag gataatcttg | 20 |

```
<210> SEQ ID NO 48
<211> LENGTH: 21
<212> TYPE: DNA
<213> ORGANISM: Artificial Sequence
<220> FEATURE:
<223> OTHER INFORMATION: Primer

<400> SEQUENCE: 48
```

| | |
|---|---|
| gcaaaggaag gattagaagc a | 21 |

```
<210> SEQ ID NO 49
<211> LENGTH: 17
<212> TYPE: DNA
<213> ORGANISM: Artificial Sequence
<220> FEATURE:
<223> OTHER INFORMATION: Primer

<400> SEQUENCE: 49
```

| | |
|---|---|
| caaacggtgc agagacc | 17 |

```
<210> SEQ ID NO 50
<211> LENGTH: 23
<212> TYPE: DNA
<213> ORGANISM: Artificial Sequence
<220> FEATURE:
<223> OTHER INFORMATION: Primer

<400> SEQUENCE: 50
```

| | |
|---|---|
| aacccttcat aagatgaact cta | 23 |

```
<210> SEQ ID NO 51
<211> LENGTH: 21
<212> TYPE: DNA
<213> ORGANISM: Artificial Sequence
<220> FEATURE:
<223> OTHER INFORMATION: Primer

<400> SEQUENCE: 51
```

| | |
|---|---|
| taacaggaga atgctaacct t | 21 |

```
<210> SEQ ID NO 52
<211> LENGTH: 20
<212> TYPE: DNA
<213> ORGANISM: Artificial Sequence
<220> FEATURE:
<223> OTHER INFORMATION: Primer

<400> SEQUENCE: 52
```

| | |
|---|---|
| cactttagag aggagtaggc | 20 |

```
<210> SEQ ID NO 53
<211> LENGTH: 25
<212> TYPE: DNA
<213> ORGANISM: Artificial Sequence
```

```
<220> FEATURE:
<223> OTHER INFORMATION: Primer

<400> SEQUENCE: 53
agataacctt ctacctctgt tctaa                                    25

<210> SEQ ID NO 54
<211> LENGTH: 18
<212> TYPE: DNA
<213> ORGANISM: Artificial Sequence
<220> FEATURE:
<223> OTHER INFORMATION: Primer

<400> SEQUENCE: 54
ttgtcatcta gtggccat                                            18

<210> SEQ ID NO 55
<211> LENGTH: 19
<212> TYPE: DNA
<213> ORGANISM: Artificial Sequence
<220> FEATURE:
<223> OTHER INFORMATION: Primer

<400> SEQUENCE: 55
gaatcgtgca taatcctgg                                           19

<210> SEQ ID NO 56
<211> LENGTH: 19
<212> TYPE: DNA
<213> ORGANISM: Artificial Sequence
<220> FEATURE:
<223> OTHER INFORMATION: Primer

<400> SEQUENCE: 56
agagacagac acaaggaat                                           19

<210> SEQ ID NO 57
<211> LENGTH: 19
<212> TYPE: DNA
<213> ORGANISM: Artificial Sequence
<220> FEATURE:
<223> OTHER INFORMATION: Primer

<400> SEQUENCE: 57
aatcttggcc ttgttgaaa                                           19

<210> SEQ ID NO 58
<211> LENGTH: 21
<212> TYPE: DNA
<213> ORGANISM: Artificial Sequence
<220> FEATURE:
<223> OTHER INFORMATION: Primer

<400> SEQUENCE: 58
tctaacaagg acctactcag a                                        21

<210> SEQ ID NO 59
<211> LENGTH: 20
<212> TYPE: DNA
<213> ORGANISM: Artificial Sequence
<220> FEATURE:
<223> OTHER INFORMATION: Primer

<400> SEQUENCE: 59
ctgtccccac aagttgtttt                                          20
```

```
<210> SEQ ID NO 60
<211> LENGTH: 19
<212> TYPE: DNA
<213> ORGANISM: Artificial Sequence
<220> FEATURE:
<223> OTHER INFORMATION: Primer

<400> SEQUENCE: 60
gtcaccttga agagcagaa                                                   19

<210> SEQ ID NO 61
<211> LENGTH: 22
<212> TYPE: DNA
<213> ORGANISM: Artificial Sequence
<220> FEATURE:
<223> OTHER INFORMATION: Primer

<400> SEQUENCE: 61
tttaggtctg agtgtgaaca ta                                               22

<210> SEQ ID NO 62
<211> LENGTH: 22
<212> TYPE: DNA
<213> ORGANISM: Artificial Sequence
<220> FEATURE:
<223> OTHER INFORMATION: Primer

<400> SEQUENCE: 62
tctgtttagc taggaaaggt ga                                               22

<210> SEQ ID NO 63
<211> LENGTH: 19
<212> TYPE: DNA
<213> ORGANISM: Artificial Sequence
<220> FEATURE:
<223> OTHER INFORMATION: Primer

<400> SEQUENCE: 63
ggagggtatt tgttagtta                                                   19

<210> SEQ ID NO 64
<211> LENGTH: 19
<212> TYPE: DNA
<213> ORGANISM: Artificial Sequence
<220> FEATURE:
<223> OTHER INFORMATION: Primer

<400> SEQUENCE: 64
ggtgtggtga actgaattg                                                   19

<210> SEQ ID NO 65
<211> LENGTH: 19
<212> TYPE: DNA
<213> ORGANISM: Artificial Sequence
<220> FEATURE:
<223> OTHER INFORMATION: Primer

<400> SEQUENCE: 65
agggatggga ctagatgta                                                   19

<210> SEQ ID NO 66
<211> LENGTH: 20
<212> TYPE: DNA
<213> ORGANISM: Artificial Sequence
<220> FEATURE:
<223> OTHER INFORMATION: Primer
```

```
<400> SEQUENCE: 66
gggagattaa tgaggcagaa                                              20

<210> SEQ ID NO 67
<211> LENGTH: 17
<212> TYPE: DNA
<213> ORGANISM: Artificial Sequence
<220> FEATURE:
<223> OTHER INFORMATION: Primer

<400> SEQUENCE: 67
atgcttgcca agttgac                                                 17

<210> SEQ ID NO 68
<211> LENGTH: 19
<212> TYPE: DNA
<213> ORGANISM: Artificial Sequence
<220> FEATURE:
<223> OTHER INFORMATION: Primer

<400> SEQUENCE: 68
cataatctaa cgcctgtgc                                               19

<210> SEQ ID NO 69
<211> LENGTH: 19
<212> TYPE: DNA
<213> ORGANISM: Artificial Sequence
<220> FEATURE:
<223> OTHER INFORMATION: Primer

<400> SEQUENCE: 69
catattcctt ttttgtcag                                               19

<210> SEQ ID NO 70
<211> LENGTH: 19
<212> TYPE: DNA
<213> ORGANISM: Artificial Sequence
<220> FEATURE:
<223> OTHER INFORMATION: Primer

<400> SEQUENCE: 70
taaataaccc aagagaaac                                               19

<210> SEQ ID NO 71
<211> LENGTH: 19
<212> TYPE: DNA
<213> ORGANISM: Artificial Sequence
<220> FEATURE:
<223> OTHER INFORMATION: Primer

<400> SEQUENCE: 71
gctattaatc tgggctctg                                               19

<210> SEQ ID NO 72
<211> LENGTH: 24
<212> TYPE: DNA
<213> ORGANISM: Artificial Sequence
<220> FEATURE:
<223> OTHER INFORMATION: Primer

<400> SEQUENCE: 72
ggagaaatcc atttatattc cttg                                         24

<210> SEQ ID NO 73
```

```
<211> LENGTH: 50
<212> TYPE: PRT
<213> ORGANISM: Homo sapiens

<400> SEQUENCE: 73

Ser Ile Gly Ala Leu Gly Pro Thr Gly Arg Gly Val Val Glu Tyr Phe
1               5                   10                  15

Gly Leu Asp Pro Glu Asp Val Asp Val Met Met Gly Thr Phe Thr Lys
            20                  25                  30

Ser Phe Gly Ala Ser Gly Gly Tyr Ile Gly Gly Lys Lys Glu Leu Ile
        35                  40                  45

Asp Tyr
    50

<210> SEQ ID NO 74
<211> LENGTH: 50
<212> TYPE: PRT
<213> ORGANISM: Bos taurus

<400> SEQUENCE: 74

Ser Ile Gly Ala Leu Gly Pro Thr Gly Arg Gly Val Val Asp Tyr Phe
1               5                   10                  15

Gly Leu Asp Pro Glu Asp Val Asp Ile Met Met Gly Thr Phe Thr Lys
            20                  25                  30

Ser Phe Gly Ala Ser Gly Gly Tyr Ile Gly Gly Lys Lys Ala Leu Ile
        35                  40                  45

Asp Tyr
    50

<210> SEQ ID NO 75
<211> LENGTH: 50
<212> TYPE: PRT
<213> ORGANISM: Rattus norvegicus

<400> SEQUENCE: 75

Ser Ile Gly Ala Leu Gly Pro Ser Gly Arg Gly Val Val Asp Tyr Phe
1               5                   10                  15

Gly Leu Asp Pro Glu Asp Val Asp Val Met Met Gly Thr Phe Thr Lys
            20                  25                  30

Ser Phe Gly Ala Ser Gly Gly Tyr Ile Gly Gly Lys Lys Glu Leu Ile
        35                  40                  45

Asp Tyr
    50

<210> SEQ ID NO 76
<211> LENGTH: 50
<212> TYPE: PRT
<213> ORGANISM: Mus musculus

<400> SEQUENCE: 76

Ser Ile Gly Ala Leu Gly Pro Ser Gly Arg Gly Val Val Asp Tyr Phe
1               5                   10                  15

Gly Leu Asp Pro Glu Asp Val Asp Val Met Met Gly Thr Phe Thr Lys
            20                  25                  30

Ser Phe Gly Ala Ser Gly Gly Tyr Ile Gly Gly Lys Lys Glu Leu Ile
        35                  40                  45

Asp Tyr
    50
```

```
<210> SEQ ID NO 77
<211> LENGTH: 50
<212> TYPE: PRT
<213> ORGANISM: Danio rerio

<400> SEQUENCE: 77

Ser Ile Gly Ala Leu Gly Pro Gly Arg Gly Val Val Glu Tyr Phe
1               5                   10                  15

Gly Leu Asp Pro Arg Asp Val Asp Ile Met Met Gly Thr Phe Thr Lys
            20                  25                  30

Ser Phe Gly Ala Ala Gly Gly Tyr Ile Gly Gly Arg Lys Asp Leu Ile
        35                  40                  45

Asp Tyr
    50

<210> SEQ ID NO 78
<211> LENGTH: 50
<212> TYPE: PRT
<213> ORGANISM: Drosophila melanogaster

<400> SEQUENCE: 78

Ser Val Gly Ala Met Gly Ser Arg Gly Arg Gly Val Thr Asp Tyr Phe
1               5                   10                  15

Asn Val Asp Pro Lys Glu Val Asp Ile Leu Met Gly Thr Phe Thr Lys
            20                  25                  30

Ser Phe Gly Ser Ala Gly Gly Tyr Leu Ala Gly Ser Lys Lys Leu Ile
        35                  40                  45

Asp Phe
    50

<210> SEQ ID NO 79
<211> LENGTH: 50
<212> TYPE: PRT
<213> ORGANISM: Saccharomyces cerevisiae

<400> SEQUENCE: 79

Ser Ile Gly Ala Met Gly Pro Thr Gly Arg Gly Val Cys Glu Ile Phe
1               5                   10                  15

Gly Val Asp Pro Lys Asp Val Asp Ile Leu Met Gly Thr Phe Thr Lys
            20                  25                  30

Ser Phe Gly Ala Ala Gly Gly Tyr Ile Ala Ala Asp Gln Trp Ile Ile
        35                  40                  45

Asp Arg
    50

<210> SEQ ID NO 80
<211> LENGTH: 49
<212> TYPE: PRT
<213> ORGANISM: Sphingomonas paucimobilis

<400> SEQUENCE: 80

Ser Met Gly Phe Phe Gly Pro Asn Gly Arg Gly Val Tyr Glu Ala Gln
1               5                   10                  15

Gly Leu Glu Gly Gln Ile Asp Phe Val Val Gly Thr Phe Ser Lys Ser
            20                  25                  30

Val Gly Thr Val Gly Gly Phe Val Val Ser Asn His Pro Lys Phe Glu
        35                  40                  45

Ala
```

```
<210> SEQ ID NO 81
<211> LENGTH: 43
<212> TYPE: PRT
<213> ORGANISM: Homo sapiens

<400> SEQUENCE: 81

Gly Phe Pro Ala Thr Pro Ile Ile Glu Ser Arg Ala Arg Phe Cys Leu
1               5                   10                  15

Ser Ala Ala His Thr Lys Glu Ile Leu Asp Thr Ala Leu Lys Glu Ile
            20                  25                  30

Asp Glu Val Gly Asp Leu Leu Gln Leu Lys Tyr
        35                  40

<210> SEQ ID NO 82
<211> LENGTH: 43
<212> TYPE: PRT
<213> ORGANISM: Bos taurus

<400> SEQUENCE: 82

Gly Phe Pro Ala Thr Pro Ile Ile Glu Ser Arg Ala Arg Phe Cys Leu
1               5                   10                  15

Ser Ala Ala His Thr Arg Glu Thr Leu Asp Thr Ala Leu Lys Glu Ile
            20                  25                  30

Asp Glu Val Gly Asp Leu Leu His Leu Lys Tyr
        35                  40

<210> SEQ ID NO 83
<211> LENGTH: 43
<212> TYPE: PRT
<213> ORGANISM: Rattus norvegicus

<400> SEQUENCE: 83

Gly Phe Pro Ala Thr Pro Ile Ile Glu Ser Arg Ala Arg Phe Cys Leu
1               5                   10                  15

Ser Ala Ala His Thr Lys Glu Leu Leu Asp Thr Ala Leu Lys Glu Ile
            20                  25                  30

Asp Glu Val Gly Asp Leu Leu Gln Leu Lys Tyr
        35                  40

<210> SEQ ID NO 84
<211> LENGTH: 43
<212> TYPE: PRT
<213> ORGANISM: Mus musculus

<400> SEQUENCE: 84

Gly Phe Pro Ala Thr Pro Ile Ile Glu Ser Arg Ala Arg Phe Cys Leu
1               5                   10                  15

Ser Ala Ala His Thr Lys Glu Ile Leu Asp Thr Ala Leu Lys Glu Ile
            20                  25                  30

Asp Glu Val Gly Asp Leu Leu Gln Leu Lys Tyr
        35                  40

<210> SEQ ID NO 85
<211> LENGTH: 43
<212> TYPE: PRT
<213> ORGANISM: Danio rerio

<400> SEQUENCE: 85

Gly Phe Pro Ala Thr Pro Ile Ile Glu Ser Arg Ala Arg Phe Cys Ile
1               5                   10                  15

Ser Ala Ala His Ser Lys Glu Met Leu Asp Arg Ala Leu Asp Val Ile
```

```
                       20                  25                  30

Ser Glu Val Gly Asp Leu Leu Gln Leu Lys Tyr
            35                  40

<210> SEQ ID NO 86
<211> LENGTH: 43
<212> TYPE: PRT
<213> ORGANISM: Drosophila melanogaster

<400> SEQUENCE: 86

Gly Phe Pro Ala Thr Pro Ile Met Glu Gly Arg Ile Arg Phe Cys Leu
1               5                   10                  15

Ser Ala Ala His Thr Lys Glu Gln Leu Asp Phe Ala Leu Glu Ala Ile
                20                  25                  30

Asp Glu Ile Ala Asp Asp Leu Gly Leu Lys Tyr
            35                  40

<210> SEQ ID NO 87
<211> LENGTH: 50
<212> TYPE: PRT
<213> ORGANISM: Saccharomyces cerevisiae

<400> SEQUENCE: 87

Ala Tyr Pro Ala Thr Pro Leu Ile Glu Ser Arg Val Arg Phe Cys Met
1               5                   10                  15

Ser Ala Ser Leu Thr Lys Glu Asp Ile Asp Tyr Leu Leu Arg His Val
                20                  25                  30

Ser Glu Val Gly Asp Lys Leu Asn Leu Lys Ser Asn Ser Gly Lys Ser
            35                  40                  45

Ser Tyr
    50

<210> SEQ ID NO 88
<211> LENGTH: 43
<212> TYPE: PRT
<213> ORGANISM: Sphingomonas paucimobilis

<400> SEQUENCE: 88

Arg Pro Pro Ala Thr Pro Ala Gly Thr Phe Leu Leu Arg Cys Ser Ile
1               5                   10                  15

Cys Ala Glu His Thr Pro Ala Gln Ile Gln Thr Val Leu Gly Met Phe
                20                  25                  30

Gln Ala Ala Gly Arg Ala Val Gly Val Ile Gly
            35                  40
```

MUTATIONS IN SPTLC2 GENE ASSOCIATED WITH SENSORY NEUROPATHY

CROSS-REFERENCE TO RELATED APPLICATION

This application is a continuation of U.S. patent application Ser. No. 13/823,080, filed May 28, 2013, which is the U.S. National Stage of International Patent Application No. PCT/EP2011/066212, filed Sep. 19, 2011, which claims priority from U.S. Provisional Patent Application No. 61/403,619, filed Sep. 17, 2010, and Great Britain Application No. 1015581.0, filed Sep. 17, 2010. The contents of these applications are incorporated herein by reference in their entirety.

The patent or application file contains at least one drawing executed in color. Copies of this patent or patent application publication with color drawing(s) will be provided by the Office upon request and payment of the necessary fee.

TECHNICAL FIELD

The present invention relates to a method and kit for identifying a subject at risk of, or having, a sensory neuropathy related disease. In particular, the present invention is based on the determination of mutations in the SPTLC2 gene causing said sensory neuropathies.

BACKGROUND OF THE INVENTION

Hereditary sensory neuropathies (HSNs) form part of the inherited peripheral neuropathies which are generally subdivided into three categories, reflecting the selective or predominant involvement of the motor or sensory peripheral nervous system. The most common variants are the hereditary motor and sensory neuropathies (HMSNs), also called Charcot-Marie-Tooth syndrome, in which both the motor and sensory nerves are affected (Dyck et al. 1993). When only the peripheral motor nervous system is affected, the neuropathy is classified as distal hereditary motor neuropathy (Harding 1993). In contrast, sensory dysfunction prevails in the HSNs. As the autonomic nervous system is involved to a varying degree in HSNs they are often referred to as hereditary sensory and autonomic neuropathies (HSANs) (Dyck 1993).

The HSNs/HSANs are a clinically and genetically heterogeneous group of disorders. Patients usually exhibit prominent distal sensory loss with manifest insensitivity to pain in some. The prominent distal sensory loss frequently leads to chronic ulcerations in feet and hands, sometimes resulting in severe complications such as extensive soft tissue infections, osteomyelitis necessitating amputations of toes and fingers or, in rare instances, even of more proximal parts of the extremities (Dyck 1993). Autonomic dysfunction, such as anhidrosis, fever, blood pressure fluctuations and gastro-intestinal disturbances are present in some patients. Electrophysiologically, axonal nerve damage of sensory neurons is often found, but additional demyelination may also be present (Auer-Grumbach et al. 2003).

HSAN can be transmitted as an autosomal dominant (AD) or autosomal recessive (AR) trait. Isolated patients have also been described (Dyck 1993; Auer-Grumbach 2004). The AD types of HSAN usually present in the second or third decade of life with marked sensory involvement and minimal autonomic and variable motor involvement, while AR HSAN present either as congenital syndromes with striking sensory and autonomic abnormalities or as almost pure autonomic disorders (Verpoorten et al. 2006a).

A classification of the hereditary sensory neuropathies into types HSAN I-V (Dyck, 1993) was made based on age at onset, inheritance pattern and additional features. Molecular genetic research has shown that at least seven genes are associated with the different types of HSNs/HSANs (located on the worldwide web at www.molgen.ua.ac.be/CMTMutations/). Two genes have been associated with AD HSAN: missense mutations in serine palmitoyltransferase (SPT) long chain subunit 1 (SPTLC1) are found in families and individuals with HSAN type I, an adult-onset sensory neuropathy (Bejaoui et al. 2001; Dawkins et al. 2001). Mutations in the small GPTase late endosomal protein RAB7, cause CMT2B (Verhoeven et al. 2003; Meggouh et al. 2006). Mutations in the WNK1/HSN2 gene (protein kinase with-no-lysine(K)-1/hereditary sensory neuropathy type 2) and FAM134B cause AR HSAN type II, an early-onset ulcero-mutilating sensory neuropathy (Lafreniere et al. 2004; Kurth et al. 2009). HSAN type III, also known as Familial Dysautonomia or Riley-Day syndrome, presents with typical prominent autonomic manifestations early in life and is caused by mutations in the inhibitor of kappa-light polypeptide gene enhancer in B cells, kinase complex associated protein (IKBKAP) (Slaugenhaupt et al. 2001). Mutations in neurotrophic tyrosine kinase, receptor type 1 (NTRK1) are reported in families with congenital insensitivity to pain, anhidrosis and mental retardation (CIPA or HSAN type IV) (Indo et al. 1996). HSAN type V, a phenotype closely related to CIPA but with normal mental development and less pronounced anhidrosis, can be caused by mutations in nerve growth factor beta (NGFB) (Einarsdottir et al. 2004) but also by NTRK1-mutations (Houlden et al. 2001; Einarsdottir et al. 2004). Apart from these six HSAN subtypes other forms with distinct additional features exist, e.g., HSAN with gastroesophageal reflux and cough (Kok et al. 2003) and HSAN with spastic paraplegia (Bouhouche et al. 2006b). Recently, the gene for this last form has been identified as cytosolic chaperonin-containing t-complex peptide-1 (CCT5) (Bouhouche et al. 2006a).

The identification of causative genes for the HSAN forms in recent years has provided preliminary insights in the pathogenesis of these rare neuropathies although the fundamental underlying pathomechanisms still remain to be unveiled (Verhoeven et al. 2006). Additional descriptions of HSAN families and patients with known or novel genetic defects are needed to further refine the existing classification and to get a better insight into the molecular basis of these disorders.

SUMMARY OF THE INVENTION

The present invention has identified for the first time a clear link between nucleic acid variations in the SPTLC2 gene and sensory neuropathies. Accordingly, said new genetic markers provide a reliable diagnosis of or prediction of the risk to develop a sensory neuropathy related disease or disorder. Identification of such a genetic variation may not only provide insight as to why the response to treatment varies amongst individuals, but also may potentially decrease morbidity and mortality through improved risk assessment and the administration of personalized medicine.

Accordingly, the present invention provides a method and kit for identifying a subject at risk of, or having, a sensory neuropathy disease, comprising detecting the presence or absence of at least one nucleic acid variant in the SPTLC2 gene, whereby the presence of at least one nucleic acid variant identifies whether a subject is at risk of or has a sensory neuropathy disease. Specific regions of interest in the SPTLC2 gene are the coding region of the SPTLC2 gene. The sensory neuropathy disease preferably is a hereditary sensory and autonomic neuropathy disease selected from the group consisting of HSAN type 1, HSAN type 2, HSAN type 3, HSAN type 4 and HSAN type 5.

The methods and kits of the present invention can be carried out in combination with other methods for identifying a subject at risk of, or having, a sensory neuropathy disease. In a preferred embodiment the methods and kits are carried out in combination with a method for the detection of the presence or absence of a nucleic acid variant, or other markers, in any other gene.

Any detection method for the diagnosis and/or prognosis of a sensory neuropathy related disease or disorder forms part of the present invention. Preferred methods and means for the detection of the presence or absence of the nucleic acid variants of the present invention are hybridization, sequencing, PCR, primer extension, MLPA, OLA, restriction site analysis or high-resolution melting analysis for mutation scanning, or a combination thereof.

A further embodiment of the present invention relates to a method for selecting an appropriate treatment or therapeutic agent for a subject at risk of, or having, a sensory neuropathy disease, comprising determining the status of the sensory neuropathy disease by the methods of the present invention and selecting an appropriate treatment or therapeutic agent.

DESCRIPTION OF THE DRAWINGS

FIGS. 2A-2C Missense mutations in SPTLC2 are associated with HSAN-I. (A) Sequence trace files of the G382V mutation in families CMT-1117 (proband indicated by arrow) and CMT-1044. (B) Isolated patient CMT-747.1:1 with the V359M mutation. (C) Patient CMT-635.II:1 carrying a de novo I504F mutation.

FIGS. 3A-3B. Conservation of mutations among species and structural view of the bacterial SPT enzyme (A) ClustalW multiple protein alignment of the SPTLC2 orthologues from human (*Homo sapiens*), mouse (*Musmusculus*), rat (*Rattusnorvegicus*), taurus (*Bos Taurus*), zebrafish (*Daniorerio*), fly (*Drosophila melanogaster*), baker's yeast (*Saccharomyces cerevisiae*) and Gram-negative bacteria with SPT-activity (*Sphingomonaspaucimobilis*). (B) SPT structure of the *Sphingomonaspaucinobilis* SPT homodimer (PDB ID: 2JGT) with the dimeric subunits represented in red and blue. The highlighted amino acids (V246, G268 and G385) correspond to the amino acids (V359, G382 and I504) mutated in the HSAN-I patients (see alignment in panel A).

DETAILED DESCRIPTION OF THE INVENTION

Definitions

Figure 1:
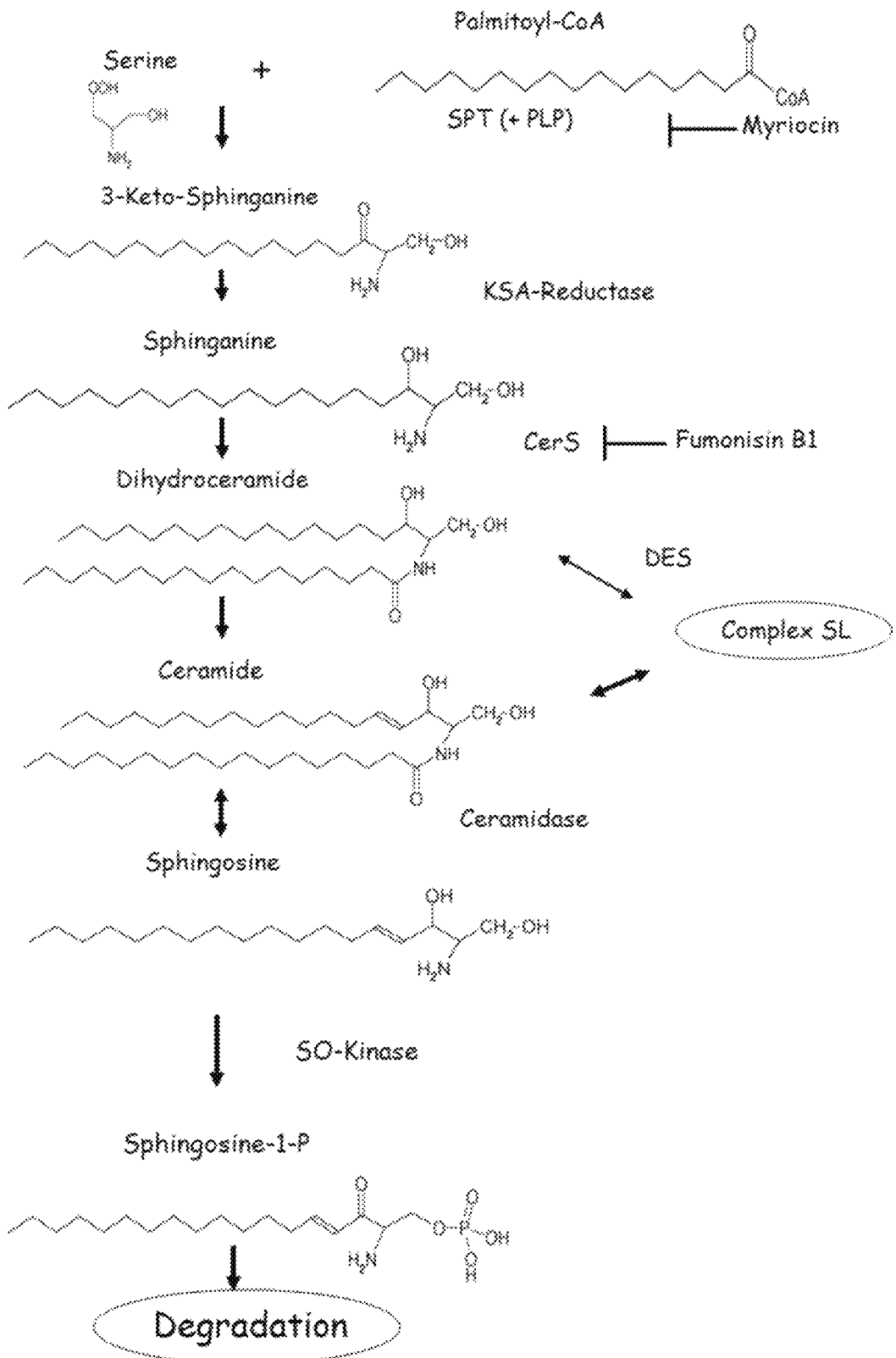
FIG. 1. De novo sphingolipid biosynthesis pathway. Left: the canonical pathway with L-serine; right the alternative, disease-related pathway with L-alanine. Condensation with L-alanine instead of L-serine gives rise to a metabolite lacking the CI hydroxyl group, obstructing conversion to complex SLs and degradation. The enzymes of the pathway are denoted in green. Myriocin and Fumonisin B1 are mycotoxins inhibiting the enzymes SPT and CerS respectively. SPT: serine palmitoyltransferase; PLP: pyridoxal-5'-phosphate; KSA: 3-keto-sphinganine; CerS: Ceramide synthase; DES: dihydroceramidedesaturase; SO: sphingosine; SL: sphingholipids.
Figure 1:
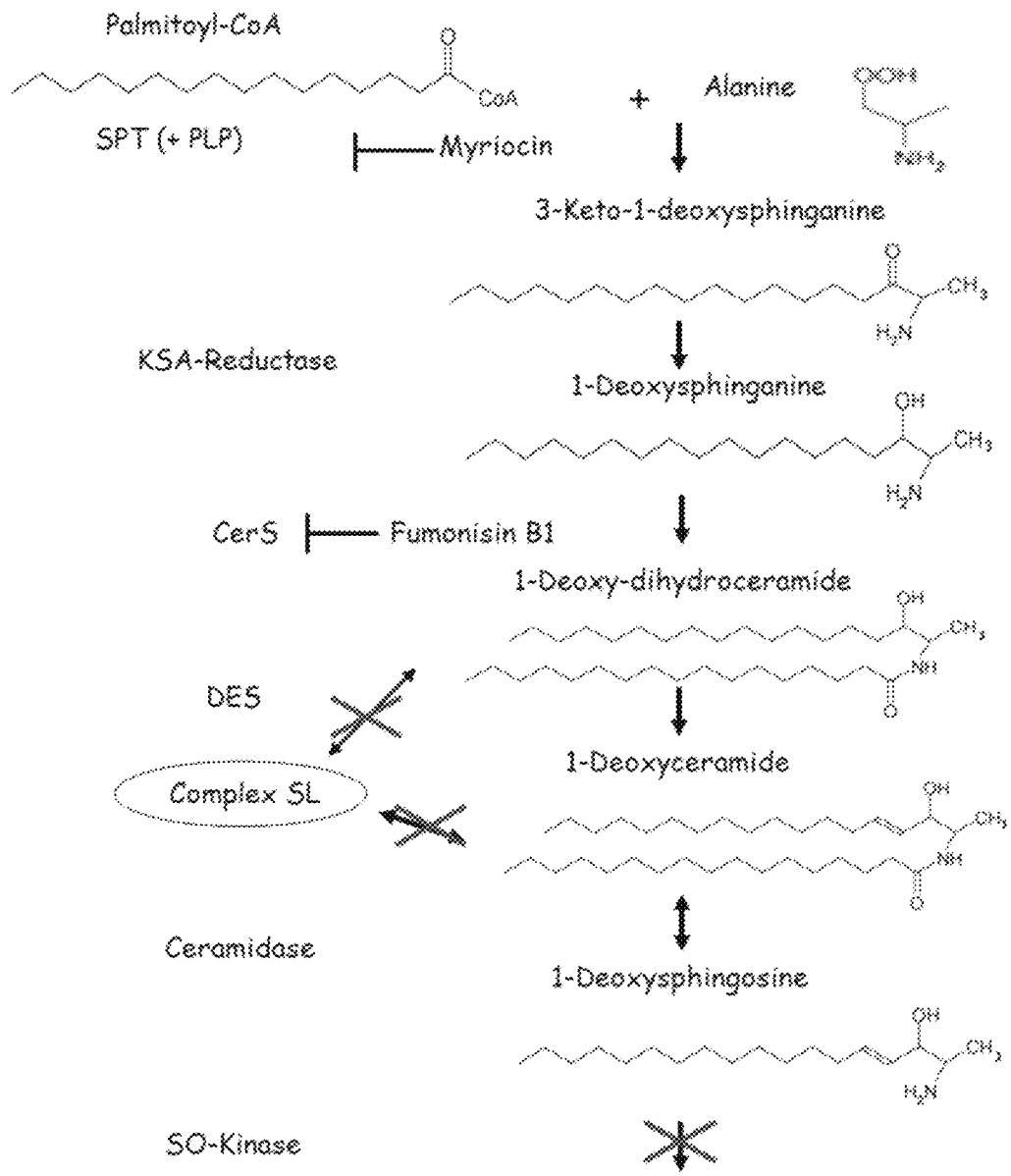

The present invention will be described with respect to particular embodiments and with reference to certain drawings but the invention is not limited thereto but only by the claims. Any reference signs in the claims shall not be construed as limiting the scope. The drawings described are only schematic and are non-limiting. In the drawings, the size of some of the elements may be exaggerated and not drawn on scale for illustrative purposes. Where the term "comprising" is used in the present description and claims, it does not exclude other elements or steps. Where an indefinite or definite article is used when referring to a singular noun e.g., "a" or "an," "the," this includes a plural of that noun unless something else is specifically stated.

Unless otherwise defined herein, scientific and technical terms and phrases used in connection with the present invention shall have the meanings that are commonly understood by those of ordinary skill in the art. Further, unless otherwise required by context, singular terms shall include the plural and plural terms shall include the singular. Generally, nomenclatures used in connection with, and techniques of biochemistry, enzymology, molecular and cellular biology, microbiology, genetics and protein and nucleic acid chemistry and hybridization described herein are those well known and commonly used in the art. The methods and techniques of the present invention are generally performed according to conventional methods well known in the art and as described in various general and more specific references that are cited and discussed throughout the present specification unless otherwise indicated. See, for example, Sambrook et al. Molecular Cloning: A Laboratory Manual, 2d ed., Cold Spring Harbor Laboratory Press, Cold Spring Harbor, N.Y. (1989); Ausubel et al., Current Protocols in Molecular Biology, Greene Publishing Associates (1992, and Supplements to 2002); Harlow and Lane, Antibodies: A Laboratory Manual, Cold Spring Harbor Laboratory Press, Cold Spring Harbor, N.Y. (1990); Taylor and Drickamer, Introduction to Glycobiology, Oxford Univ. Press (2003); Worthington Enzyme Manual, Worthington Biochemical Corp., Freehold, N.J.; Handbook of Biochemistry: Section A Proteins, Vol I. CRC Press (1976); Handbook of Biochemistry: Section A Proteins, Vol π, CRC Press (1976).

As used herein, the terms "polypeptide," "protein," "peptide" are used interchangeably and refer to a polymeric form of amino acids of any length, which can include coded and non-coded amino acids, chemically or biochemically modified or derivatized amino acids, and polypeptides having modified peptide backbones.

As used herein, the terms "nucleic acid," "polynucleotide," "polynucleic acid" are used interchangeably and refer to a polymeric form of nucleotides of any length, either deoxyribonucleotides or ribonucleotides, or analogs thereof. Polynucleotides may have any three-dimensional structure, and may perform any function, known or unknown. Non-limiting examples of polynucleotides include a gene, a gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, control regions, isolated RNA of any sequence, nucleic acid probes, and primers. The nucleic acid molecule may be linear or circular. A nucleic acid that is up to about 100 nucleotides in length, is often also referred to as an oligonucleotide.

As used herein, the term "allele" is one of several alternative forms of a gene or DNA sequence at a specific chromosomal location (locus). At each autosomal locus an individual possesses two alleles, one inherited from the father and one from the mother. The term "genotype" means the genetic constitution of an individual, either overall or at a specific locus.

As used herein, the term "homozygous" refers to having two of the same alleles at a locus. The term "heterozygous" refers to having different alleles at a locus.

As used herein, the terms "disorder" and "disease" are used interchangeably.

DETAILED DESCRIPTION

Systematic screening of the known HSAN genes in a large series of patients yielded pathogenic mutations in only 19% of probands (Rotthier et al. 2009), suggesting the involvement of other disease associated genes. By screening a set of functional candidate genes in a large HSAN cohort, the present inventors identified three heterozygous missense mutations in the SPTLC2 subunit of serine palmitoyltransferase (SPT), the first and rate-limiting enzyme in the de novo sphingolipid biosynthesis pathway, in four index patients presenting with a typical HSAN type I phenotype. This is particularly surprising since SPTLC2 was previously excluded as a cause for HSAN type I (Dawkins et al. 2002). Moreover, these mutations result in a partial to complete loss of SPT-activity and cause the formation of 1-deoxysphinganine, a neurotoxic metabolite. So, the present findings extend the genetic heterogeneity in HSAN related diseases and enlarge the group of HSAN neuropathies associated with SPT defects.

Thus, according to a first aspect, the invention relates to a method of identifying a subject at risk of, or having, a sensory neuropathy disease, comprising detecting the presence or absence of at least one nucleic acid variant in the SPTLC2 gene or a part thereof, whereby the presence of at least one nucleic acid variant identifies whether a subject is at risk of or has a sensory neuropathy disease.

As used herein, the term "SPTLC2 gene" refers to the gene encoding the second subunit of the serine palmitoyltransferase (SPT). The SPT enzyme is a multisubunit structure, consisting of dimeric subunits of SPTLC1 with either SPTLC2 or SPTLC3 (Hornemann et al. 2007). It is associated with the endoplasmic reticulum (ER) where it catalyzes the pyridixal-5'phosphate (PLP) dependent condensation of L-serine with palmitoyl-CoA. This is the first and rate-limiting step in the de novo biosynthesis of sphingolipids (see also FIG. 1). Sphingolipids are essential components of all eukaryotic cells where they play important roles in membrane structure and in intracellular signaling.

The reference nucleic acid and protein sequences indicated in the current invention are derived from GeneBank (NCBI) and indicated by their respective accession number, as is well known to the person skilled in the art. Frequent updates of the nomenclature for the description of sequence variations are provided on the website of the Human Genome Variation Society. Accordingly, the nucleotide numbering of the coding DNA and RNA reference sequence is as follows: nucleotide +1 is the A of the ATG-translation initiation codon, there is no nucleotide 0, the nucleotide 5' of the ATG-translation initiation codon is −1. The nucleotide number is preceded by "g." when a genomic or by "c." when a cDNA reference sequence is used. Substitutions are designated by ">". Similarly, the amino acid number is preceded by "p" when a protein reference sequence is used.

The human SPTLC2 gene (serine palmitoyltransferase long chain subunit 2) is located at chromosome 14 at location 14q24.3 and comprises 12 exons. The reference nucleic acid sequence for the human SPTLC2 is NC_000014.8 (gDNA; Version: NC_000014.8 GI:224589805; Region: complement(77973269 . . . 78083109); SEQ ID NO:1) or NM_004863 (cDNA; Version: NM_004863.2 GI:31881646; SEQ ID NO:2). The reference protein sequence encoded by the human SPTLC2 gene is NP_004854 (Version: NP_004854.1 GI:4758668; SEQ ID NO:3).

The term "nucleic acid variant" or "polymorphism" or "variant" as used in the present invention, means that the nucleic acid sequence at a certain position in the SPTLC2 gene differs relative to one or more reference nucleic acid sequences. The most simple nucleic acid polymorphism is a polymorphism affecting a single nucleotide, i.e., a single nucleotide polymorphism or SNP. Nucleic acid polymorphisms further include any number of contiguous and/or non-contiguous differences in the primary nucleotide sequence of the nucleic acid under investigation relative to the primary nucleotide sequence of one or more reference nucleic acids. The term "polymorphic position" or "position" refers to the nucleic acid position at which a nucleic acid polymorphism arises. Nucleic acid sequences comprising at least one such polymorphism are referred to as "polymorphic nucleic acid sequences," "polymorphic polynucleotides," "polymorphic sequences" or the like. The polymorphism or nucleic acid variant can be an insertion, deletion, substitution, tandem repeat or similar.

The phrase "detecting the presence or absence," e.g., of a genetic marker as used herein, refers to determining whether or not the relevant genetic event, linked with the occurrence of a disease, is present. In practice, both the absence and the presence of a certain event can function as markers. Accordingly, reference to detecting the presence of a nucleic acid variant generally encompasses determining whether the marker is present, either based on the absence or the presence of the variant in a sample. Moreover, this also includes the possible finding that the marker is not present in the sample, i.e., determining the absence (or presence) of a nucleic acid variant. In both cases determining the presence of the marker can also be done indirectly, e.g., where the presence of a nucleic acid variant is linked to disease, the occurrence of this marker can also be done by determining the homozygous presence of the corresponding allele not comprising the nucleic acid variant. Similarly, allele specific oligonucleotide primers and probes for detecting the presence of a SNP can be specific for the allele where the SNP is not present.

In a specific embodiment, the present invention relates to a method according to the present invention, wherein the SPTLC2 genotype has at least one variant allele of the SPTLC2 gene (heterozygous). In a further embodiment, the method of the invention relates to a method according to the present invention, wherein the SPTLC2 genotype has two variant or wild-type alleles of the SPTLC2 gene (homozygous).

The method of the present invention is particularly suited for the diagnosis and/or prognosis of a sensory neuropathy related disease or disorder in a subject, preferably a human. A sensory neuropathy related disease includes, without limitation, a hereditary sensory neuropathy (HSN), otherwise referred to as hereditary sensory and autonomic neuropathy (HSAN), which can be further classified into HSAN type 1, HSAN type 2, HSAN type 3, HSAN type 4 and HSAN type 5 (see Background section). With the methods of the present invention, the risk for developing a sensory neuropathy disorder can be determined. The "subject" on which the method of the present invention is carried out can be any subject for which the diagnosis/prognosis/risk of an sensory neuropathy needs to be determined. The subject may be a non-human subject such as (but not limited to) a cow, a pig, a sheep, a goat, a horse, a monkey, a rabbit, a dog, a cat, a mouse, a rat, a hamster, a zebrafish, a pufferfish (Fugu), a fly, a worm or C. elegans. More preferably, the subject is a primate. Even more preferably, the subject is a human.

In a further embodiment, the method of the invention comprises the step of determining whether one or more nucleic acid variants in the SPTLC2 gene are present in 0, 1 or 2 copies, more particularly whether a nucleic acid variant in the SPTLC2 gene is present in one or both alleles.

In another embodiment of the above method the presence or absence of the nucleic acid variant can be detected in the SPTLC2 gene or part thereof. Within the present context, "part thereof" refers to the region of interest, i.e., the region of the SPTLC2 gene comprising a nucleic acid variant. More particular, "a part thereof" refers to the 5'UTR, the promoter region, exon 1, intron 1, exon 2, intron 2, exon 3, intron 3, exon 4, intron 4, exon 5, intron 5, exon 6, intron 6, exon 7, intron 7, exon 8, intron 8, exon 9, intron 9, exon 10, intron 10, exon 11, intron 11, exon 12, and/or intron 12. Preferably, the polymorphism is located in the promoter region and/or in the coding region of the SPTLC2 gene, e.g., in at least one of the exons of the SPTLC2 gene. Typically, the nucleic acid variant is, without limitation, a substitution, deletion, insertion, duplication, translocation and/or inversion of at least one nucleotide.

The invention relates in particular to any polymorphism located within the coding region of the SPTLC2 gene as can be identified in the cDNA sequence (SEQ ID NO:2). More particularly, the nucleic acid variant is detected in at least one position of the coding region of the SPTLC2 gene including, without limitation, position 1145, 1075 or 1510 of the cDNA sequence. More specific, the nucleic acid variant is c.1145G>T, resulting in the amino acid change G382V. Or, the nucleic acid variant is c.1075G>A, resulting in the amino acid change V359M. Or, the nucleic acid variant is c.1510A>T, resulting in the amino acid change I504F.

As used herein, the term "wild-type" sequence is analogous to the "reference" sequence, and both terms are used interchangeably herein. The reference sequence for e.g., the wild-type human SPTLC2 gene can be the genomic DNA sequence as identified by NC_000014 (gDNA; Version: NC_000014.8 GI:224589805; SEQ ID NO:1) or the cDNA sequence including the coding sequence as identified by NM_004863 (cDNA; Version: NM_004863.2 GI:31881646; SEQ ID NO:2). For example, the allele may be normal as in the reference sequence(s), or it may be a variant, such as a structural or a non-structural variant. The amino acid sequence of the wild-type human SPTLC2 protein is identified by SEQ ID NO:3.

It will be apparent to the person skilled in the art that there are a large number of analytical procedures which may be used to detect the presence or absence of the nucleic acid variants mentioned herein. Nucleic acid from any nucleated cell can be used as the starting point for such assay techniques and may be isolated according to standard nucleic acid preparation procedures well known to those of skill in the art. Many current methods for the detection of allelic variation are reviewed by Nollau et al. (1997), and in standard textbooks, for example, "Laboratory Protocols for Mutation Detection," Ed. by U. Landegren, Oxford University Press, 1996 and "PCR," $2^{nd}$ Edition" by Newton & Graham, BIOS Scientific Publishers Limited, 1997 (incorporated herein by reference).

The method of the present invention can be carried out in vivo or in vitro. Preferred, however, is in vitro detection of nucleic acid variants in the SPTLC2 gene in a biological sample obtained from the subject. The term "biological sample" means a tissue sample or a body fluid sample. A tissue sample includes, but is not limited to, buccal cells, a brain sample, a skin sample, organ sample, placental tissue or fetal cells. The term "body fluid" refers to all fluids that are present in the body including but not limited to blood, plasma, serum, lymph, synovial fluid, amniotic fluid, urine, saliva or cerebrospinal fluid. The biological sample may also be obtained by subjecting it to a pretreatment if necessary, for example, by homogenizing or extracting. Such a pretreatment may be selected appropriately by those skilled in the art depending on the biological sample to be subjected.

A nucleic acid comprising an intended sequence prepared from a biological sample may be prepared from DNA (e.g., gDNA or cDNA) or RNA (e.g., mRNA). Release, concentration and isolation of the nucleic acids from the sample can be done by any method known in the art. Currently, various commercial kits are available such as the QIAamp Blood Kit from Qiagen (Hilden, Germany) for the isolation of nucleic acids from blood samples, or the "High pure PCR Template Preparation Kit" (Roche Diagnostics, Basel, Switzerland) or the DNA purification kits (PureGene, Gentra, Minneapolis, US). Other, well-known procedures for the isolation of DNA or RNA from a biological sample are also available (Sambrook et al., 1989; Ausubel et al., 2003).

When the quantity of the nucleic acid is low or insufficient for the assessment, the nucleic acid may be amplified. Such amplification procedures can be accomplished by those methods known in the art, including, for example, the polymerase chain reaction (PCR), ligase chain reaction (LCR), nucleic acid sequence-based amplification (NASBA), strand displacement amplification, rolling circle amplification, T7-polymerase amplification, and reverse transcription polymerase reaction (RT-PCR).

After performing the extraction and/or amplification procedure, the presence or absence of certain nucleic acid variants in the target sequence can be detected. Numerous methods for detecting a single nucleotide anomaly in nucleic acid sequences are well-known in the art. The present invention is not limited by any particular method used to detect the target sequences disclosed herein. Examples of such methods are described by Gut (2001) and Syvanen (2001), and include, but are not limited to, hybridization methods such as reverse dot blot, Line Probe Assay (LiPA), geneChip™ microarrays, dynamic allel-specific hybridization (DASH), peptide nucleic acid (PNA) and locked nucleic acid (LNA) probes, TaqMan™ (5'nuclease assay) and molecular beacons; allele-specific PCR methods such as intercalating dye, FRET primers and Alphascreen™; primer extension methods such as ARMS, kinetic PCR, SNPstream™, Genetic Bit Analysis™ (GBA), multiplex minisequencing, SNaPshot, pyrosequencing, MassExtend, MassArray, Goodassay, microarray miniseq, APEX (arrayed primer extension), sequence specific priming (SSP), microarray primer extension, Tag arrays, coded microspheres, template-directed incorporation (TDI), fluorescence polarization; oligonucleotide ligation methods such as colorimetric OLA, sequence-coded OLA, multiplex ligation-dependent probe amplification (MLPA), microarray ligation, ligase chain reaction, padlock probes and rolling circle amplification; endonuclease cleavage methods such as restriction site analysis (RFLP) and Invader™ assay; high-resolution melting (HRM) analysis for mutation scanning. In a preferred embodiment, the detection of the presence or absence of a nucleic acid variant is determined by DNA or RNA hybridization, sequencing, PCR, primer extension, MLPA, oligonucleotide ligation assay (OLA), restriction site analysis, or high-resolution melting (HRM) analysis for mutation scanning, or a combination thereof. Accordingly, the method of the present invention optionally comprises the steps of isolating nucleic acids from the sample and/or an amplification step.

The present invention also provides isolated oligonucleotides. i.e., primers and probes, in order to amplify and/or detect nucleic acid variants and/or the wild-type sequence of the SPTLC2 gene. The wild-type sequence of the SPTLC2 gene is identified by its genomic DNA sequence (SEQ ID NO:1) or cDNA sequence (SEQ ID NO:2). Such primers or probes, specifically hybridizing to the target nucleic acid, are of any convenient length such as to consist of at least 8, 9, 10, 11, 12, 13, 14 or 15 nucleotides and up to 40 nucleotides, up to 30 nucleotides or more conveniently up to 25 nucleotides in length, such as, for example, 8, 9, 10, 1, 12, 13, 14, 15, 16, 17, 18, 19, 20, 21, 22, 23, 24 or 25 nucleotides in length. In general, such primers or probes will comprise nucleotide sequences entirely complementary to the corresponding wild-type or variant locus in the SPTLC2 gene. However, if required one or more nucleotides may be added or one or more mismatches may be introduced, provided that the discriminatory power of the oligonucleotide primer or probe is not unduly affected.

An oligonucleotide primer (or primer pair) designed to specifically recognize and amplify either a wild-type or variant allele at a locus is referred to as an allele specific primer (or primer pair). The same applies for an allele specific probe, i.e., an oligonucleotide probe that specifically hybridizes to either a wild-type or variant allele.

Specific length and sequence of the probes and primers will depend on the complexity of the required nucleic acid target, as well as on the reaction conditions such as temperature and ionic strength. In general, the hybridization conditions are to be stringent as known in the art. "Stringent" refers to the condition under which a nucleotide sequence can bind to related or non-specific sequences. For example, high temperature and lower salt increases stringency such that non-specific binding or binding with low melting temperature will dissolve.

The primers or probes of the invention may carry one or more labels to facilitate detection. The nature of the label is not critical to the invention and may be fluorescent, chemiluminescent, enzymatic, radioactive, chemical or other, provided it doesn't interfere with correct hybridizing of the oligonucleotide.

In a preferred embodiment, the primer or probe consists of 10 to 30 nucleotides, preferably 15 to 30 or 15 to 25 nucleotides, and is capable of specifically forming a hybrid with a part of the SPTLC2 gene and is at least one or more selected from the group consisting of: 1) an oligonucleotide capable of hybridizing under a stringent condition with the sequence as represented by SEQ ID NO:1 or 2, or the complementary thereof; 2) an oligonucleotide of which the sequence is for 80, 85 or 90% identical to the sequence as represented by SEQ ID NO:1 or 2, or the complementary thereof; and 3) an oligonucleotide capable of hybridizing under a stringent condition with the sequence as represented by SEQ ID NO:1 or 2, wherein one or more nucleotides was subjected to a variation such as a substitution, deletion, insertion or addition, or the complementary thereof.

More particular, the present invention relates to an isolated oligonucleotide consisting of 10 to 30 nucleotides, preferably 15 to 30 or 15 to 25 nucleotides, for detecting the presence of one or more nucleic acid variants in SEQ ID NO:1 or 2, or the complementary strand. More specific, the nucleic acid variants are located at position 1145, 1075 or 1510 of SEQ ID NO:2.

The polymorphism located in the SPTLC2 gene may also be detected in vitro by determining in the isolated SPTLC2 protein the presence or absence of an amino acid change by sequencing said protein. The amino acid change may also be detected by any conventional method known in the art, for example, by mass-spectroscopy, gel electrophoresis, MALDI-TOF mass spectroscopy, ELISA, protein arrays, determination of the molecular weight, or by isoelectrofocusing.

Any human gene can be studied together with the method of the present invention. Of the different genetic markers identified, further important risk factors are polymorphisms or nucleic acid variations in one or more of the following genes (Rotthier et al. 2009):SPTLC1 (e.g., Bejaoui et al. 2001; Dawkins et al. 2001), RAB7A (e.g., Verhoeven et al. 2003; Meggouh et al. 2006), WNK1/HSN2 (e.g., Lafreniere et al. 2004), IKBKAP (e.g., Slaugenhaupt et al. 2001), FAM134B (e.g., Kurth et al. 2009), NTRK1 (e.g., Indo et al. 1996), NGFβ (e.g., Einarsdottir et al. 2004; Houlden et al. 2001), CCT5 (e.g., Bouhouche et al. 2006a), or SCN9A (e.g., Cox et al. 2006).

In a further embodiment, the method of the present invention may also be used in determining whether and which therapeutic agent might be suitable for a patient being at risk of, or having a sensory neuropathy disease. The therapeutic agent may be used to prevent or treat the disease. As used herein, the term "preventing a disease" means inhibiting or reversing the onset of the disease, inhibiting or reversing the initial signs of the disease, inhibiting the appearance of clinical symptoms of the disease. As used herein, the term "treating a disease" includes substantially inhibiting the disease, substantially slowing or reversing the progression of the disease, substantially ameliorating clinical symptoms of the disease or substantially preventing the appearance of clinical symptoms of the disease.

Another aspect of the invention relates to a diagnostic kit for use in the method as described herein. More specific, the invention encompasses a kit for identifying a subject at risk of, at risk of having, or having, a sensory neuropathy disease. This kit can be based on the detection of nucleic acid variants in the SPTLC2 gene of said subject. Accordingly, the kit of the present invention comprises reagents that selectively detect a nucleic acid variant in the SPTLC2 gene.

A kit based on the detection of nucleic acid variants in the SPTLC2 gene may comprise:
(a) a means or reagent for detecting the presence or absence of one or more nucleic acid variants in the SPTLC2 gene of said subject; and
(b) optionally, a means for determining, from the nucleic acid variants detected with the means of step (a), whether the subject is at risk of, or has, a sensory neuropathy disease.

More preferred, the kit comprises a means for detecting the presence or absence of one or more nucleic acid variants in the coding region of the SPTLC2 gene. In a preferred embodiment of the present invention, the kit comprises:
(a) a means or reagent for detecting the presence or absence of a nucleic acid variant at one or more of the following positions 1145, 1075 or 1510 of the coding region of the SPTLC2 gene, as can be identified by the cDNA sequence (SEQ ID) NO: 2); and
(b) optionally, a means for determining, from the nucleic acid variants detected with the means of step (a), whether the subject is at risk of, or has, an sensory neuropathy disease.

In a specific embodiment the means or reagents in step (a) of said kit may comprise, without limitation:

(i) when appropriate, a means for obtaining a target SPTLC2 polynucleic acid present in a biological sample and/or obtaining the nucleotide sequence thereof;
(ii) at least one oligonucleotide suitable for detection of a target SPTLC2 nucleic acid and/or at least one oligonucleotide pair suitable for amplification of a target SPTLC2 polynucleic acid;
(iii) when appropriate, an agent for denaturing nucleic acids;
(iv) when appropriate, an enzyme capable of modifying a double stranded or single stranded nucleic acid molecule;
(v) when appropriate, a hybridization buffer, or components necessary for producing said buffer;
(vi) when appropriate, a wash solution, or components necessary for producing said solution;
(vii) when appropriate, a means for detecting partially or completely denatured polynucleic acids and/or a means for detecting hybrids formed in the preceding hybridization and/or a means for detecting enzymatic modifications of nucleic acids;
(viii) when appropriate, a means for attaching an oligonucleotide to a known location on a solid support.

In a preferred embodiment the means or reagent in step (a) of said kit comprises at least one oligonucleotide probe suitable for detection of a target SPTLC2 nucleic acid. In a specific embodiment, the target SPTLC2 nucleic acid is located in the coding region, or part thereof. Even more specific, the target SPTLC2 nucleic acid is located at cDNA position 1145, 1075 and/or 1510 of the SPTLC2 gene. The designated positions either have the wild-type nucleotides or nucleic acid variants thereof. Optionally, the means or reagent in step (a) also includes at least one pair of primers suitable for amplification of a target SPTLC2 polynucleic acid. More particular, the target polynucleic acid is the coding region of the SPTLC2 gene, or part thereof. Even more specific, the target SPTLC2 polynucleic acid comprises cDNAposition 1145, 1075 and/or 1510 of the SPTLC2 gene. The designated positions either have the wild-type nucleotides or nucleic acid variants thereof.

The term "hybridization buffer" means a buffer allowing a hybridization reaction between the oligonucleotides and the polynucleic acids present in the sample, or the amplified products, under the appropriate stringency conditions. The term "wash solution" means a solution enabling washing of the hybrids formed under the appropriate stringency conditions.

In a specific embodiment of the kit, the means for detecting the presence or absence of nucleic acid variants in the SPTLC2 gene comprises a multiplex assay.

The means in step (b) of said kit, for determining, from the nucleic acid variants in the SPTLC2 gene detected with the means of step (a), whether the subject is at risk of, or has, a sensory neuropathy disease include a table, a chart, or similar, generally referred to as "a predisposition risk algorithm." indicating the SPTLC2 nucleic acid variants or haplotypes that confer a risk for or the existence of a sensory neuropathy disease. As used herein, the term "chart" refers to graphical presentation, visual aid, diagram, plan, graph, sheet, map or the like including the relevant information. The determination of the risk can be performed manually or with the use of a computer.

The kit of the present invention may include, in addition to the means or reagent for detecting the presence or absence of a nucleic acid variant, a means for detection other risk factors, e.g., nucleic acid variants in a gene, for a sensory neuropathy disease. In a preferred embodiment, the kit additionally includes a means, preferably probes, for detecting the genotype of or a nucleic acid variant in at least one of the genes selected from the group consisting of: SPTLC1, RAB7A, WNK1/HSN2. IKBKAP, FAM134B, NTRK1, NGFβ, CCT5 or SCN9A.

The following examples are intended to promote a further understanding of the present invention. While the present invention is described herein with reference to illustrated embodiments, it should be understood that the invention is not limited hereto. Those having ordinary skill in the art and access to the teachings herein will recognize additional modifications and embodiments within the scope thereof. Therefore, the present invention is limited only by the claims attached herein.

EXAMPLES

Example 1. Mutations in SPTLC2 are Associated with HSAN-I

The coding sequence and intron-exon boundaries of SPTLC2 (chromosome location 14q24.3) were analyzed in 78 patients with HSAN, previously screened and found negative for mutations in the other known HSAN genes (SPTLC1, RAB7A, the complete coding region of WNK1/HSN2, FAM134B, NTRK1, NGFB and CCT5) (Rotthier et al., 2009; Kurth et al. 2009). We identified three heterozygous missense mutations in four index patients, for whom clinical and electrophysiological information is summarized in Table 1 and Table 2. The mutations were absent in 300 European control individuals.

A c.1145G>T sequence variation (p.G382V) was found in two families (CMT-1044 and CMT-1117; FIG. 2a). The proband of Family CMT-1117 presented with progressive distal sensory loss and distal muscle weakness in the lower limbs at the age of 38 years. The clinical presentation was similar in a member of family CMT-1044. In addition, this patient experienced dysesthesia in hands and feet and developed osteomyelitis of a thumb. Based on haplotype analysis, these families were found to be unrelated (data not shown).

Figure 2B:
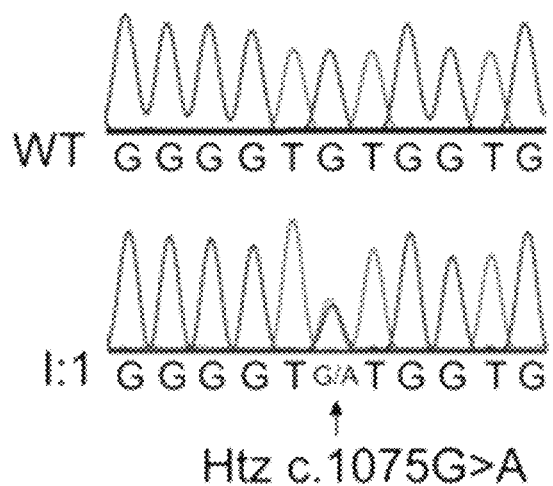

A second heterozygous mutation (c.1075G>A; p.V359M) was discovered in an isolated patient (CMT-747.I:1; FIG. 2b). This patient was diagnosed with HSAN after developing distal sensory dysfunction with a foot ulceration necessitating amputation of a toe. No signs of motor or autonomic involvement were noted.

Figure 2C:
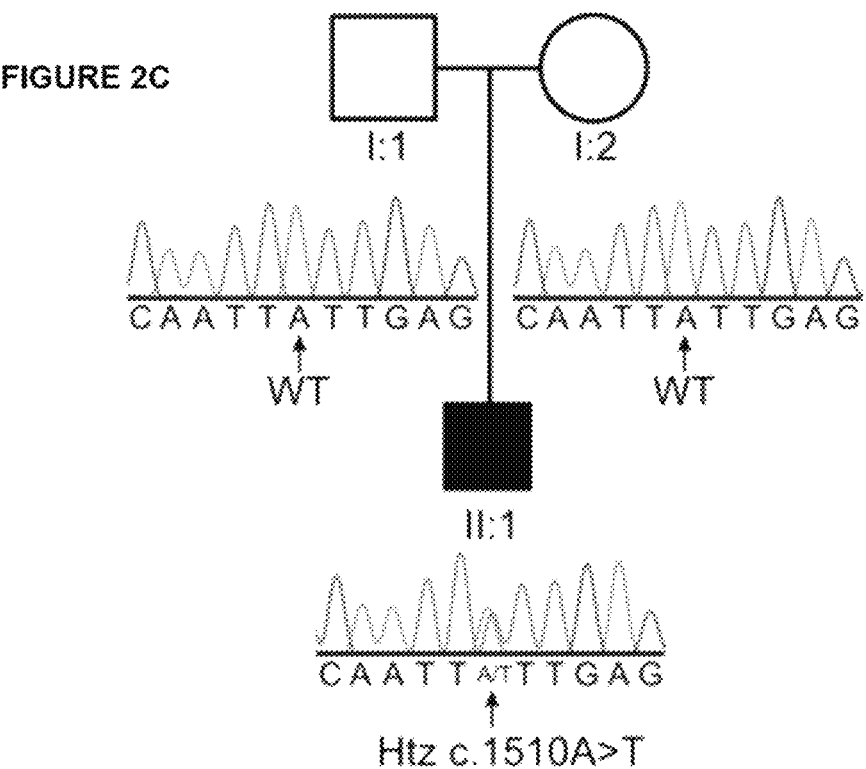

The third mutation (c.1510A>T; p.I504F) is a heterozygous de novo mutation found inpatient CMT-635.II:1 who presented with an atypical early onset sensorimotor neuropathy, complicated with ulcerations, osteomyelitis and anhidrosis (FIG. 2c). Paternity testing was done to confirm parenthood.

Nerve conduction studies were performed in all patients revealing predominantly axonal sensori-motor neuropathy; this diagnosis was confirmed by a sural nerve biopsy inpatient CMT-747.I:1 (Table 1 and Table 2).

No disease associated sequence variants were identified in the coding region or the intron-exon boundaries of SPTLC3 (chromosome location 20p12.1; GenBank accession number NM 018327).

Example 2. SPTLC2 Mutations are Associated with a Reduction in SPT Activity

Figure 4A:
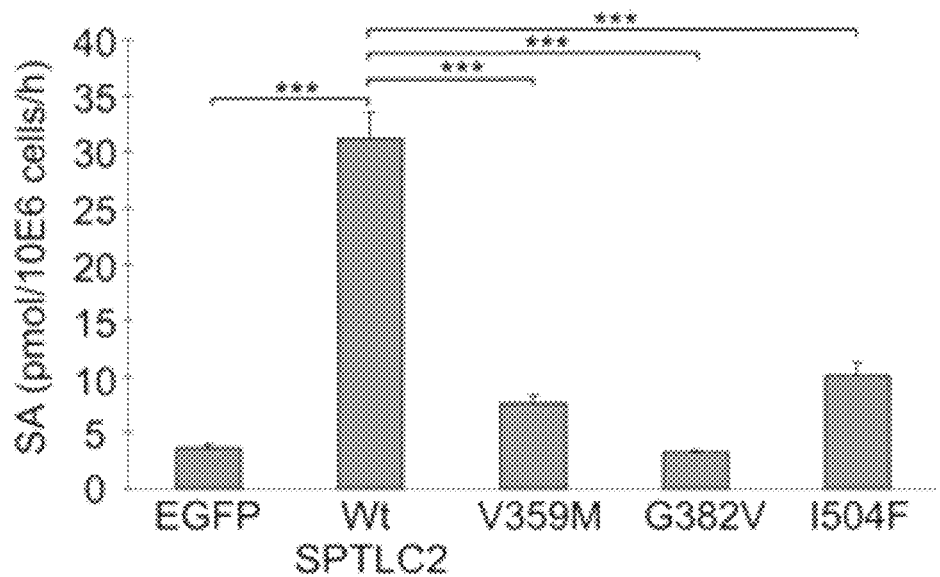
FIGS. 4A-4B. In vitro SPT activity measurements of HSAN-I associated SPTLC2 mutants. (A) Fumonisin B1 block assay. SPT activity in HEK293 cells stably expressing wt or mutant SPTLC2 is analyzed by measuring SA accumulation after treatment with Fumonisin B1. Stable expression of wt SPTLC2 generates an 8.5-fold increase in SPT activity (p=3.24E-5), while the G382V mutant does not increase the SPT activity (p=0.18). The V359M and I504F mutations increase the activity significantly (p=0.00063 and 0.00064, respectively) but not to the same extent as wt SPTLC2. EGFP transfected cells served as control. (B) Radioactive-based SPT activity assay. SPT activity of HEK293 cells stably expressing wt or mutant SPTLC2 was determined by measuring the incorporation of $^{14}$C-labeled L-serine in vitro. Stable expression of wt SPTLC2 results in a significant increase in SPT activity, whereas the expression of G382V fails to raise SPT activity above basal levels. Expression of the V359M or I504F mutant elevates SPT activity, but not as drastically as wt SPTLC2. The right bars represent SPT activity in the presence of the SPT inhibitor myriocin (negative control; see FIG. 1). CPM: Counts per minute. *** P-value <0.001; SA: sphinganine. Data is represented as a mean with error bars representing standard deviations. Error bars and standard deviation were calculated based on three independent experiments.

All three mutations in SPTLC2 target highly conserved amino acids (FIG. 3a) rendering it likely that they are functionally important. We set out to investigate the effect of these mutations on SPT activity in stably transfected Flp-in HEK293 cells. The Flp-in system ensures the stable insertion of a single copy of the transgene at a specific genomic location. In this way, moderate and equal expression of the different transgenes is obtained. The cells were treated for 24 h with Fumonisin B1, a mycotoxin that blocks the de novo sphingolipid biosynthesis pathway downstream of SPT (Wang et al. 1991) (FIG. 1). Since condensation of palmitoyl-CoA and serine by SPT is the rate-limiting step in the biosynthesis pathway, the resulting accumulation of sphinganine (SA) reflects the canonical SPT activity (incorporation of L-serine). Stable expression of wild-type (wt) SPTLC2 resulted in an 8-fold increase in SA accumulation compared to control cells stably expressing GFP. This is in agreement with earlier reports, in which overexpression of wt SPTLC2 indeed leads to higher SPT activity (Hornemann et al. 2006). Stable expression of the G382V mutant on the other hand did not increase SA accumulation above basal levels. The V359M and I504F expressing cells showed an increase in SA accumulation but far less pronounced than wt SPTLC2 expressing cells (FIG. 4a). Thus, the three mutations result in a partial to complete loss of SPT activity.

Figure 4B:
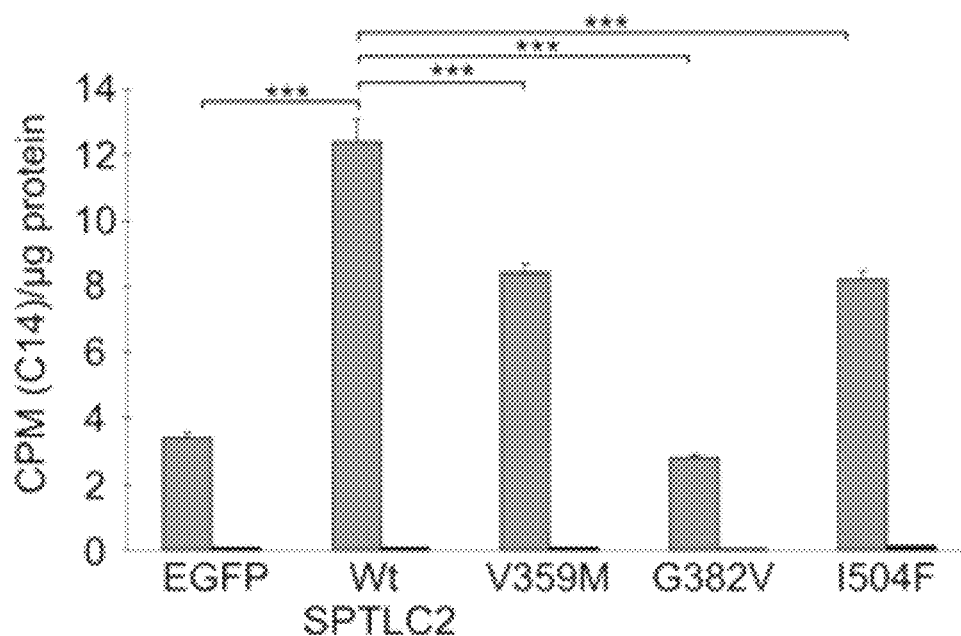

The effect on canonical SPT activity was confirmed in an alternative radioactive-based in vitro assay. Total lipids were extracted from HEK293 cells stably expressing wt or mutant SPTLC2 and incubated with $^{14}C$-labeled L-serine, PLP and palmitoyl-CoA after which the incorporation of the radioactively labeled serine was measured (FIG. 4b). The results resembled those of the previous assay. Stable expression of wt SPTLC2 caused a significant increase in SPT activity, whereas the expression of G382V failed to raise SPT activity above basal levels. Expression of the V359M or I504F mutant elevated SPT activity, but not to the same extent as wt SPTLC2. The relative increase in SPT activity in V359M and I504F expressing cells was more pronounced than in the Fumonisin B1 block assay (FIG. 4a). This difference could be explained by the higher serine concentration used in the latter in vitro assay compared to the serine concentrations present in the cell culture medium during the former assay.

Figure 5:
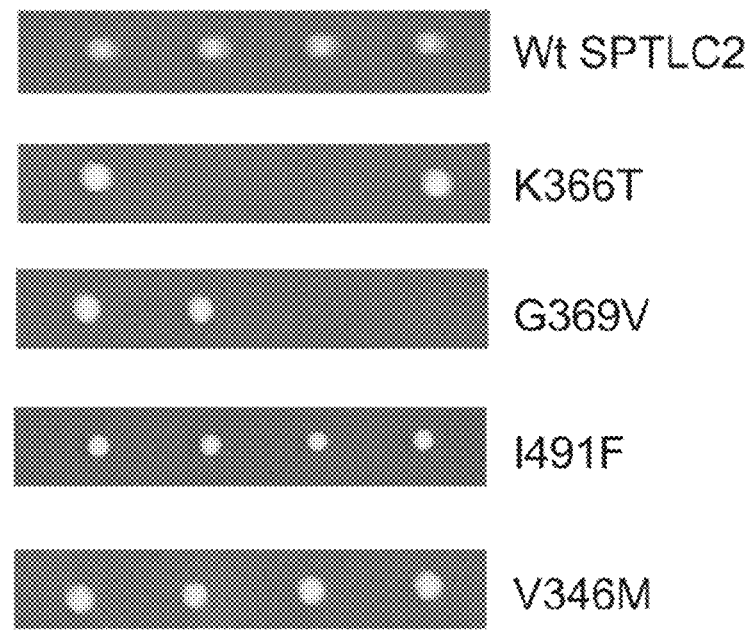
FIG. 5. Genetic complementation test in *S. cerevisiae* by tetrad dissection of a heterozygous LCB2/lcb2::KanMX strain complemented with different YCplac111_LCB2 constructs. Wild-type LCB2 can complement LCB2 deficiency, as shown by the appearance of four equally sized colonies on YPD medium without phytosphingosine at 37° C. The V346M (corresponding to V359M in SPTLC2) and I491F (corresponding to I504F in SPTLC2) LCB2 mutants also rescue the absence of endogenous LCB2. However, yeast transformed with the G369V (corresponding to G382V in SPTLC2) or K366T (dominant negative) mutants yields only colonies when endogenous LCB2 is present, demonstrating the failure of these mutants to complement LCB2 deficiency.

Example 3. SPTLC2 Mutants Differentially Affect In Vivo SPT Activity in S. cerevisiae To corroborate the loss of canonical SPT activity in vivo, we expressed the corresponding yeast mutants (FIG. 3A) in a heterozygous LCB2 deletion yeast strain (LCB2 is the S. cerevisiae orthologue of SPTLC2; the GenBank accession number for the LCB2 sequence is NM_001180370) and performed a tetrad analysis in order to obtain two haploid spores with and two without endogenous LCB2. As expected, all four spores grow at the permissive temperatures of 18° C., regardless of whether they expressed wt or mutant LCB2. At the restrictive temperature (37° C.), spores with (residual) SPT activity will be able to grow, while spores with no or non-functional LCB2 will depend on the external addition of phytosphingosine in order to generate phytosphingolipids and grow (Dunn et al. 2000). Wild-type LCB2 was able to complement the LCB2 deficiency, as apparent from the appearance of four equally sized colonies in the absence of phytosphingosine (FIG. 5). In contrast, but analogous to the dominant negative LCB2 K366T mutation (Gable et al. 2002), yeast spores expressing the G369V mutation (corresponding to G382V in SPTLC2) yielded only colonies when endogenous LCB2 was present, demonstrating the failure of this mutant to complement LCB2 deficiency. The residual activity conferred by the V346M and I491F mutants (corresponding to V359M and I504F respectively in SPTLC2) was sufficient to restore growth at 37° C.; this is in accordance with our biochemical data.

Example 4. Mutant SPT Shows Ambiguity Towards its Amino Acid Substrate

Figure 6A:
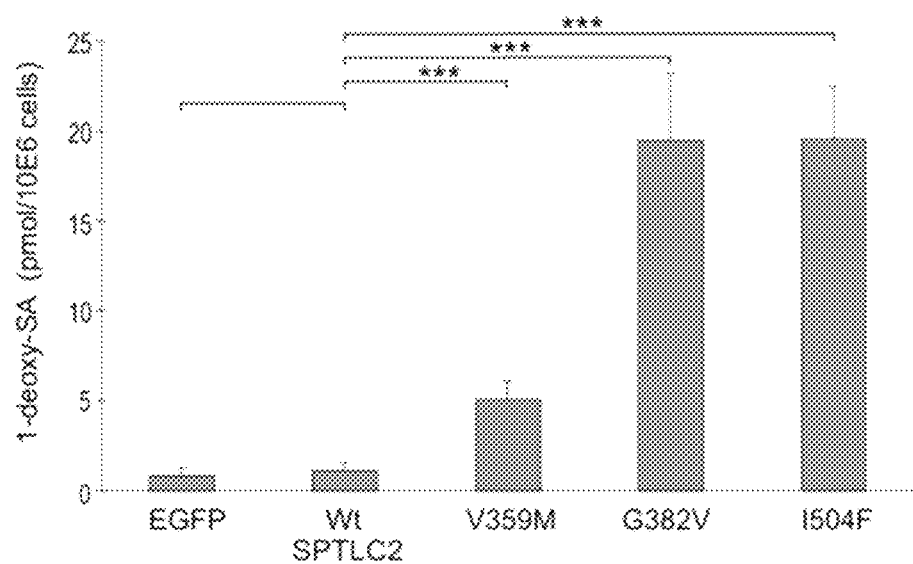
FIGS. 6A-6B. SPTLC2 mutations affect the enzymatic affinity of SPT. (A) Levels of 1-deoxy-SA in HEK293 cells stably expressing wt or mutant SPTLC2 are measured after an acid and base hydrolysis assay of the extracted lipids. Expression of wt SPTLC2 does not change cellular 1-deoxy-SA levels (p=0.55), whereas all three HSAN-I associated mutants result in significantly elevated 1-deoxy-SA levels (p=0.0025 for V359M; 0.00093 for G382V; 0.00048 for I504F). (B) 1-deoxy-SA levels in HSAN-I patient lymphoblastoid cell lines. The two HSAN-I patients CMT-1044.I:2 (G382V mutation) and CMT-635.II:1 (I504F mutation) show higher levels of 1-deoxy-SA compared to the unaffected parents of CMT-635.II:1 and to two unrelated control individuals. Unfortunately, no lymphoblast cells were available of patient CMT-747.I:1 carrying the V359M mutation. *** P-value <0.001; SA: sphinganine. Data is represented as a mean with error bars representing standard deviations. Error bars and standard deviation was calculated based on three independent experiments.

A recent report shows that SPTLC1 mutations in HSAN-I influence the substrate specificity of the SPT enzyme: mutant SPT is able to metabolize L-alanine and to a lesser extent glycine as alternative substrates. This results in the formation of the atypical and neurotoxic sphingoid base metabolites 1-deoxy-SA and 1-deoxymethyl-SA (Zitomer et al. 2009; Penno et al. 2010). The accumulation of these metabolites in the peripheral nerves was postulated to be the underlying cause of HSAN-I (Penno et al. 2010). To study whether SPTLC2 mutations likewise affect the enzymatic affinity of SPT and cause a similar accumulation of these alternative metabolites, the sphingoid base profile of HEK293 cells expressing the mutants was analyzed. In cells stably expressing wt SPTLC2, the amount of 1-deoxy-SA was similar to control cells (FIG. 6a), showing that an increase in SPT activity as such does not alter substrate specificity. Expression of the mutants on the other hand resulted in up to 20-fold higher 1-deoxy-SA levels compared to control cells, with highest levels in HEK cells stably expressing the G382V or I504F mutant enzyme. The generation of 1-deoxymethyl-SA levels in both HEK cells and lymphoblast cells was below detection limits.

Figure 6B:
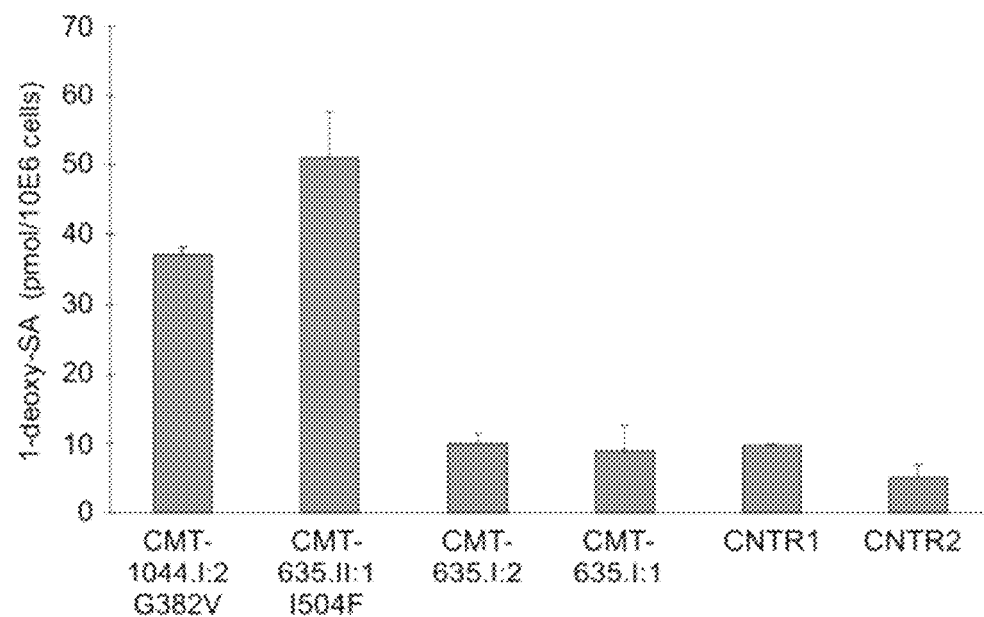

To validate if the results obtained in the HEK cells reflect the situation in HSAN-I patients, 1-deoxy-SA levels in lymphoblast cell lines from two HSAN-I patients, carrying respectively the G382V and I504F mutation, were measured. In both cell lines, accumulation of 1-deoxy-SA was observed when compared to unaffected family members or unrelated healthy control individuals (FIG. 6b). This finding is in agreement with our in vitro results and more importantly, shows that the accumulation of 1-deoxy-SA could be physiologically relevant.

Materials and Methods to the Examples

Subjects

For this study, a group of 78 patients was selected with hereditary ulcero-mutilating and sensory neuropathies. The inclusion criteria were described previously in Rotthier et al. 2009. The cohort shows a wide variability of clinical features and different modes of inheritance, but all patients share a progressive distal sensory dysfunction. Prior to enrolment in this study, informed consent from all patients or their legal representatives was obtained by the treating physicians.

Mutation Analysis

All DNA samples were amplified using the whole genome amplification kit "GenomiPhi V2 DNA Amplification Kit" (GE Healthcare). The coding regions and exon-intron boundaries up to 100 bp up- and downstream of the exons of SPTLC2 and SPTLC3 were PCR-amplified using oligonucleotide primers designed with the Primer3 and SNPbox software tools (Rozen and Skaletsky 2000; Weckx et al. 2004). Primer sequences are listed in Tables 3 and 4. Mutation screening was performed by direct DNA sequencing of purified PCR fragments using the BigDye® Terminator v3.1 Cycle Sequencing Kit (Applied Biosystems) and separated on an ABI3730xl DNA Analyzer (Applied Biosystems). The resulting sequences were aligned and analyzed with the novoSNP (Weckx et al. 2005) and SeqMan™ II programs. Sequence variants were confirmed by repeated PCR on original DNA samples and bidirectional sequencing.

Parenthood was tested using 15 highly informative short tandem repeats (STRs) distributed throughout the genome (ATA38A05, D1S1646, D1S1653, D1S1360, D2S2256, D3S3037, D4S2382, D4S3240, D7S509, D8S1759, D9S1118, D12S1056, D12S2082, D16S2619 and GATA152H04). STRs were PCR-amplified and PCR fragments were loaded on an ABI3730xl DNA Analyzer. Genotypes were analyzed using Local Genotype Viewer.

Cloning

The SPTLC2cDNA (NM 004863.2) was amplified and cloned into the Gateway® entry vector pDONR221 (Invitrogen) using the primers SPTLC2_attb1:
(SEQ ID NO: 4)
5'-gggacaagtttgtacaaaaaagcaggctatgcggccggagcccggag gctgct-3';
and SPTLC2_attb2:
(SEQ ID NO: 5)
5'-ggggaccactttgtacaagaaagctgggtccgtcttctgtttcttca tacgtc-3'.

The SPTLC2 mutations were introduced by site-directed mutagenesis, using the following primers:

SPTLC2_V359M_fw:
(SEQ ID NO: 6)
5'-ccacaggccggggtatggtggagtac-3'

SPTLC2_V359M_rv:
(SEQ ID NO: 7)
5'-gtactccaccataccccggcctgtgg-3'

SPTLC2_G382V_fw:
(SEQ ID NO: 8)
5'-gaacgttcacaaagagtttgttgcttctggaggatatattgg-3'

SPTLC2_G382V_rv:
(SEQ ID NO: 9)
5'-ccaatatatcctccagaagcaacaaaactctttgtgaacgttc-3'

SPTLC2_I504F_fw:
(SEQ ID NO: 10)
5'-ttcctgccaccccaattttgagtccagagcc-3'

SPTLC2_I504F_rv:
(SEQ ID NO: 11)
5'-ggctctggactcaaaaattggggtggcaggaa-3'.

The constructs were recombined in the destination vectorpEFS/FRT/V5-DEST (Invitrogen), fusing the cDNA with a C-terminal V5-tag. All constructs were validated by sequencing. Stable cell lines were generated using the Flp-in host cell line HEK293 following manufacturer's instructions (Invitrogen).

The yeast LCB2 gene together with its own promotor (700 bp upstream of start codon) and own terminator (450 bp downstream of stopcodon) was cloned into the YCplac111 plasmid vector, harboring a LEU2 gene. Mutations and a HA-tag were introduced with site-directed mutagenesis using the following primers:

LCB2_HA_fw:
(SEQ ID NO: 12)
5'-gccactacctgagcccgttgtcagcgtagtctgggacgtcgtatggg taagcgtagtctgggacgtcgtatgggtaagcgtagtctgggacgtcgta tgggtagacacccctccttattacatttc-3'

LCB2_HA_rv:
(SEQ ID NO: 13)
5'-gaaatgtaataaggaggggtgtctacccatacgacgtcccagactac gcttacccatacgacgtcccagactacgcttacccatacgacgtcccaga ctacgctgacaacgggctcaggtagtggc-3'

LCB2_V346M_fw:
(SEQ ID NO: 14)
5'-gcccaactggtcgcggtatgtgtgaaatatttggcg-3'

LCB2_V346M_rv:
(SEQ ID NO: 15)
5'-cgccaaatatttcacacataccgcgaccagttgggc-3'

LCB2_G369V_fw:
(SEQ ID NO: 16)
5'-gtactttcactaagtcgtttgttgctgctggtggttacattg-3'

LCB2_G369V_rv:
(SEQ ID NO: 17)
5'-caatgtaaccaccagcagcaacaaacgacttagtgaaagtac-3'

LCB2_I491F_fw:
(SEQ ID NO: 18)
5'-cttatcctgctactccgctgtttgaatcaagagtaagattctg-3'

LCB2_I491F_rv:
(SEQ ID NO: 19)
5'-cagaatcttactcttgattcaaacagcggagtagcaggataag-3'

LCB2_K366T_fw:
(SEQ ID NO: 20)
5'-ctaatgggtactttcactacttcgtttggtgctgctggtg-3'

LCB2_K366T_rv:
(SEQ ID NO: 21)
5'-caccagcagcaccaaacgaagtagtgaaagtacccattag-3'

Cell Culture Material and Conditions

HEK293 Flp-in cells were cultivated at 37° C. and 5% $CO_2$ in DMEM supplemented with 10% fetal bovine serum, L-glutamine and penicillin/streptomycin. Lymphoblastoid cell lines were cultured at 37° C. and 5% $CO_2$ in RPMI supplemented with 10% fetal bovine serum, L-glutamine, sodium pyruvate and penicillin/streptomycin. All cell culture media and supplements were from Invitrogen.

Lymphoblastoid Cell Lines

Total blood samples were mixed with 15 ml of FicolPaque and centrifuged for 10 min. After washing, lymphocytes were transformed with Epstein-Barr virus and incubated at 37° C. for 2 h. After centrifugation, the pellet was resuspended in 4 ml RPMI complete medium+1% phytohaemagglutinin. Cells were seeded in a 24-well plate and incubated at 37° C. and 5% $CO_2$ for a minimum of 3 days. Cells were split and supplemented with fresh medium as needed.

Yeast Complementation Assay

The YCplac111 constructs containing wt or mutant LCB2 were transformed (Gietz et al. 2007) in a heterozygous LCB2 deletion strain (BY4743), in which LCB2 has been replaced by a kanamycin resistance gene, and sporulated. The resulting tetrads were dissected to obtain haploid spores which lack endogenous expression of LCB2 and grown on YPD medium with phytosphingosine (15 µM; Avanti Polar Lipids) and 0.1% tergitol at 26° C. After two days, replica plating to different growth media was performed, namely YPD medium at 18° C. and 37° C. (yeast SPT mutants have a thermo-sensitive growth phenotype [Dunn et al. 2000]), synthetic minimal medium without leucine (allowing for selection of transformed spores) and YPD medium with geneticin (selection of LCB2-deficient spores). For each construct, at least six tetrads were analyzed. Unless specified otherwise, media and supplements were from Sigma.

RNA Isolation and mRNA Analysis

Total mRNA was purified using the RNeasy mini kit (Qiagen). DNA inactivation was performed using the Turbo DNA free kit (Ambion) and cDNA synthesis was done with Superscript III first strand synthesis system for RT-PCR (Invitrogen). Expression of SPTLC2 (endogenous and construct) was analyzed using the following primer combinations:

SPTLC2_Fw:
(SEQ ID NO: 22)
5'-gagtccagagccaggttttg-3';
and

SPTLC2_3'UTR_Rv:
(SEQ ID NO: 23)
5'-ctgagggagcaccaaaaag-3'
(for endogenous SPTLC2 expression);
or V5_Rv:
(SEQ ID NO: 24)
5'-gagagggttagggataggcttac-3'
(for SPTLC2 construct).

Real time qPCR (RT-qPCR) reactions were performed in triplicate with 10 ng cDNA in SYBR Green I mix (Applied Biosystems) and run on ABI Prism 7900 HT Sequence Detection System (Applied Biosystems). Primers were validated for specificity and amplification efficiency. RT-qPCR data were normalized according to the method described by Vandesompele et al. 2002. The relative expression levels were used to normalize the data of the Fumonisin B1 block assay, the in vitro SPT activity assay and the 1-deoxy-SA quantification.

Fumonisin B1 Block Assay

This assay was performed as described in Penno et al. 2010. Briefly, Fumonisin B1 (Sigma) was added to the media of exponentially growing cells in a final concentration of 10 µg/ml. As a negative control, the SPT inhibitor myriocin (10 µg/ml, Sigma) was added together with Fumonisin B1. 24 hours after Fumonisin B1 addition, cells were washed twice with PBS, harvested and counted (Coulter® Z2, Beckman Coulter). Next, the cells were subjected to lipid extraction under basic conditions (see below). Sphingoid bases were quantified by LC-MS. Synthetic C17 sphingosine (Avanti Polar Lipids) was added to each sample as an internal extraction standard.

In Vitro Radioactive-Based SPT Activity Assay

SPT activity was measured using the radioactivity-based assay described by Rütti et al. 2009. In brief, 400 µg total cell lysate, 50 mM HEPES (pH 8.0), 0.5 mM L-serine, 0.05 mM Palmitoyl-CoA, 20 µM Pyridoxal-5'-phosphate, 0.2% sucrose monolaurate (all from Sigma) and 0.1 µCi L-[U-14C] serine (Amersham) were mixed and incubated at 37° C. In the control reaction, SPT activity was specifically blocked by the addition of myriocin (40 µM, Sigma). After 60 min, the reaction was stopped and lipids were extracted according to the method of Riley et al. 1999 (see below).

Lipid Extraction and Hydrolysis

Total lipids were extracted from cells or plasma and extracted according to the method of Riley et al. 1999. For acid hydrolysis, the dried lipids were resuspended in 200 µl methanolicHCl (1N HCl/10M water in methanol) and kept at 65° C. for 12-15 hours. The solution was neutralized by the addition of 40 µl KOH (5M) and subsequently subjected to base hydrolysis, which was performed as follows: 0.5 ml extraction buffer (4 vol. 0.125M KOH in methanol+1 vol. chloroform) was added to the solution. Subsequently, 0.5 ml chloroform, 0.5 ml alkaline water and 100 µl 2M ammonia were added in this order. Liquid phases were separated by centrifugation (12.000 g, 5 min). The upper phase was aspirated and the lower phase washed twice with alkaline water. Finally, the lipids were dried by evaporation of the chloroform phase under N2 and subjected to liquid chromatography-mass spectrometry (LC-MS) analysis.

Extracted lipids were solubilized in 56.7% methanol-33.3% ethanol-10% water and derivatized with ortho-phthalaldehyde. The lipids were separated on a C18 column (Uptispere 120 Å, 5 µm, 125×2 mm, Interchim, France) fluorescence detector (HP1046A, Hewlett Packard) followed by detection on a MS detector (LCMS-2010A. Shimadzu). APCI (atmospheric pressure chemical ionisation) was used for ionization. Non-natural C17 sphingosine (Avanti Polar Lipids) was used as internal standard. Retention times were as follow: $C_{17}SO$ (int.STD): 6 min: sphingosine: 7.5 min; 1-deoxysphingosine: 9 min; 1-deoxymethylsphingosine: 10.5 min; sphinganine: 10.5 min, 1-deoxymethylsphinganine: 13 min; 1-deoxysphinganine: 13.5 min. MS data were analyzed using LCMS solution (Shimadzu) and MS Processor v.11 (ACD Labs).

Statistics

The two-tailed unpaired Student's t-test was used for statistical analysis. Error bars (standard deviation) and p-values (Student t-test) were calculated based on three independent experiments.

TABLE 1

| Patient | Origin | Mutation | Familial history | Onset | Presenting symptoms | Disease duration | Ulcerations | Osteomyelitis |
|---|---|---|---|---|---|---|---|---|
| CMT-747.I:1 | Austria | c.1075G > A p.V369M | IC | 52 y | Ulceration and amputation great toe R | 27 y | + (loes) | + |
| CMT-1044.I:2 | Germany | c.1145G > T p.G382V | D | 37 y | Dysesthesia and sensory loss distal UL and LL | 35 y | − | + (thumb R) |
| CMT-1117.II:1 | Austria | c.1145G > T p.G382V | D | 38 y | Sensory loss in feet | S y | − | − |
| CMT-1117.I:2 | Austria | c.1145G > T p.G382V | D | ? | Asymptomatic | ? | − | − |
| CMT-635.I:1 | Czech Republic | c.1510A > T p.I504F | IC (de novo) | 5 y | Gait difficulties, foot deformities | 9 y | + (LL) | + |

| Patient | Amputations | Sensory dysfunction | Autonomic dysfunction | Distal weakness | NCS | Additional |
|---|---|---|---|---|---|---|
| CMT-747.I:1 | + | + (distal LL) | − | − | Axonal/intermediate sensorimotor | Sural nerve biopsy: axonal neuropathy in particular of unmyelinated fibers |
| CMT-1044.I:2 | − | + severe distally panmodal with dysesthesia | − | + UL (0-3/5) and LL (0/5) | Axonal intermediate sensorimotor | Scoliosis, focal epilepsy; Brisk Reflexes UL; Claw hand R > L |
| CMT-1117.II:1 | − | + distally for touch and vibration | − | + LL (2/5) | Axonal sensorimotor | — |
| CMT-1117.I:2 | − | + distally LL for vibration | − | + LL (5-/5) | Axonal sensorimotor | Type 2 diabetes (onset 71 y) |
| CMT-635.II:1 | − | + | + | + (LL) | Intermediate sensorimotor | — |

TABLE 2

| Patient | Age | | Median motor Amp | CV | Ulnar Motor Amp | CV | Peroneal motor Amp | CV | Tibial motor Amp | CV | Median sensory Amp | CV | Ulnar sensory Amp | CV | Sural sensory Amp | CV |
|---|---|---|---|---|---|---|---|---|---|---|---|---|---|---|---|---|
| Normal Values≥ | | | 4.0 | 49.0 | 4.0 | 49.0 | 3.0 | 41.0 | 3.0 | 41.0 | 7.0 | 46.0 | 2.0 | 47.0 | 1.0 | 44.0 |
| CMT-747.I:1 | 79 y | R | 9.7 | 44.3 | — | — | 0.1 | 35.7 | — | — | A | A | — | — | — | — |
| | | L | 8.4 | 51.0 | — | — | 0.1 | 23.3 | — | — | 0.9 | 35.2 | — | — | — | — |
| CMT-1044.I:2 | 72 y | R | 0.1 | 34.0 | 0.5 | 37.0 | A | A | A | A | A | A | A | A | A | A |
| CMT-1117.II:1 | 44 y | R | 6.2 | 55.0 | — | — | A | A | A | A | A | A | 0.4 | 38.0 | A | A |
| CMT-1117.I:2 | 72 y | R | 9.9 | 47.0 | 5.6 | 51.0 | 3.0 | 42.0 | — | — | — | — | — | — | 2.7 | 33.0 |
| CMT-635.II:1 | 14 y | R | 3.8 | 25.0 | 2.9 | 50.0 | A | A | A | A | A | A | A | A | A | A |
| | | L | 2.0 | 29 | 2.1 | 53 | A | A | A | A | — | — | — | — | — | — |

TABLE 3

Exon primers used for PCR and direct sequencing of SPTLC2.

| | Forward primer (5'-3') | SEQ ID NOs | Reverse primer (5'-3') | SEQ ID NOs |
|---|---|---|---|---|
| Exon 1 | gcagccatttccggtttc | 25 | ggattgcccagcggatgg | 26 |
| Exon 2 | ttacaggtgtgagccagtgc | 27 | tgtgcaaaaatactaagatttc | 28 |
| Exon 3 | cacaatcttgcacgtaatgaaa | 29 | cctcagctgctactcctattttg | 30 |
| Exon 4 | tctgcttccttttgtgtcacc | 31 | tcagaaaaacaaagcattcttca | 32 |
| Exon 5 | agtctgaaaaggacacaacaca | 33 | gctcactctgactgcttttcaa | 34 |
| Exon 6 | tgatcactgtgctgttgtgc | 35 | aagactggaccggaagaacat | 36 |
| Exon 7 | tgaggcatggtttctgaatg | 37 | tgctgactctgtttccaggt | 38 |
| Exon 8 | acttcagcctggacaatgga | 39 | gagcctaaaccagaggcaaa | 40 |
| Exon 9 | gaccatgttggttgaccttgt | 41 | gtccatggaaaccacacacc | 42 |
| Exon 10 | aaatattttatggtgaaatggaaaa | 43 | tggcatatgtaccaaatgaagg | 44 |
| Exon 11 | gcctgcatcaccaaagagtt | 45 | cactgtcaccccctctgtct | 46 |
| Exon 12 | cctgccgaaggataatcttg | 47 | gcaaaggaaggattagaagca | 48 |

TABLE 4

Exon primers used for PCR and direct sequencing of SPTLC3.

| | Forward primer (5'-3') | SEQ ID NOs | Reverse primer (5'-3') | SEQ ID NOs |
|---|---|---|---|---|
| Exon 1 | caaacggtgcagagacc | 49 | aacccttcataagatgaactcta | 50 |
| Exon 2 | taacaggagaatgctaacctt | 51 | cactttagagaggagtaggc | 52 |
| Exon 3 | agataaccttctacctctgttctaa | 53 | ttgtcatctagtggccat | 54 |
| Exon 4 | gaatcgtgcataatcctgg | 55 | agagacagacacaaggaat | 56 |
| Exon 5 | aatcttggccttgttgaaa | 57 | tctaacaaggacctactcaga | 58 |
| Exon 6 | ctgtccccacaagttgtttt | 59 | gtcaccttgaagagcagaa | 60 |
| Exon 7 | tttaggtctgagtgtgaacata | 61 | tctgtttagctaggaaaggtga | 62 |
| Exon 8 | ggagggtatttgttagtta | 63 | ggtgtggtgaactgaattg | 64 |
| Exon 9 | agggatgggactagatgta | 65 | gggagattaatgaggcagaa | 66 |
| Exon 10 | atgcttgccaagttgac | 67 | cataatctaacgcctgtgc | 68 |
| Exon 11 | catattccttttttgtcag | 69 | taaataacccaagagaaac | 70 |
| Exon 12 | gctattaatctgggctctg | 71 | ggagaaatccatttatattccttg | 72 |

REFERENCES

Auer-Grumbach M, De Jonghe P, Verhoeven K, Timmerman V, Wagner K, Hartung H P, et al. Autosomal dominant inherited neuropathies with prominent sensory loss and mutilations: a review. Arch Neurol 2003; 60: 329-34.

Auer-Grumbach M. Hereditary sensory neuropathies. Drugs Today 2004; 40: 385-94.

Ausubel F M, Brent R, Kingston R E. Moore D D, Seidman J G, Smith J A and Struhl K. Series Editor: Virginia Benson Chanda. Current Protocols in Molecular Biology 2003, John Wiley & Sons.

Bejaoui K, Wu C, Scheffler M D, Haan G, Ashby P. Wu L, et al. SPTLC1 is mutated in hereditary sensory neuropathy, type I. Nat Genet 2001: 27: 261-2.

Bouhouche A, Benomar A, Bouslam N, Chkili T, Yahyaoui M. Mutation in the epsilon subunit of the cytosolic chaperonin-containing t-complex peptide-1 (Cct5) gene causes autosomal recessive mutilating sensory neuropathy with spastic paraplegia. J Med Genet 2006a; 43: 441-3.

Bouhouche A, Benomar A, Bouslam N, Ouazzani R, Chkili T, Yahyaoui M. Autosomal recessive mutilating sensory neuropathy with spastic paraplegia maps to chromosome 5p15.31-14.1. Eur J Hum Genet 2006b; 14: 249-52.

Cox, J. J., Reimann, F., Nicholas, A. K., Thornton, G., Roberts, E., Springell, K., Karbani, G., Jafri, H., Mannan, J., Raashid, Y., Al-Gazali, L., Hamamy, H., Valente, E. M., Gorman, S., Williams. R., McHale, D. P., Wood, J. N., Gribble, F. M., Woods, C. G. An SCN9A channelopathy causes congenital inability to experience pain. Nature 444: 894-898, 2006.

Dawkins J L, Hulme D J, Brahmbhatt S B, Auer-Grumbach M, Nicholson G A. Mutations in SPTLC1, encoding serine palmitoyltransferase, long chain base subunit-1, cause hereditary sensory neuropathy type I. Nat Genet 2001; 27: 309-12.

Dawkins, J. L., Brahmbhatt, S. B., Auer-Grumbach, M., Wagner, K., Hartung, H. P., Verhoeven. K., Timmerman V, De Jonghe P, Kennerson, M. L., LeGuern, E. et al. (2002). Exclusion of serine palmitoyltransferase subunit 2 (SPTLC2) as a common cause for hereditary sensory neuropathy. Neuromusc. Disord. 12, 656-658.

Dunn, T. M., Gable, K., Monaghan, E., and Bacikova, D. (2000). Selection of yeast mutants in sphingolipid metabolism. Methods Enzymol. 312, 317-330.

Dyck P J. Neuronal atrophy and degeneration predominantly affecting peripheral sensory and autonomic neurons. In: Dyck P J, Thomas P K, Griffin J W, Low P A, Poduslo J F, editors. Peripheral neuropathy. 3rd edn., Philadelphia: W.B. Saunders; 1993. p. 1065-93.

Einarsdottir E, Carlsson A, Minde J, Toolanen G, Svensson O, Solders G, et al. A mutation in the nerve growth factor beta gene (NGFB) causes loss of pain perception. Hum Mol Genet 2004; 13: 799-805.

Gable, K., Han, G., Monaghan, E., Bacikova, D., Natarajan, M., Williams, R., and Dunn, T. M. (2002). Mutations in the yeast LCB1 and LCB2 genes, including those corresponding to the hereditary sensory neuropathy type I mutations, dominantly inactivate serine palmitoyltransferase. J. Biol. Chem. 277, 10194-10200.

Gietz, R. D. and Schiestl, R. H. L (2007). High-efficiency yeast transformation using the LiAc/SS carrier DNA/PEG method. Nat. Protoc. 2, 31-34.

Gut L G. (2001) Automation in genotyping of single nucleotide polymorphisms. Hum. Hornemann, T., Wei, Y., and von Eckardstein, A. (2007). Is the mammalian serine palmitoyltransferase a high-molecular-mass complex? Biochem. J. 405, 157-164.

Indo Y, Tsuruta M, Hayashida Y, Karim M A, Ohta K, Kawano T, et al. Mutations in the TRKA/NGF receptor gene inpatients with congenital insensitivity to pain with anhidrosis. Nat Genet 1996; 13: 485-8.

Kok C, Kennerson M L, Spring P J, Ing A J, Pollard J D, Nicholson G A. A locus for hereditary sensory neuropathy with cough and gastroesophageal reflux on chromosome 3p22-p24. Am J Hum Genet 2003; 73: 632-7.

Kurth, I., Pamminger, T., Hennings, J. C., Soehendra, D., Huebner, A. K., Rotthier, A., Baets, J., Senderek, J., Topaloglu, H., Farrell, S. A. et al. (2009). Mutations in FAM134B, encoding a newly identified Golgi protein, cause severe sensory and autonomic neuropathy. Nat. Genet. 41, 1179-1181.

Lafreniere R G, MacDonald M L, Dube M P, MacFarlane J, O'Driscoll M, Brais B, et al. Identification of a novel gene (HSN2) causing hereditary sensory and autonomic neuropathy type 11 through the Study of Canadian Genetic Isolates. Am J Hum Genet 2004; 74: 1064-73.

Meggouh F, Bienfait H M, Weterman M A, de Visser M, Baas F. Charcot-Marie-Tooth disease due to a de novo mutation of the RAB7 gene. Neurology 2006; 67: 1476-8.

Nollau P, Wagener C. (1997) Methods for detection of point mutations: performance and quality assessment. IFCC Scientific Division. Committee on Molecular Biology Techniques. Clin Chem., 43(7): 1114-28.

Penno, A., Reilly, M. M., Houlden, H., Laura, M., Rentsch, K., Niederkofler, V., Stoeckli, E. T., Nicholson, G., Eichler, F., Brown, R. H., Jr. et al. (2010). Hereditary sensory neuropathy type 1 is caused by the accumulation of two neurotoxic sphingolipids. J. Biol. Chem. 285, 11178-11187.

Riley, R. T., Norred, W. P., Wang, E., and Merrill, A. H. (1999). Alteration in sphingolipid metabolism: Bioassays for fumonisin- and ISP-I-like activity in tissues, cells and other matrices. Natural Toxins 7, 407-414.

Rotthier, A., Baets, J., De Vriendt, E., Jacobs, A., Auer-Grumbach, M., Levy, N., Bonello-Palot, N., Kilic, S. S., Weis, J., Nascimento, A. et al. (2009). Genes for hereditary sensory and autonomic neuropathies: a genotype-phenotype correlation. Brain 132, 2699-2711.

Rozen, S. and Skaletsky, H. (2000). Primer3 on the WWW for general users and for biologist programmers. Methods Mol. Biol. 132, 365-386.

Rutti, M. F., Richard, S., Penno, A., von Eckardstein, A., and Hornemann, T. (2009). An improved method to determine serine palmitoyltransferase activity. J. Lipid Res. 50, 1237-1244.

Sambrook J., Fritsch E. and Maniatis T. (1989) Molecular cloning: a laboratory manual. Cold Spring Harbor Laboratory Press, Cold Spring Harbor, N.Y., USA.

Slaugenhaupt S A, Blumenfeld A, Gill S P, Leyne M, Mull J, Cuajungco M P, et al. Tissue-specific expression of a splicing mutation in the IKBKAP gene causes familial dysautonomia. Am J Hum Genet 2001; 68: 598-605.

Syvanen A. C. (2001) Accessing genetic variation: genotyping single nucleotide polymorphisms. Nat. Rev. Genet. 2: 930-942.

Vandesompele, J., de Preter, K., Pattyn, F., Poppe, B., Van Roy, N., De Paepe, A., and Speleman, F. (2002). Accurate normalization of real-time quantitative RT-PCR data by geometric averaging of multiple internal control genes. Genome Biol. 3, 1-12

Verhoeven K, De Jonghe P, Coen K, Verpoorten N, Auer-Grumbach M, Kwon J M, et al. Mutations in the small GTP-ase late endosomal protein RAB7 cause Charcot-Marie-Tooth type 2B neuropathy. Am J Hum Genet 2003; 72: 722-7.

Verhoeven K, Timmerman V, Mauko B, Pieber T R, De Jonghe P, Auer-Grumbach M. Recent advances in hereditary sensory and autonomic neuropathies. Curr Opin Neurol 2006; 19: 474-80.

Verpoorten N, Clacys K G, Deprez L, Jacobs A, Van Gerwen V, Lagae L, et al. Novel frameshift and splice site mutations in the neurotrophic tyrosine kinase receptor type 1 gene (NTRK1) associated with hereditary sensory neuropathy type IV. Neuromuscul Disord 2006b; 16: 19-25.

Verpoorten N, De Jonghe P, Timmerman V. Disease mechanisms in hereditary sensory and autonomic neuropathies. Neurobiol Dis 2006a; 21: 247-55.

Wang, E., Norred, W. P., Bacon, C. W., Riley, R. T., and Merrill, A. H., Jr. (1991). Inhibition of sphingolipid biosynthesis by fumonisins. Implications for diseases associated with *Fusarium moniliforme*. J. Biol. Chem. 266, 14486-14490.

Weckx, S., De Rijk, P., Van Broeckhoven, C., and Del Favero, J. (2004). SNPbox: web-based high-throughput primer design from gene to genome. Nucleic Acids Research 32, W170-172.

Weckx, S., Del Favero, J., Rademakers, R., Claes, L., Cruts, M., De Jonghe, P., Van Broeckhoven, C., and De Rijk, P. (2005). novoSNP, a novel computational tool for sequence variation discovery. Genome Res. 15, 436-442.

Zitomer, N. C., Mitchell, T., Voss, K. A., Bondy, G. S., Pruett, S. T., Garnier-Amblard, E. C., Liebeskind, L. S., Park, H., Wang, E., Sullards, M. C. et al. (2009). Ceramide synthase inhibition by fumonisin B1 causes accumulation of 1-deoxysphinganine: a novel category of bioactive 1-deoxysphingoid bases and 1-deoxydihydroceramides biosynthesized by mammalian cell lines and animals. J. Biol. Chem. 284, 4786-4795.

Staud R, Price D D, Janicke D, Andrade E, Hadjipanayis A G, Eaton W T, Kaplan L, Wallace M R. Two novel mutations of SCN9A (Nav1.7) are associated with partial congenital insensitivity to pain. Eur J Pain. 2010 Aug. 6.

Cox J J, Sheynin J, Shorer Z, Reimann F. Nicholas A K, Zubovic L, Baralle M, Wraige E, Manor E, Levy J, Woods C G, Parvari R. Congenital insensitivity to pain:novel SCN9A missense and in-frame deletion mutations. Hum Mutat. 2010 September; 31(9):E1670-86.

Kurban M, Wajid M, Shimomura Y. Christiano A M. A nonsense mutation in the SCN9A gene in congenital insensitivity to pain. Dermatology. 2010; 221(2):179-83.

The invention claimed is:

1. A nucleic acid probe comprising a fragment of a SPTLC2 sequence or the complementary sequence thereof, wherein the SPTLC2 sequence has the sequence of SEQ ID NO: 2, and comprises a mutation in at least one nucleotide position selected from the group consisting of 1145, 1075, and 1510 relative to the ATG start codon beginning at position 189 of SEQ ID NO:2; and wherein the nucleic acid probe hybridizes to the variant SPTLC2 sequence but not to the wild type SPTLC2 sequence, wherein the nucleic acid probe is 25 to 100 nucleotides in length, and wherein the nucleic acid probe is detectably labeled with a fluorescent, chemiluminescent, enzymatic, radioactive, or chemical label.

2. The nucleic acid probe of claim 1, wherein the mutation is selected from the group consisting of c.1075G>A, c.1145G>T, and c.1510 A>T of the SPTLC2 sequence.

3. The nucleic acid probe of claim 1, wherein the nucleic acid probe is directly labeled with a fluorescent label.

4. The nucleic acid probe of claim 1, wherein the probe is 25-30 nucleotides long.

5. The nucleic acid probe of claim 1, wherein the probe is 25-40 nucleotides long.

6. A kit for detecting a mutation in SPTLC2 nucleic acid, comprising the nucleic acid probe of claim 1.

* * * * *